US012588678B2

(12) United States Patent
Wang et al.

(10) Patent No.: US 12,588,678 B2
(45) Date of Patent: Mar. 31, 2026

(54) OXAZOLINE COMPOUND, SYNTHESIS METHOD THEREFOR AND APPLICATION THEREOF

(71) Applicant: NANKAI UNIVERSITY, Tianjin (CN)

(72) Inventors: Qingmin Wang, Tianjin (CN); Yuxiu Liu, Tianjin (CN); Ziwen Wang, Tianjin (CN); Hongjian Song, Tianjin (CN); Yongqiang Li, Tianjin (CN); Shilin Chen, Tianjin (CN); Yu Zhang, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 993 days.

(21) Appl. No.: 17/621,900

(22) PCT Filed: Sep. 24, 2020

(86) PCT No.: PCT/CN2020/117485
§ 371 (c)(1),
(2) Date: Dec. 22, 2021

(87) PCT Pub. No.: WO2021/057852
PCT Pub. Date: Apr. 1, 2021

(65) Prior Publication Data

US 2022/0240509 A1 Aug. 4, 2022

(30) Foreign Application Priority Data

Sep. 24, 2019 (CN) ......................... 201910903214.2
Sep. 24, 2019 (CN) ......................... 201910903356.9
(Continued)

(51) Int. Cl.
*A01N 43/76* (2006.01)
*A01P 7/02* (2006.01)
(Continued)

(52) U.S. Cl.
CPC ................ *A01N 43/76* (2013.01); *A01P 7/02* (2021.08); *C07D 263/14* (2013.01); *C07D 413/10* (2013.01)

(58) Field of Classification Search
CPC ......... A01N 43/76; A01P 7/02; C07D 263/16; C07D 413/10
See application file for complete search history.

(56) References Cited

U.S. PATENT DOCUMENTS 4,843,100 A 6/1989 Nagase et al.
5,141,948 A * 8/1992 Miyamoto ............. A01N 43/74
548/239
(Continued)

FOREIGN PATENT DOCUMENTS

CN 1054422 A 9/1991
CN 1199401 A 11/1998
(Continued)

OTHER PUBLICATIONS

Suzuki et al:"Synthesis and activity of novel acaricidal/insecticidal 2,4-diphenyl-1,3-oxazolines", Nippon Noyaku Gakkaishi, vol. 27, No. 1, Jan. 1, 2002(Jan. 1, 2002), pp. 1-8.
(Continued)

*Primary Examiner* — Alicia L Otton
(74) *Attorney, Agent, or Firm* — CANTOR COLBURN LLP

(57) ABSTRACT

Disclosed are an oxazoline compound, a synthesis method therefor and an application thereof. The oxazoline compound has a structure represented by formula (I), wherein in the formula (I), R is selected from groups represented by formula (I-1), formula (I-2), and formula (I-3), where an oxazoline derivative having a novel molecular structure is obtained by introducing a nitrogen heterocycle, an ether bond or a sulfonate structure into the oxazoline compound. The oxazoline derivative is useful in the field of agricultural protection, and has higher acaricidal activity than etoxazole, can inhibit the synthesis of chitin from mites, and can effectively control the embryogenesis and development of eggs of *Tetranychus cinnabarinus*, as well as the ecdysis process from larvae to adults, and therefore has a significant effect in killing mite eggs and larvae.

formula (I)

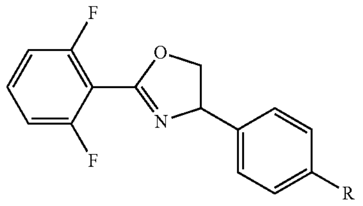

formula (I-1)

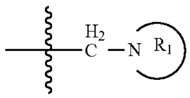

formula (I-2)

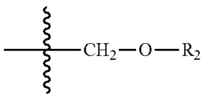

formula (I-3)

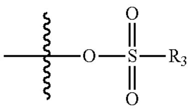

4 Claims, No Drawings

(30) Foreign Application Priority Data

Sep. 24, 2019 (CN) ......................... 201910903358.8
Sep. 24, 2019 (CN) ......................... 201910903359.2

(51) Int. Cl.
*C07D 263/14* (2006.01)
*C07D 413/10* (2006.01)

(56) References Cited

U.S. PATENT DOCUMENTS 5,478,855 A 12/1995 Suzuki et al.
5,633,271 A 5/1997 Amoo et al.

FOREIGN PATENT DOCUMENTS

CN 104910093 A 9/2015
CN 105348211 A 2/2016
EP 0645085 A1 3/1995
WO 9324470 12/1993

OTHER PUBLICATIONS

Xiuling Yu et al:"Design, Synthesis, Acaricidal/Insecticidal Activity, and Structure& ndash; Activity Relationship Studies of Novel Oxazolines Containing Sulfone/Sulfoxide Groups Based on the Sulfonylurea Receptor Protein-Binding Site", Journal of Agricultural and Food Chemistry, vol. 64, No. 15, Apr. 5, 2016(Apr. 5, 2016), pp. 3034-3040.

Anderson, Svend Olav, Biochemistry of Insect Cuticle, Ann. Rev. Entomol. 1979, 24, 24-61.

Asaka, Akiyoshi et al., Pomacea canaliculata, Jpn. J. Appl. Ent. Zool, 1987, 31(4), 339-343.

Chen, Shilin et al. Design, Synthesis, Acaricidal Activities, and Structure-Activity Relationship Studies of Novel Oxazolines Containing Sulfonate Moieties J.Agric.Food Chem.,2019, 67, 13544-13549.

Cleveland, Merrill L., Field Studies in the Control of Orchard Mites in 1957, Journal of Economic Entomology, 1958, 51(5), 713-714.

Daxiang, Wang Important Role of Heterocyclic Compounds in Developing Pesticide, Pesticides 1995,34(1):6-9.

De Oliveira, Jhones, et al., Recent Developments and Challenges for Nanoscale Formulation of Botanical Pesticides for Use in Sustainable Agriculture, J.Agric.Food.Chem., 2018, 66(34), 8898-8913.

Douris, Vassilis et al. Resistance mutation conserved between insects and mites unravels the benzoylurea insecticide mode of action on chitin biosynthesis Proc.Natl.Acad.Sci.U.SA., 2016, 113(51) : 14692-14697.

Eroglu, Ceren et al. Acaricidal effect of cell-free supernatants from *Xenorhabdus* and *Photorhabdus* bacteria against Tetranychus urticae (Acari: Tetranychidae), Journal of Invertebrate Pathology, 2019, 160, 61-66.

Grosscurt, A.C., et al., Effects of Diflubenzuron on Mechanical Penetrability, Chitin Formation, and Structure of the Elytra of Leptinotarsa Decemlineata, J. Insect. Physiol., 1978, 24, 827-831.

Jinfei, Yang et al. Research Progress of Tetrazole Heterocyclic Compounds, _ 2013,40(11):75-76.

Kavalek, Jaromir et al. Kinetics and Mechanism of Methanolysis of Benzoyl Derivatives of Substituted Phenylureas and Phenylthioureas Collect .Czech .Chem .Commun ., 1984, 49 : 2103-2110.

Li, Y.Q. ; Yang, X.L. ; Wang, Q.M.Design, synthesis, acaricidal activity, and mechanism of oxazoline derivatives containing an oxime ether moiety[J].J.Agric.Food Chem., 2014, 62(14) : 3064-3072.

Oatman, Earl R., European Red Mite Control and Population Studies on Apple in Wisconsin, Journal of Economic Entomology, 1959, 52(5), 871-877.

Stocco, Rafael et al., Stability and fitness costs associated with etoxazole resistance in Tetranychus urticae (Acari: Tetranychidae), Exp Appl Acarol, 2016, 69(4) : 413-425.

Sun, Ranfeng, et al., Design, Synthesis, and Insecticidal Evaluation of New Benzoylureas Containing Amide and Sulfonate Groups Based on the Sulfonylurea Receptor Protein Binding Site for Diflubenzuron and Glibenclamide, Journal of Agricultural and Food Chemistry, 2013, 61(3) : 517-522.

Suzuki, Junji et al. Development of a New Acaricide, Etoxazole Journal of Pesticide Science ,2001,26(2):215-223.

Van Leeuwen, Thomas et al., The economic importance of acaricides in the control of phytophagous mites and an update on recent acaricide mode of action research, Pesticide Biochemistry and Physiology, 2015, 121, 12-21.

Vitaku Edon, et al. Analysis of the Structural Diversity, Substitution Patterns, and Frequency of Nitrogen Heterocycles among U.S. FDA Approved Pharmaceuticals J.Med.Chem.2014,57(24),10257-10274.

Yang, Shuang-hua et al., Synthesis and Biological Activities of Novel Triazole Compounds Containing Ether Link, Agrochemicals 2010, 49(09), 645-647.

Ying, Li et al., Studies on Chitin Synthase Inhibitors, Progress in Chemistry, 2007, 19(4), 535-543.

Yu, X.L. ; Liu, Y.X. ; Li, Y.Q. ; et al.Design, synthesis, and acaricidal/insecticidal activities of oxazoline derivatives containing a sulfur ether moiety[J].J.Agric.Food Chem., 2015, 63(44) : 9690-9695.

Zeng, Juan et al., Analysis of the armyworm outbreak in 2012 and suggestions of monitoring and forecasting, Plant Protection, 2013, 39 : 117-121.

Zhang, Yu et al. Route Evaluation and Ritter Reaction Based Synthesis of Oxazoline Acaricide Candidates FET-II-L and NK-12 Org. Process Res. Dev.03.,2020, 24, 216-227.

Ajda Podgorsek, et al. Selective aerobic oxidative dibromination of alkenes with aqueous HBr and sodium nitrite as a catalyst. Green Chem., 2009, 11, 120-126.

Whashi, Design, synthesis and biological activity studies of 2, 4-diphenyl-1, 3-oxazoline acaricides, in Massive Data Knowledge Service Platform, 2009, pp. 81-82. (Abstract in English).

* cited by examiner

OXAZOLINE COMPOUND, SYNTHESIS METHOD THEREFOR AND APPLICATION THEREOF

CROSS REFERENCE TO RELATED APPLICATIONS

This application is a National Stage filing of PCT/CN2020/117485 filed on Sep. 24, 2020, which claims the benefits of Chinese patent application 201910903214.2 filed on Sep. 24, 2019, Chinese patent application 201910903359.2 filed on Sep. 24, 2019, Chinese patent application 201910903356.9 filed on Sep. 24, 2019, and Chinese patent application 201910903358.8 filed on Sep. 24, 2019, all of which are incorporated by reference in their entirety.

TECHNICAL FIELD

The invention relates to the field of agricultural protection, in particular to a class of oxazoline compounds and synthesis methods therefor and application thereof.

BACKGROUND

Mites are one of the main agricultural disasters, and the phytophagous mites are various in types, and have various habits and habitats and extremely strong adaptability. Since the 1970s mites have jumped to an important disaster in as many as 800 economic crops such as potatoes, wheat, fruit trees, vegetables, cotton, corn, flowers, beans, etc. (J. Invertebr. Pathol., 2019, 160, 61-66.).

Etoxazole (Structural formula one), a type of growth regulating inhibitory acaricide belonging to 2,4-diphenyl-1,3-oxazoline chemical family, is developed by Yashima Chemical Industry Co., Ltd. (now Kyoyu Agri Co. Ltd.), Japan in 1994, and successfully marketed in 1998, as the only oxazoline compound commercially available to date (*Proc. Brighton Crop Protect Conf-Pests Dis.,* 1994, 3: 37-44.). It can kill mites and insects by inhibiting the synthesis of chitin only existing in the cell wall of fungi and the epidermis of insects. The research on the oxazoline compounds to which etoxazole belongs is always a research hotspot.

Structural formula one

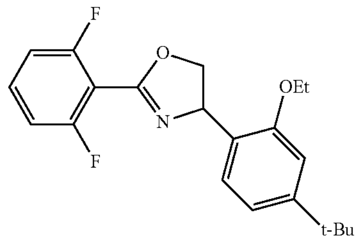

However, there are two main methods for synthesizing oxazoline compounds, an aminoethanol method and a chloroacetaldehyde dimethyl acetal method. In 1995, Suzuki et al first reported the synthesis of etoxazole by the aminoethanol method (U.S. Pat. No. 5,478,855 [P], 1995-12-26.).

In 2001, Suzuki et al also reported the synthesis of etoxazole by the chloroacetaldehyde dimethyl acetal method (*J. Pestic. Sci.,* 2001, 26(2): 215-223).

However, the two methods have long synthesis steps and uneconomical raw materials, so that the synthesis research and agricultural application of the oxazoline compounds are greatly limited. Therefore, the development of a class of novel oxazoline structure with high acaricidal activity and novel synthesis methods therefor are urgently needed.

DISCLOSURE OF INVENTION

One of the objects of the present invention is to provide a novel class of oxazoline compounds having a good control effect on mites, particularly phytophagous mites.

The invention also aims to overcome the defects of long synthesis steps and uneconomical raw materials of the oxazoline compounds in the prior art.

In order to achieve the above object, a first aspect of the present invention provides a class of oxazoline compounds, which has a structure represented by formula (I), formula (I)

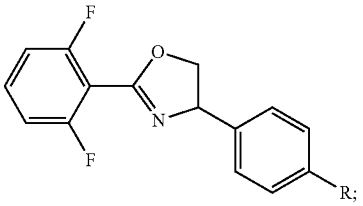

formula (I-1)

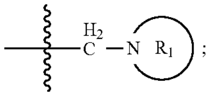

formula (I-2)

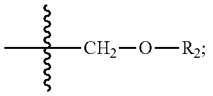

formula (I-3)

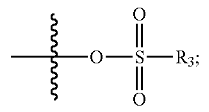

wherein, in the formula (I), R is selected from a group shown in formula (I-1), formula (I-2) and formula (I-3);

in the formula (I-1), the nitrogen-containing heterocyclic ring represented by $R_1$ is selected from substituted or unsubstituted five-membered to ten-membered single heterocyclic group, substituted or unsubstituted eight-membered to twelve-membered condensed bicyclic group, and the substituents optionally present on $R_1$ are each independently selected from at least one of halogen, $C_{1-10}$ alkyl, $C_{1-10}$ alkoxy, $C_{2-10}$ acyl;

in the formula (I-2), $R_2$ is selected from any one of substituted or unsubstituted $C_{1-10}$ alkyl, substituted or unsubstituted five-membered to eight-membered single heterocyclic group, substituted or unsubstituted $C_{2-8}$ alkenyl, substituted or unsubstituted $C_{2-8}$ alkynyl, substituted or unsubstituted phenyl, substituted or unsubstituted naphthyl; the optional substituent on $R_2$ is at least one of halogen, $C_{1-8}$ alkyl, $C_{1-8}$ alkyl substituted by 1-6 halogens, tetrahydrofuryl, furyl, thienyl and phenyl;

in the formula (I-3), $R_3$ is selected from any one of $C_{1-10}$ alkyl, $C_{2-6}$ alkenyl, substituted or unsubstituted phenyl and naphthyl, the optional substituent groups on $R_3$ are independently selected from at least one of halogen, $C_{1-8}$ alkyl, $C_{1-8}$ alkyl substituted by 1-6 halogen, nitro, cyano and $C_{2-8}$ amido, or when $R_3$ is substituted phenyl, two adjacent substituents on the phenyl are cyclized together to form a six-membered heterocyclic ring containing 1-3 heteroatoms selected from O and/or N.

A second aspect of the present invention provides a method for preparing the oxazoline compounds, which comprises:

carrying out a first contact reaction on the compound shown in the formula (II-1) or the compound shown in the formula (II-2) with an $R_{11}$ group donor;

formula (II-1)

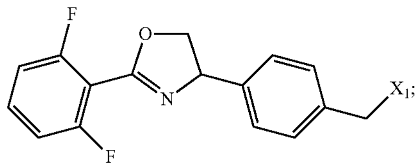

formula (II-2)

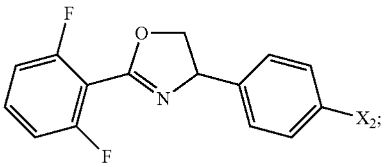

formula (II-3)

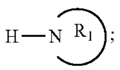

formula (II-4)

HO—$R_2$;

formula (II-5)

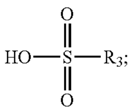

$X_1$ and $X_2$ in formula (II-1) and formula (II-2) are each independently selected from halogen and hydroxy;

the $R_{11}$ group donor is selected from at least one of compounds shown in formula (II-3), formula (II-4) and formula (II-5);

in the formulae (II-3), (II-4) and (II-5), $R_1$, $R_2$ and $R_3$ are as defined above.

A third aspect of the present invention provides a method for preparing an oxazoline compound, comprising:

carrying out a second contact reaction on a compound shown in formula (III-1) and a compound shown in formula (III-2) or a compound shown in formula (III-3) to obtain a compound shown in the formula (III-4) or a compound shown in the formula (III-5);

formula (III-1)

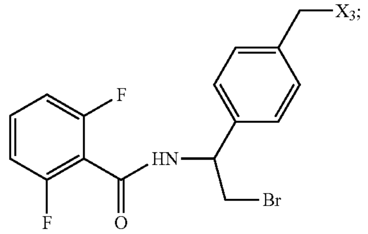

-continued formula (III-2)

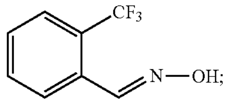

formula (III-3)

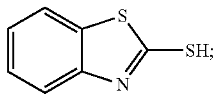

formula (III-4)

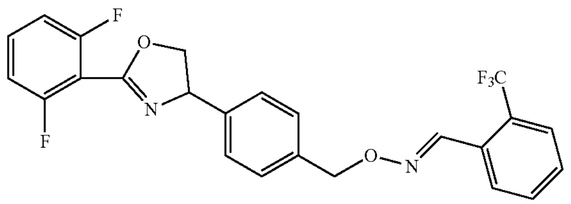

formula (III-5)

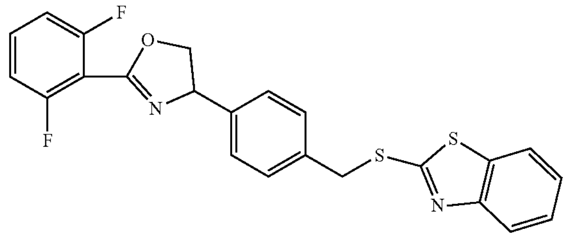

Wherein $X_3$ in formula (III-1) is selected from halogen.

The oxazoline derivatives with a novel molecular structure are obtained by introducing a nitrogen heterocycle, an ether or a sulfonic acid ester structure into an oxazoline compound, and the novel oxazoline derivatives have higher acaricidal activity than etoxazole, can inhibit the synthesis of chitin of mites, can effectively prevent and control the embryo formation and development of *Tetranychus cinnabarinus* eggs, and have remarkable acaricidal effect on mite eggs and larvae in the molting process from larval mites to adult mites.

The invention takes commercialized reagents of p-chloromethyl styrene, NBS (N-bromosuccinimide) and 2,6-difluorobenzonitrile as initial raw materials, realizes the preparation of the compound shown in the formula (III-4) and the compound shown in the formula (III-5) which are high-efficiency acaricidal candidate varieties through two steps with a total yield of 75%, achieves breakthrough progress compared with the existing routes, and lays a foundation for the further development of the two compounds.

DETAILED DESCRIPTION

The endpoints of the ranges and any values disclosed herein are not limited to the precise range or value, and these ranges or values should be understood to encompass values close to these ranges or values. For numerical ranges, each range between its endpoints and individual point values, and each individual point value can be combined with each other to give one or more new numerical ranges, and such numerical ranges should be construed as specifically disclosed herein.

As described above, the first aspect of the present invention provides a class of oxazoline compounds.

The "substituted or unsubstituted five-membered to ten-membered heteromonocyclic group" refers to a heteromonocyclic group wherein 5 to 10 atoms form a ring, and at least one hetero atom such as N, O or S is contained in the atoms forming the ring, and any position on the heteromonocyclic group which may be substituted with a substituent as defined above. The definition of the "substituted or unsubstituted five-membered to eight-membered heteromonocyclic group" is similar to that of the "substituted or unsubstituted five-membered to ten-membered heteromonocyclic group", except that the number of atoms forming the heteromonocyclic group is different, and the present invention will not be described again, and those skilled in the art will not be construed as limiting the present invention. Likewise, the "substituted or unsubstituted five-membered to eight-membered nitrogen-containing heteromonocyclic group" has a similar definition to the "substituted or unsubstituted five-membered to ten-membered heteromonocyclic group" except that the "substituted or unsubstituted five-membered to eight-membered nitrogen-containing heteromonocyclic group" has at least one N atom in the ring-forming atoms. The "substituted or unsubstituted five-membered to six-membered heteromonocyclic group containing any one heteroatom of nitrogen, oxygen and sulfur" has a similar definition to that of the "substituted or unsubstituted five-membered to ten-membered heteromonocyclic group" except that at least one atom selected from nitrogen, oxygen and sulfur in the "substituted or unsubstituted five-membered to six-membered heteromonocyclic group containing any one heteroatom of nitrogen, oxygen and sulfur" is used as a ring-forming atom. The "five-membered to eight-membered nitrogen-containing saturated heteromonocyclic group" has a similar definition to the "five-membered to ten-membered heteromonocyclic group" except that the ring in the "five-membered to eight-membered nitrogen-containing saturated heteromonocyclic group" is a saturated monocyclic ring in which at least one N atom is used as a ring-forming atom.

The "substituted or unsubstituted eight-membered to twelve-membered fused bicyclic group" means a fused bicyclic group in which two rings are composed of 8 to 12 atoms and a common ring edge is present in both rings, and any position on the fused bicyclic group which may be substituted by a substituent defined accordingly. The "substituted or unsubstituted eight-membered to ten-membered nitrogen-containing benzo-fused bicyclic group" has a similar definition as the "substituted or unsubstituted eight-membered to ten-membered fused bicyclic group", except that at least one ring of the "substituted or unsubstituted eight-membered to ten-membered nitrogen-containing benzo-fused bicyclic group" is a benzene ring, and the other ring is a N atom-containing heterocyclic ring.

The "$C_{1-10}$ alkyl" means a straight-chain alkyl group, a branched-chain alkyl group or a cyclic alkyl group having 1 to 10 carbon atoms, and exemplarily, the "$C_{1-10}$ alkyl" may be a methyl group, an ethyl group, a n-propyl group, an isopropyl group, a n-butyl group, an isobutyl group, a tert-butyl group, a n-pentyl group, an isopentyl group, a n-hexyl group, a cyclopropyl group, a methylcyclopropyl group, an ethylcyclopropyl group, a cyclopentyl group, a methylcyclopentyl group, a cyclohexyl group, or the like. Also, the definition of "$C_{1-n}$ alkyl" according to the present invention is similar to that of "$C_{1-10}$ alkyl" except that the total number of carbon atoms is different, and thus, the present invention will not be described in detail with reference to the following specific definition of "$C_{1-n}$ alkyl" and those skilled in the art will not be construed as limiting the present invention, where n is an integer greater than 1 and less than 10.

The "$C_{1-10}$ alkoxy" means a linear alkoxy group, a branched alkoxy group or a cycloalkoxy group having 1 to 10 carbon atoms, and exemplarily, the "$C_{1-10}$ alkoxy" may be a methoxy group, an ethoxy group, a n-propoxy group, an isopropoxy group, a n-butoxy group, an isobutoxy group, a tert-butoxy group, a n-pentoxy group, an isopentoxy group, a n-hexoxy group, a cyclopropoxy group, a methylcyclopropoxy group, an ethylcyclopropoxy group, a cyclopentoxy group, a methylcyclopentoxy group, a cyclohexyloxy group or the like. Also, the definition of "$C_{1-n}$ alkoxy" according to the present invention is similar to the definition of "$C_{1-10}$ alkoxy" except that the total number of carbon atoms is different, and thus, the present invention will not be described in detail with respect to the specific definition of "$C_{1-n}$ alkoxy" hereinafter, and those skilled in the art will not be construed as limiting the present invention, wherein n is an integer greater than 1 and less than 10.

The "$C_{2-10}$ acyl" refers to acyl groups having a total number of carbon atoms of 2-10, and the formula may be, for example, an —NHCO—$C_{1-9}$ alkyl. Also, the definition of "$C_{2-n}$ acyl" according to the present invention is similar to the definition of "$C_{2-10}$ acyl" except that the total number of carbon atoms is different, and thus, the present invention will not be described in detail with reference to the following specific definition of "$C_{2-n}$ acyl" and those skilled in the art will not be construed as limiting the present invention, where n is an integer of more than 2 and less than 10.

The "substituted or unsubstituted $C_{2-8}$ alkenyl" means a straight chain alkenyl group, a branched alkenyl group having 2 to 8 carbon atoms in total, and any substitutable position on the $C_{2-8}$ alkenyl may be substituted by a substituent defined accordingly, and exemplarily, the $C_{2-8}$ alkenyl may be an ethenyl group, a propenyl group, a butenyl group, and the like. Also, the definition of "$C_{2-n}$ alkenyl" according to the present invention is similar to that of "$C_{2-8}$ alkenyl" except that the total number of carbon atoms is different, and thus, the present invention will not be described in detail with reference to the following specific definition of "$C_{2-n}$ alkenyl" and those skilled in the art will not be construed as limiting the present invention, where n is an integer greater than 2 and less than 8.

The "substituted or unsubstituted $C_{2-8}$ alkynyl" means a straight chain alkynyl group, a branched chain alkynyl group with a total number of carbon atoms of 2-8, and any substitutable position on the $C_{2-8}$ alkynyl can be substituted by a substituent defined accordingly, and exemplarily, the $C_{2-8}$ alkynyl may be an ethynyl group, propynyl group, butynyl group, etc. Also, the definition of "$C_{2-n}$ alkynyl" according to the present invention is similar to that of "$C_{2-8}$ alkynyl" except that the total number of carbon atoms is different, and thus, the present invention will not be described in detail with reference to the following specific definition of "$C_{2-n}$ alkynyl" and those skilled in the art will not be construed as limiting the present invention, where n is an integer greater than 2 and less than 8.

The "$C_{1-8}$ alkyl substituted by 1-6 halogens" means a straight-chain alkyl group, a branched alkyl group having a total number of carbon atoms of 1 to 8, and any substitutable position in the $C_{1-8}$ alkyl may be substituted with 1 to 6 halogens, and exemplarily, the "$C_{1-8}$ alkyl group substituted by 1-6 halogens" may be a trifluoromethyl group, a difluoromethyl group, a monofluoromethyl group, a monofluoroethyl group, a difluoroethyl group, a trifluoroethyl group, or the like. Also, the definition of "$C_{1-n}$ alkyl substituted by 1-n halogens" according to the present invention is similar to the definition of "$C_{1-8}$ alkyl substituted by 1-6 halogens" except that the total number of carbon atoms and/or the number of halogen substituents are different, and thus, the present invention will not be described in detail with reference to the following specific definition of "$C_{1-n}$ alkyl substituted by 1-n halogens", which is not to be construed as a limitation of the present invention by those skilled in the art, and n is an integer greater than 1 and less than 8.

The expression "the optional substituent groups on $R_1$ are independently selected from at least one of halogen, $C_{1-10}$ alkyl, $C_{1-10}$ alkoxy and $C_{2-10}$ acyl" means that when a substituent is present on the nitrogen-containing heterocycle represented by $R_1$, the substituent may be selected from halogen, $C_{1-10}$ alkyl, $C_{1-10}$ alkoxy and $C_{2-10}$ acyl. The definition of "the optional substituent groups on $R_2$ are independently selected from at least one of halogen, $C_{1-8}$ alkyl, $C_{1-8}$ alkyl substituted by 1-6 halogens, tetrahydrofuryl, furyl, thienyl and phenyl" and the definition of "the optional substituent groups on $R_3$ are independently selected from at least one of halogen, $C_{1-8}$ alkyl, $C_{1-8}$ alkyl substituted by 1-6 halogens, nitro, cyano and $C_{2-8}$ acylamino" are similar to the definition of "the optional substituent groups on $R_1$ are independently selected from at least one of halogen, $C_{1-10}$ alkyl, $C_{1-10}$ alkoxy and $C_{2-10}$ acyl".

The "halogen" represents at least one of fluorine, chlorine, bromine and iodine.

According to a preferred embodiment:

in the formula (I-1), the nitrogen-containing heterocyclic ring represented by $R_1$ is selected from any one of a substituted or unsubstituted five-membered to eight-membered nitrogen-containing monocyclic group, a substituted or unsubstituted eight-membered to ten-membered nitrogen-containing benzo-fused bicyclic group; the substituents on $R_1$ are independently selected from at least one of halogen, $C_{1-6}$ alkyl, $C_{1-6}$ alkoxy and $C_{2-6}$ acyl;

in the formula (I-2), $R_2$ is selected from any one of substituted or unsubstituted $C_{1-6}$ alkyl, substituted or unsubstituted five-membered to six-membered single heterocyclic group containing any heteroatom of nitrogen, oxygen and sulfur, substituted or unsubstituted $C_{2-6}$ alkenyl, substituted or unsubstituted $C_{2-6}$ alkynyl, substituted or unsubstituted phenyl and naphthyl; the optional substituent on $R_2$ is at least one selected from halogen, $C_{1-6}$ alkyl, $C_{1-6}$ alkyl substituted by 1-6 halogens, tetrahydrofuryl, furyl, thienyl and phenyl;

in the formula (I-3), $R_3$ is selected from any one of $C_{1-6}$ alkyl, $C_{2-4}$ alkenyl, substituted or unsubstituted phenyl and naphthyl; the optional substituents on $R_3$ are independently selected from at least one of halogen, $C_{1-6}$ alkyl, $C_{1-6}$ alkyl substituted by 1-6 halogens, nitro, cyano and $C_{2-6}$ amide, or when $R_3$ is substituted phenyl, two adjacent substituents on the phenyl are cyclized together to form a six-membered heterocyclic ring containing 1-3 heteroatoms selected from O and/or N.

According to another preferred embodiment:

R is a group shown in a formula (I-1), wherein $R_1$ in the formula (I-1) represents a nitrogen-containing heterocyclic ring selected from any one of morpholinyl, five-membered to eight-membered nitrogen-containing saturated monocyclic heterocyclic group, pyrrolyl, dihydropyrrolyl, 2-pyrrolidinonyl, $R^1$-substituted 2-imidazolidinonyl, succinimidyl, phthalimidyl, imidazolyl, pyrazolyl, tetrahydroisoquinolinyl, indolinyl and unsubstituted or $R^1$-substituted indolyl;

each $R^1$ is independently selected from at least one of halogen, $C_{1-3}$ alkyl, methoxy and acetyl.

According to a further preferred embodiment:

the oxazoline compound is selected from any one of the following compounds:

R1-1

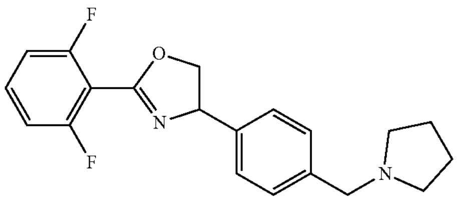

,

R1-2

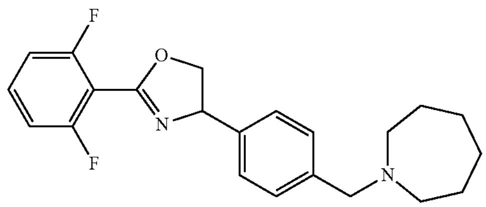

R1-3

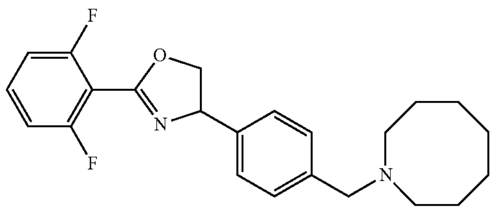

,

R1-4

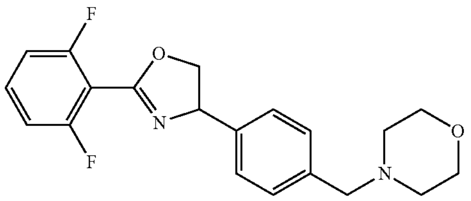

R1-5

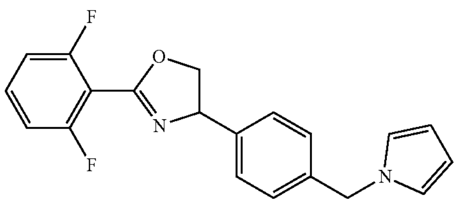

,

R1-6

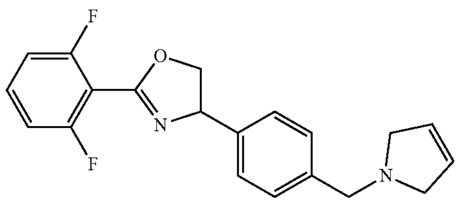

R1-7

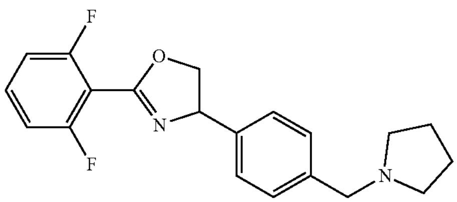

,

-continued
R1-8
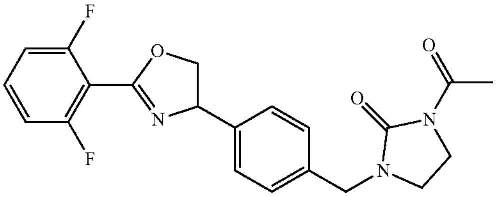
R1-9
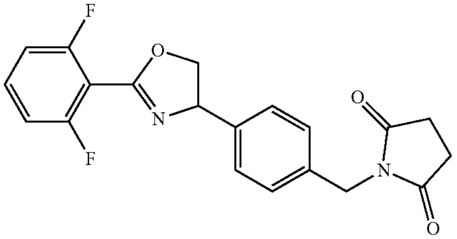
,
R1-10
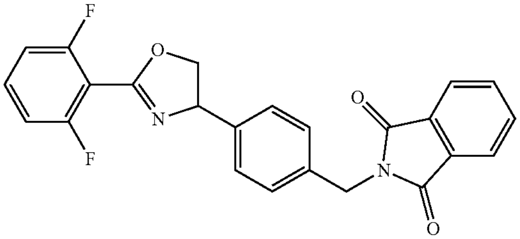
R1-11
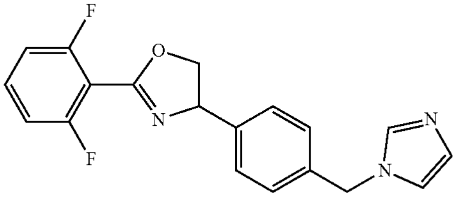
,
R1-12
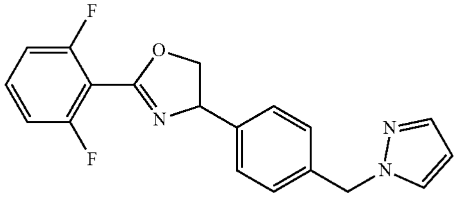
R1-13
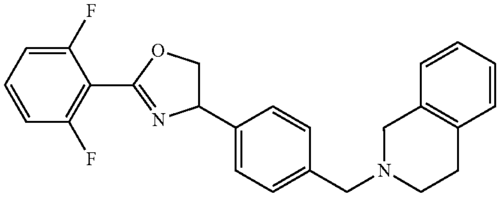
,
R1-14
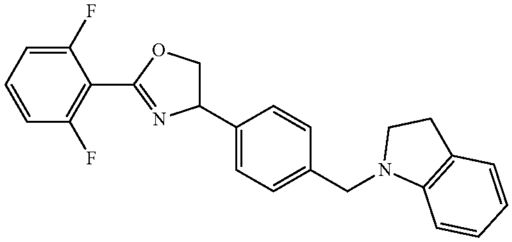
-continued
R1-15
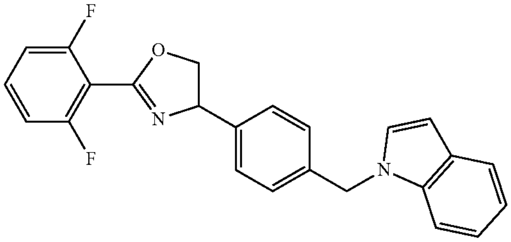
,
R1-16
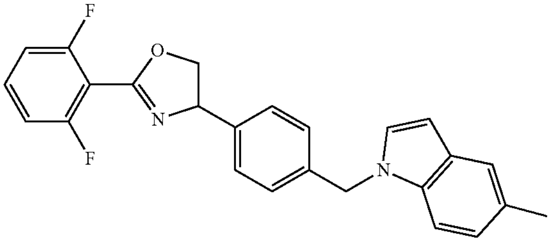
R1-17
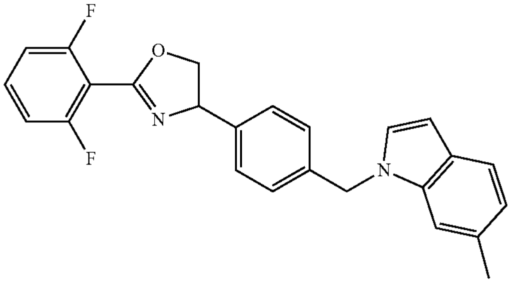
,
R1-18
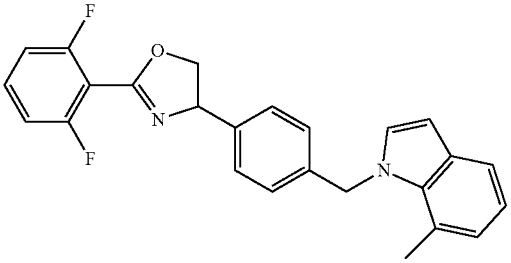
R1-19
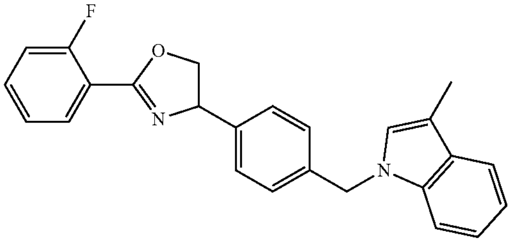
, -continued

R1-20

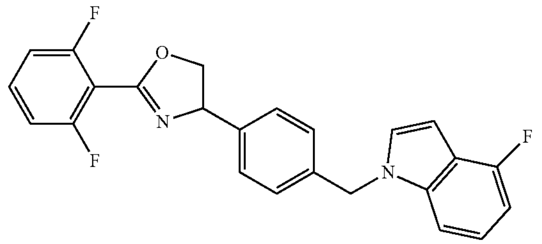

R1-21

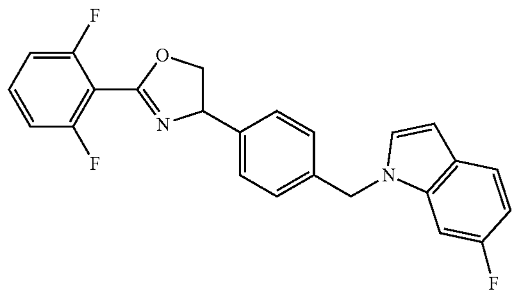

,

R1-22

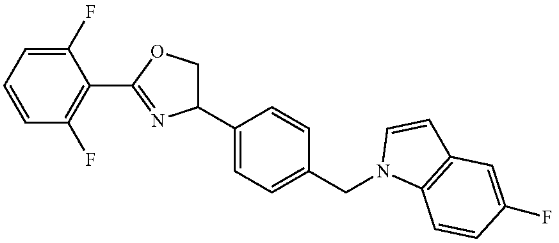

R1-23

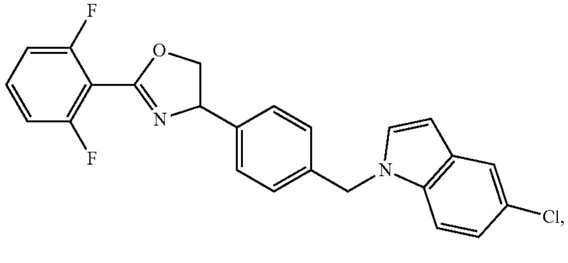

R1-24

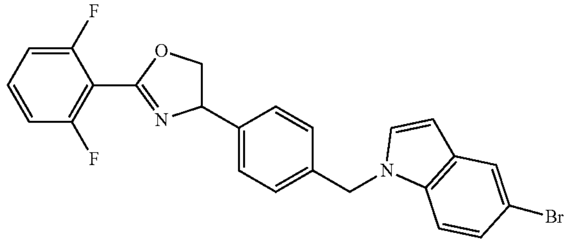

-continued

R1-25

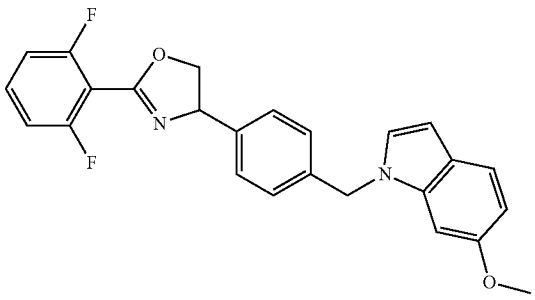

.

According to a further preferred embodiment:

R is a group represented by the formula (I-2); $R_2$ in the formula (I-2) is selected from any one of substituted or unsubstituted $C_{1-3}$ alkyl, substituted or unsubstituted $C_{2-4}$ alkenyl, naphthyl, substituted or unsubstituted $C_{2-4}$ alkynyl, substituted or unsubstituted pyridyl, pyrimidyl and $R^2$-substituted phenyl;

the optional substituent in $R_2$ and the $R^2$ are independently at least one of halogen, $C_{1-3}$ alkyl, $C_{1-3}$ alkyl substituted by 1-3 halogens, tetrahydrofuryl, furyl, thienyl and phenyl.

According to a further preferred embodiment:

the oxazoline compound is selected from any one of the following compounds,

R2-1

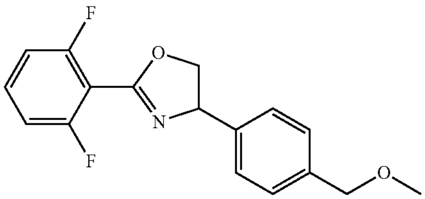

,

R2-2

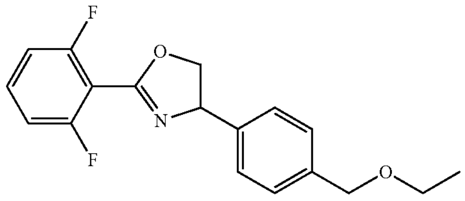

R2-3

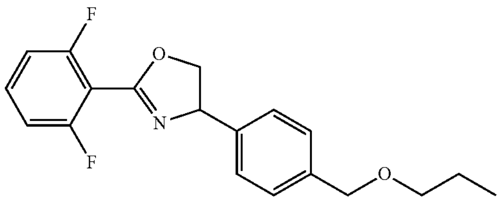

,

R2-4

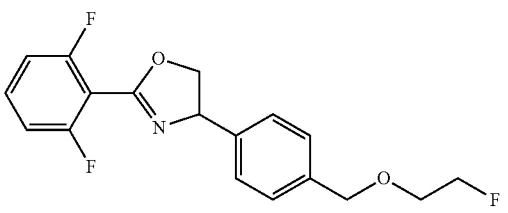

-continued
R2-5
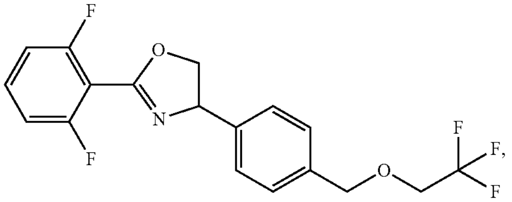
R2-6
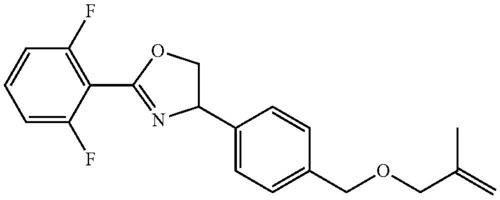
R2-7
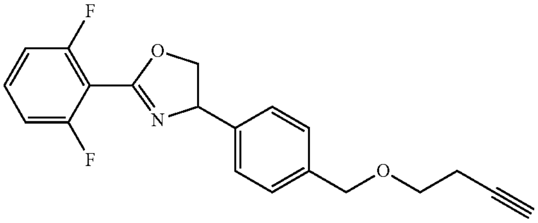
,
R2-8
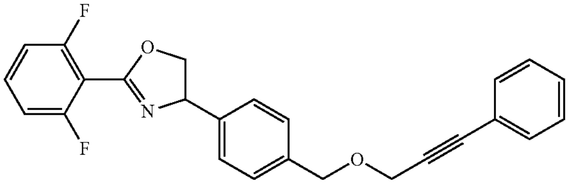
R2-9
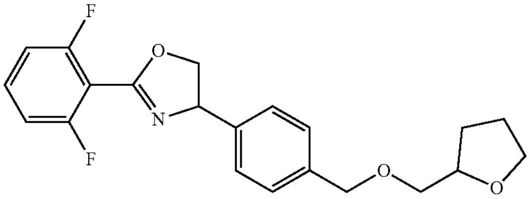
,
R2-10
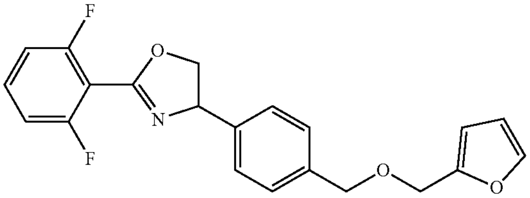
R2-11
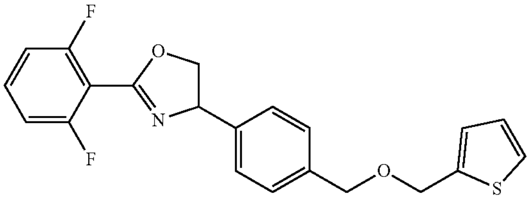
,
-continued
R2-12
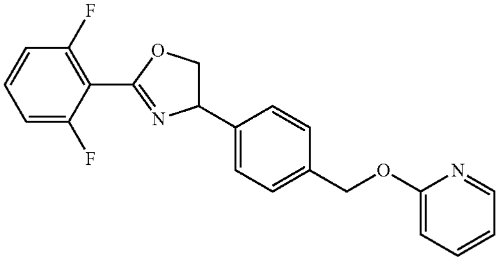
R2-13
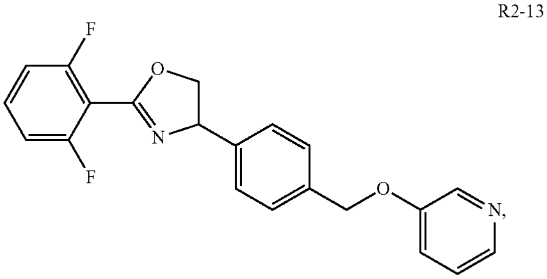
R2-14
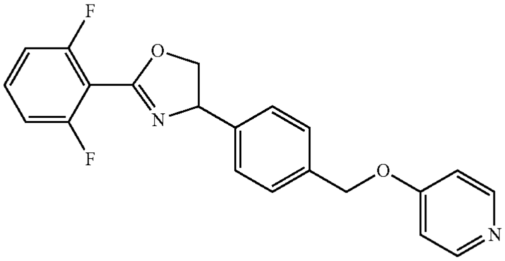
R2-15
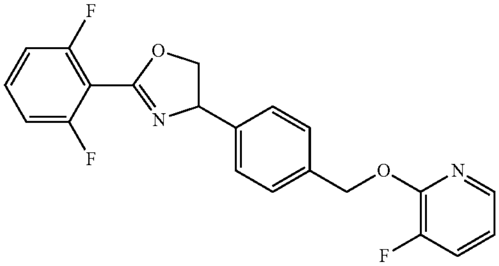
,
R2-16
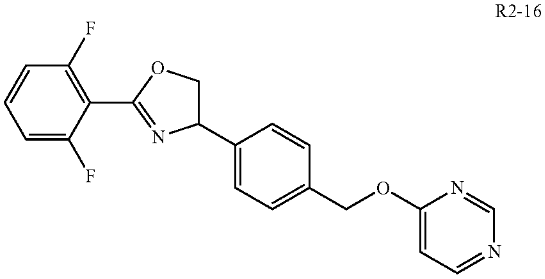

-continued

R2-17

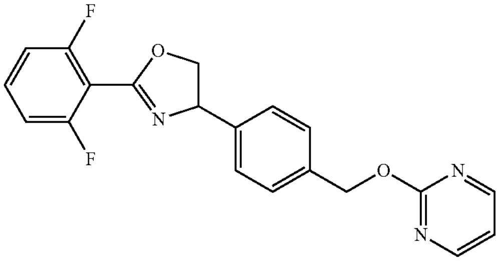

,

R2-18

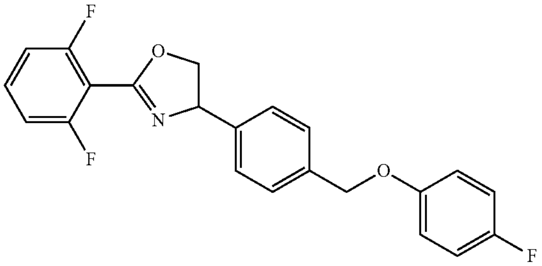

R2-19

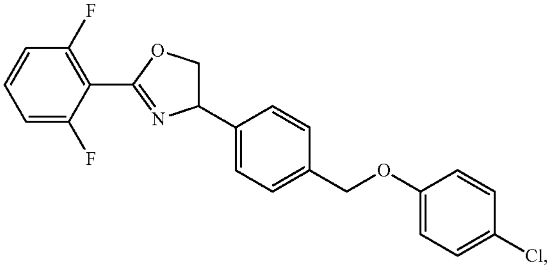

R2-20

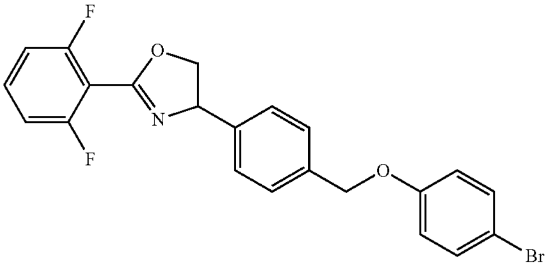

R2-21

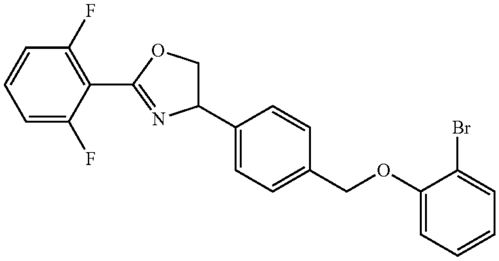

,

-continued

R2-22

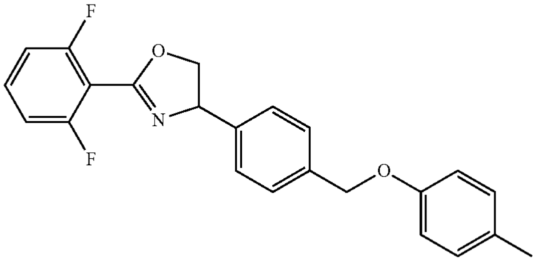

R2-23

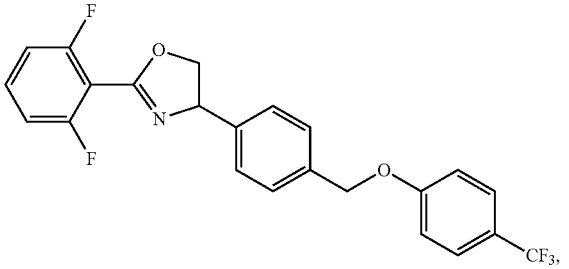

R2-24

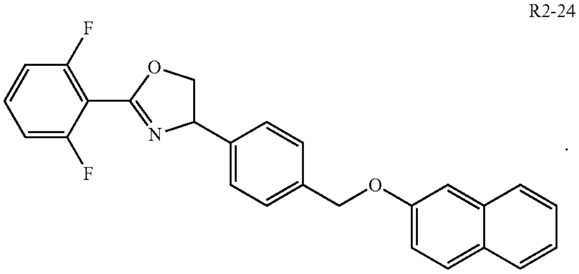 [SMILES: Fc1cccc(F)c1C1=NC(c2ccc(COc3ccc4ccccc4c3)cc2)CO1]

.

According to a further preferred embodiment:

R is a group shown in a formula (I-3), $R_3$ in the formula (I-3) is selected from any one of $C_{1-3}$ alkyl, vinyl, $C_{1-3}$ alkyl substituted by 1-3 halogens, naphthyl and $R^3$-substituted phenyl;

$R^3$ is selected from at least one of halogen, $C_{1-4}$ alkyl, $C_{1-3}$ alkyl substituted by 1-3 halogens, nitro, cyano and acetamido, or two adjacent $R^3$ on phenyl are cyclized together to form a six-membered heterocyclic ring containing 1-3 heteroatoms selected from O and/or N.

According to a further preferred embodiment:

the oxazoline compound is selected from any one of the following compounds:

R3-1

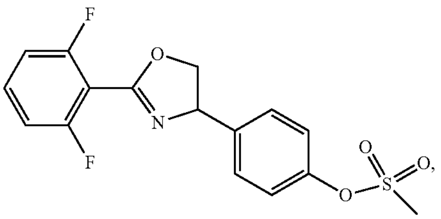

-continued
R3-2
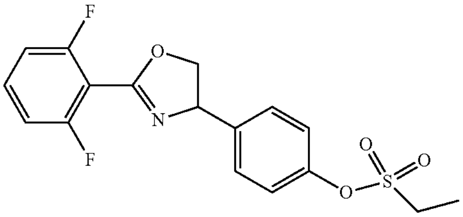
R3-3
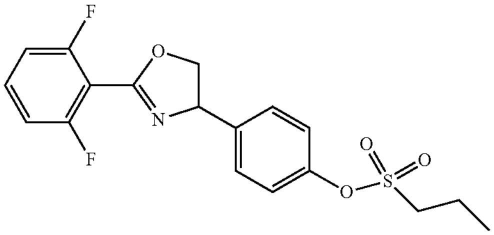
,
R3-4
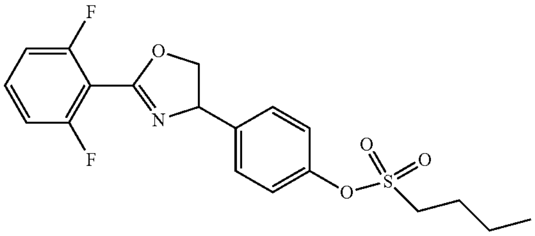
R3-5
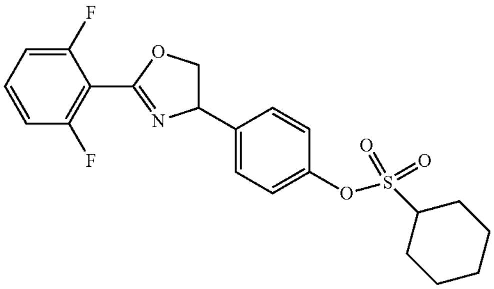
,
R3-6
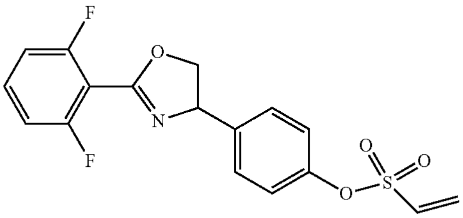
R3-7
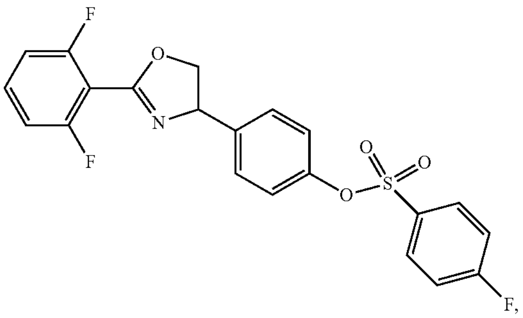
-continued
R3-8
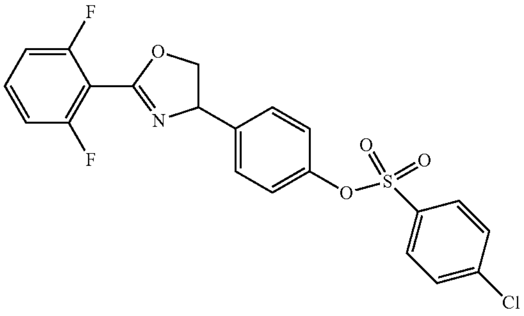
R3-9
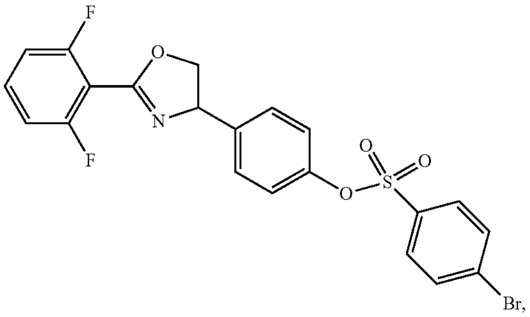
R3-10
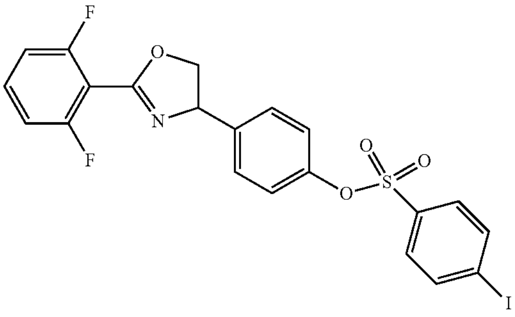
R3-11
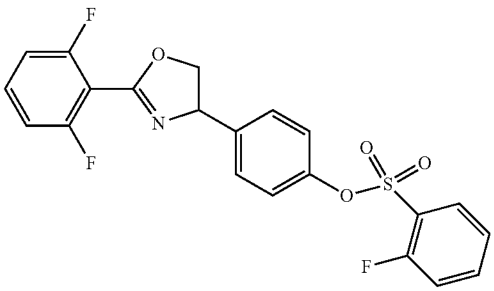
, -continued
R3-12
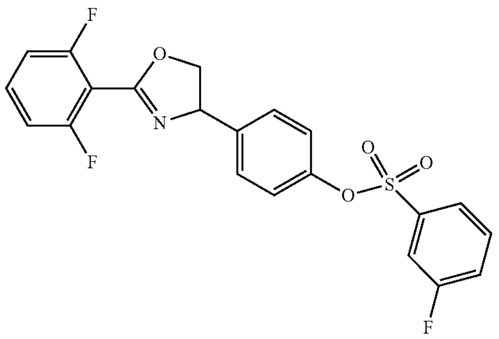
R3-13
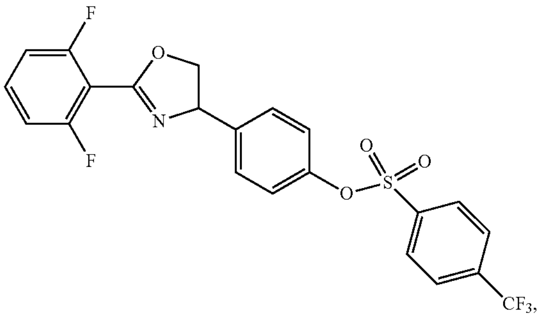
R3-14
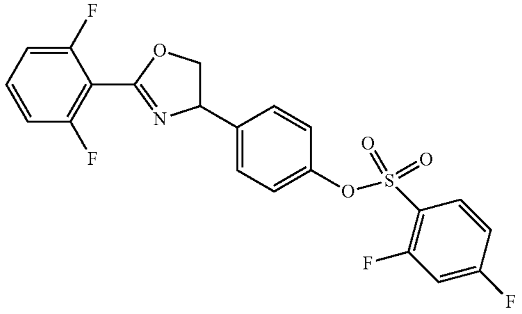
R3-15
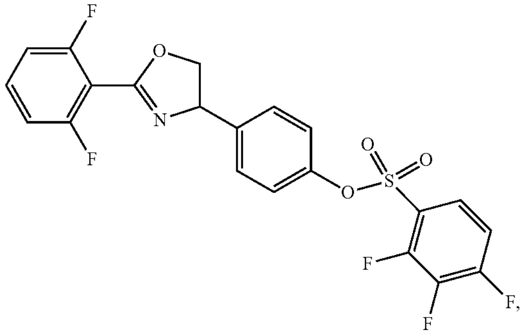
-continued
R3-16
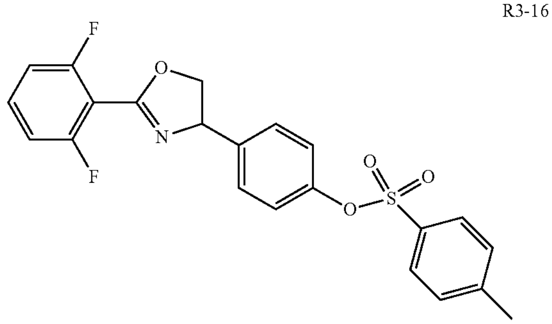
R3-17
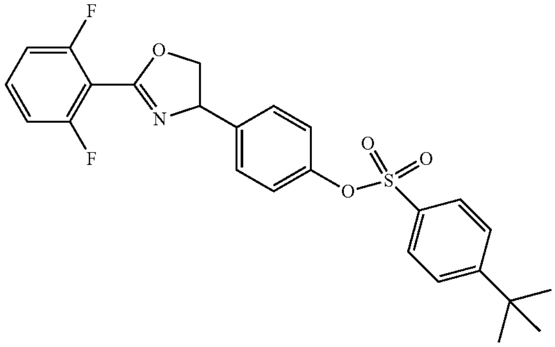
,
R3-18
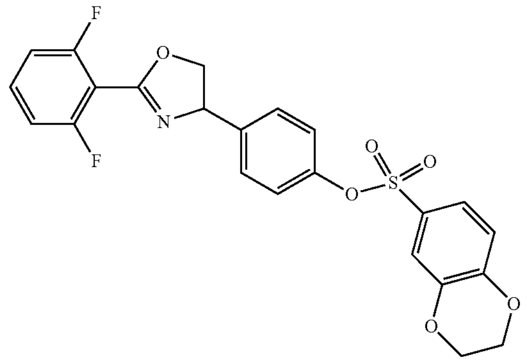
R3-19
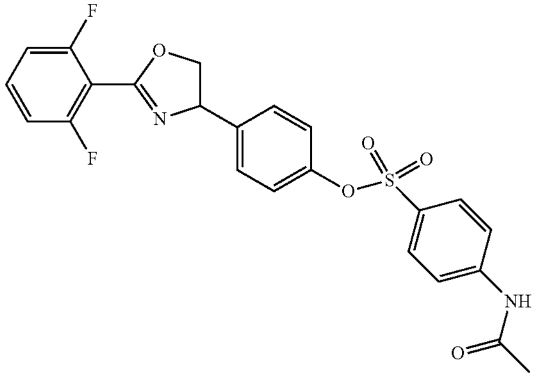
, -continued

R3-20

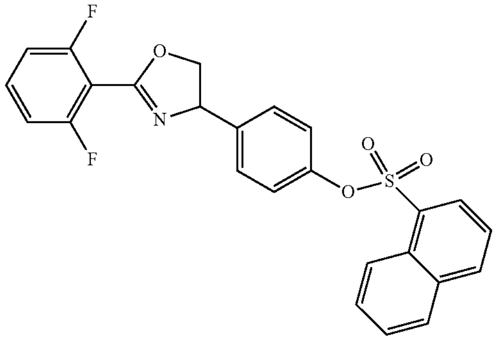

R3-21

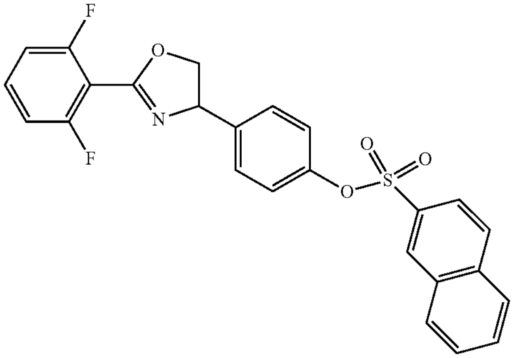

,

R3-22

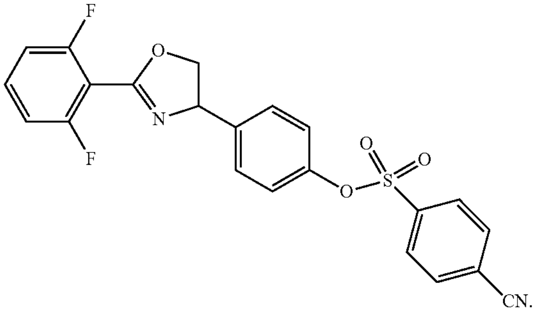

The present invention is not particularly limited to specific methods for preparing the aforementioned compounds, and those skilled in the art can prepare all the compounds of the present invention by combining synthetic methods known in the art of organic synthesis and specific preparation methods provided in the examples of the present invention hereinafter, which are not described in detail herein, and the present invention should not be construed as being limited thereto.

However, in order to obtain higher product yield and product purity, and to obtain the compound of the present invention more simply, as described above, the second aspect of the present invention provides a method for preparing the above oxazoline compound.

In the present invention, $X_1$ in formula (II-1) is preferably a Cl element.

In the present invention, $X_2$ in formula (II-2) is preferably a hydroxyl.

Preferably, the conditions of the first contact reaction at least satisfy: the temperature is above 0° C.

Preferably, the $R_{11}$ group donor is of formula (II-3); the method for synthesizing the compound comprises the following preferred embodiments:

Embodiment Mode 1 carrying out Ritter reaction on 2,6-difluorobenzonitrile, 4-vinylbenzyl chloride and NBS under the action of concentrated $H_2SO_4$ to obtain an amide intermediate, carrying out ring closure on the amide intermediate under the action of sodium hydroxide to obtain an oxazoline intermediate,

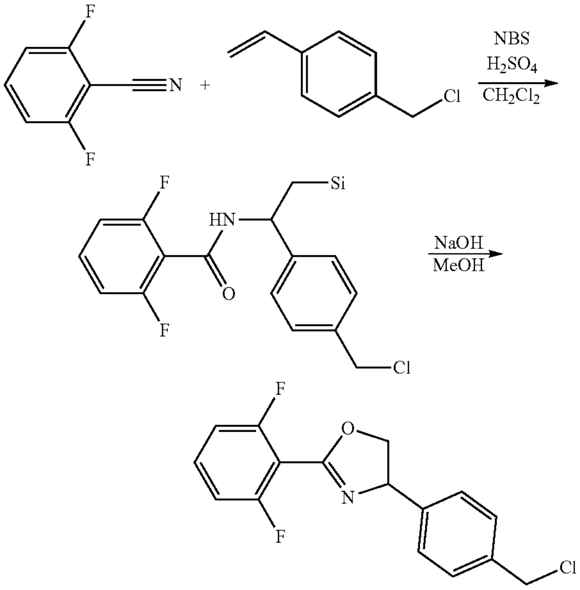

Embodiment Mode 2 the oxazoline intermediate reacts with nitrogen heterocycle in acetonitrile solvent under the action of sodium hydroxide and potassium iodide,

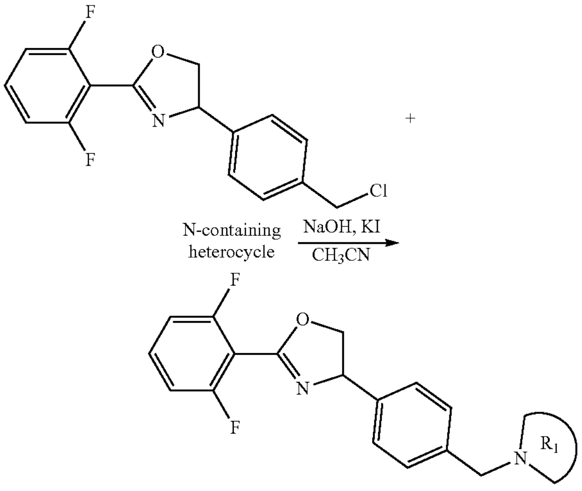

Embodiment Mode 3 the oxazoline intermediate reacts with nitrogen heterocycle in acetonitrile solvent under the action of potassium carbonate and cuprous oxide,

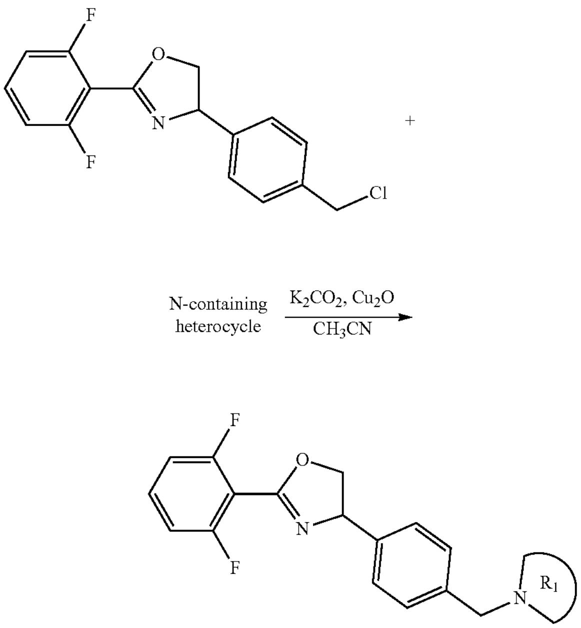

Embodiment Mode 4 the oxazoline intermediate reacts with nitrogen heterocycle in DMF solvent under the action of sodium hydride,

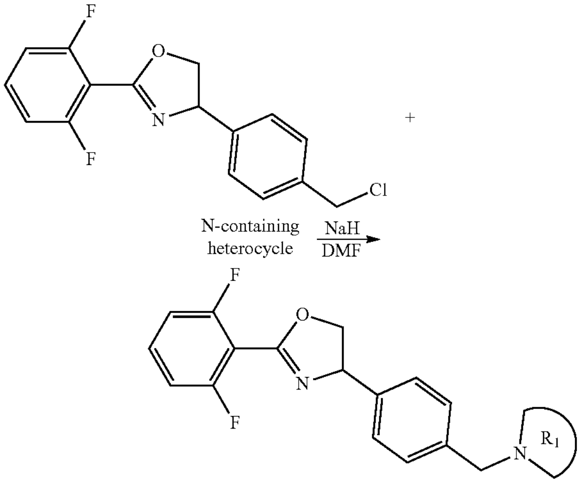

Embodiment Mode 5 the oxazoline intermediate reacts with nitrogen heterocycle in toluene solvent under the action of sodium hydroxide and TBAB (tetrabutylammonium bromide),

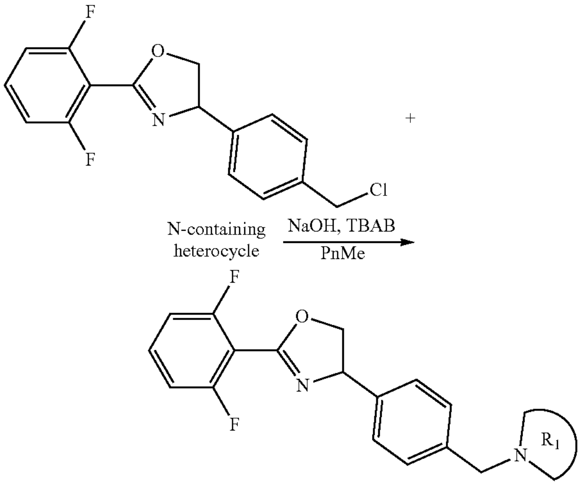

preferably, the $R_{11}$ group donor is of formula (II-4); the method for synthesizing the compound comprises the following preferred embodiments:

Embodiment Mode 1

(preferably in the presence of a halogenated hydrocarbon solvent) carrying out Ritter reaction on 2,6-difluorobenzonitrile, 4-vinylbenzyl chloride and NBS under the action of concentrated $H_2SO_4$ (preferably at the temperature of 0-40° C.) to obtain an amide intermediate C, and carrying out ring closing on the amide intermediate C under the action of sodium hydroxide to obtain an oxazoline intermediate; preferably, the molar ratio of 4-vinylbenzyl chloride to 2,6-difluorobenzonitrile is from 1:1 to 1:2; preferably, the molar ratio of 4-vinylbenzyl chloride to NBS is from 1:1 to 1:2; preferably, the reaction concentration of the 4-vinylbenzyl chloride is 0.08 mol/L to 0.8 mol/L; more preferably, the solvent is selected from at least one of dichloromethane, chloroform and carbon tetrachloride;

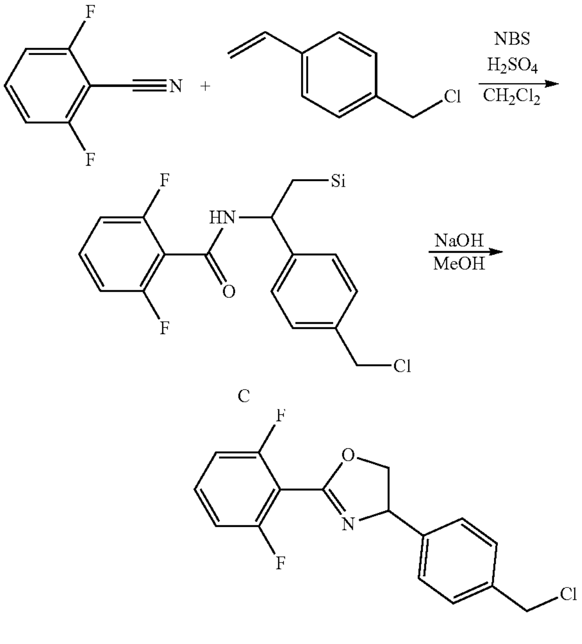

Embodiment Mode 2 the oxazoline intermediate reacts with sodium alkoxide in tetrahydrofuran solvent,

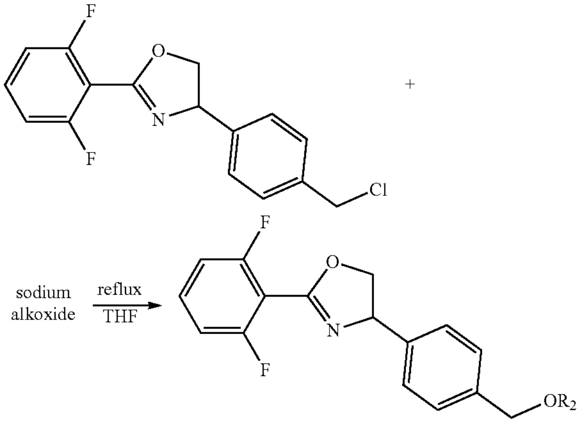

Embodiment Mode 3 reacting the oxazoline intermediate with alcohol in an acetonitrile solvent under the action of sodium hydroxide and potassium iodide; preferably, the molar ratio of the oxazoline intermediate to the sodium hydroxide is 1:1-1:2, and the concentration of the oxazoline intermediate is preferably 0.1 mol/L-1 mol/L;

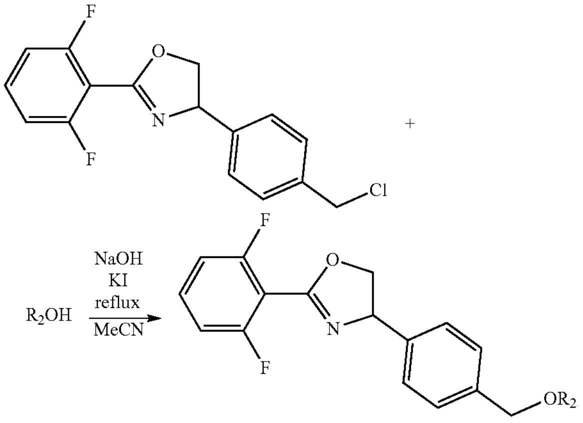

Embodiment Mode 4 the oxazoline intermediate reacts with alcohol in acetonitrile solvent under the action of potassium carbonate and potassium iodide,

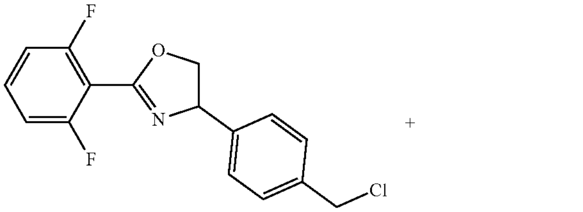

-continued

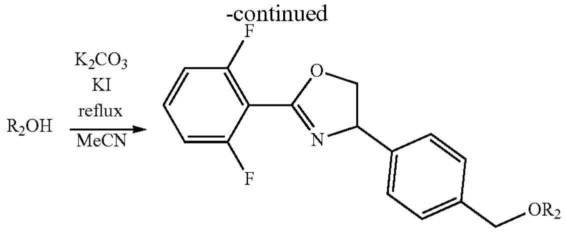

preferably, the $R_{11}$ group donor is of formula (II-5); the method for synthesizing the compound comprises the following preferred embodiments:

Embodiment Mode 1

2,6-difluorobenzamide and chloroacetaldehyde dimethyl acetal are subjected to Friedel-Crafts reaction to obtain an intermediate under the action of concentrated $H_2SO_4$, the intermediate and anisole are subjected to Friedel-Crafts reaction to obtain a Friedel-Crafts product, the Friedel-Crafts product is reacted with $BBr_3$ to obtain a demethylated product, the demethylated product is subjected to ring closing by NaOH and separation to obtain a ring closure product, the ring closure product is subjected to reaction with various sulfonyl chlorides,

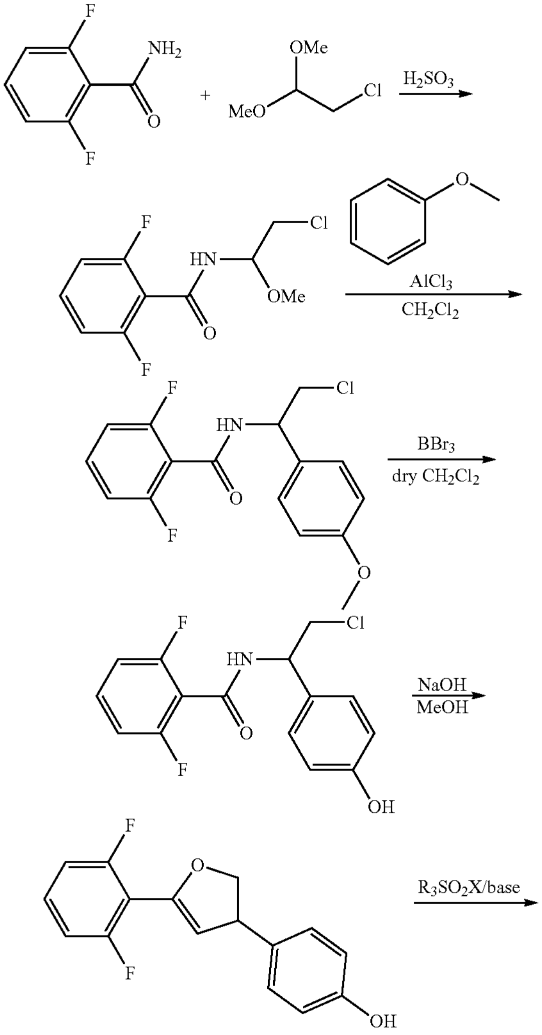

-continued

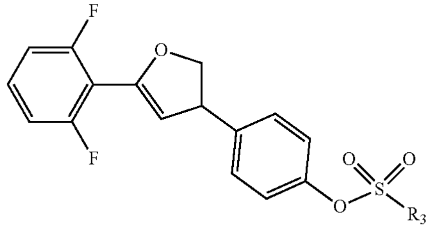

Embodiment Mode 2 the ring closure product reacts with trifluoromethanesulfonic anhydride under the action of alkali,

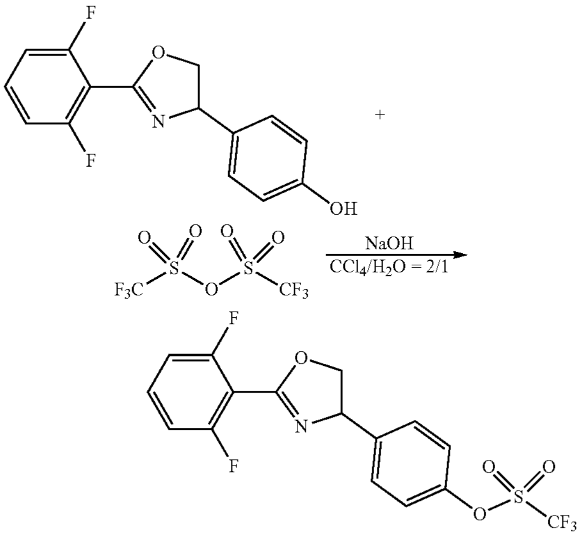

As mentioned previously, a third aspect of the invention provides a process for the preparation of an oxazoline compound.

In the present invention, $X_3$ in the formula (III-1) is preferably a Cl element.

Preferably, the conditions of the second contact reaction at least satisfy: the temperature is above 0° C.

According to a preferred embodiment, the method comprises:

carrying out contact reaction I on the compound shown in the formula (III-1) and the compound shown in the formula (III-2) to obtain the compound shown in the formula (III-4).

Particularly preferably, the compound represented by the formula (III-1) is obtained by reacting p-chloromethylstyrene, NBS and 2,6-difluorobenzonitrile under the catalysis of sulfuric acid at 0-40° C. according to the following scheme; preferably, the molar ratio of the p-chloromethyl styrene to the 2,6-difluorobenzonitrile is 1:1 to 1:2, the molar ratio of the p-chloromethyl styrene to the NBS is 1:1 to 1:2, the reaction concentration of the p-chloromethyl styrene is preferably 0.08 mol/L to 0.8 mol/L, and the reaction solvent is preferably at least one of dichloromethane, trichloromethane and carbon tetrachloride.

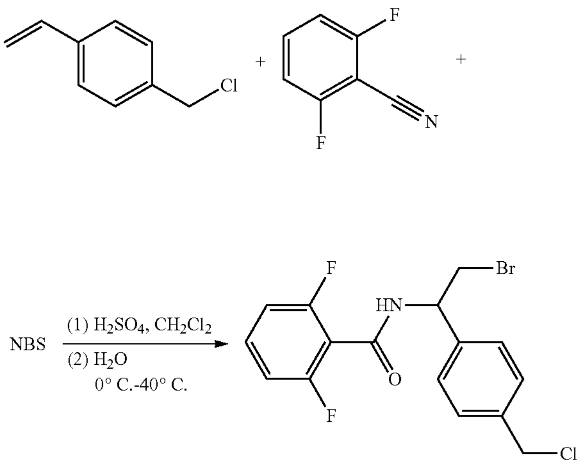

Preferably, the compound represented by the formula (III-1) is reacted in acetonitrile in the presence of sodium hydroxide and then reacted with the compound represented by the formula (III-2) under basic conditions to obtain a compound represented by the formula (III-4) by referring to the following scheme; or directly reacting the compound shown in the formula (III-1) with the compound shown in the formula (III-2) under alkaline conditions to obtain a compound shown in the formula (III-4); preferably, when the compound represented by the formula (III-1) is reacted in acetonitrile in the presence of sodium hydroxide, the molar ratio of the compound represented by the formula (III-1) to sodium hydroxide is 1:1 to 1:2, and the concentration of the compound represented by the formula (III-1) is preferably 0.1 mol/L to 1 mol/L.

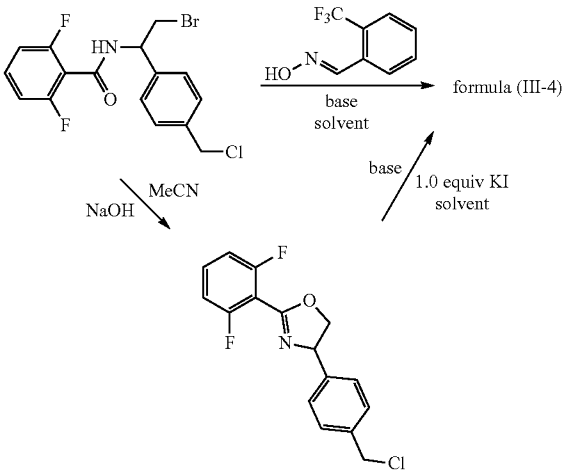 [SMILES: "MeCN" ; O=C(NC(CBr)c1ccc(CCl)cc1)c1c(F)cccc1F ; O/N=C/c1ccccc1C(F)(F)F ; "NaOH" ; Fc1cccc(F)c1C1=NC(c2ccc(CCl)cc2)CO1]

Preferably, the compound represented by the formula (III-1) is reacted in acetonitrile in the presence of sodium hydroxide and then reacted with the compound represented by the formula (III-3) under basic conditions to obtain a compound represented by the formula (III-5) with reference to the following scheme; or directly reacting the compound shown in the formula (III-1) with the compound shown in the formula (III-3) under alkaline conditions to obtain the compound shown in the formula (III-5).

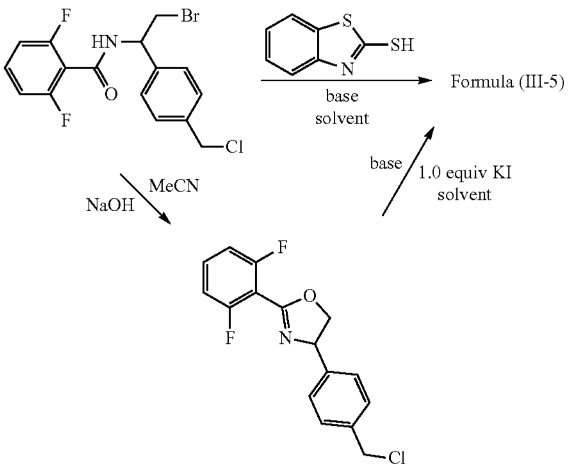 [SMILES: "MeCN" ; O=C(NC(CBr)c1ccc(CCl)cc1)c1c(F)cccc1F ; Sc1nc2ccccc2s1 ; "NaOH" ; Fc1cccc(F)c1C1=NC(c2ccc(CCl)cc2)CO1]

According to a preferred embodiment, the compound of formula (2-1), a base, potassium iodide, o-trifluoromethyl-benzaldehyde oxime are reacted at 25 to 80° C. for 0.5 to 8 h (preferably 3 h) in the presence of a solvent and a protective gas (preferably argon) to give the compound of formula (III-4). Preferably, the molar ratio of the compound represented by the formula (2-1) to the base is 1:1 to 1:2; preferably, the molar ratio of the compound represented by the formula (2-1) to potassium iodide is 1:0.001 to 1:1; preferably, the molar ratio of the compound represented by the formula (2-1) to o-trifluoromethylbenzaldehyde oxime is 1:1 to 1:2; preferably, the reaction concentration of the compound represented by the formula (2-1) is 0.01 mol/L to 0.1 mol/L; preferably, the base is at least one of potassium carbonate, potassium hydroxide and sodium hydroxide, and the solvent for the reaction is at least one of acetonitrile, DMF, acetone and ethanol;

formula (2-1)

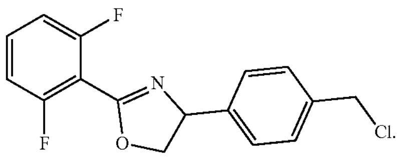

According to another preferred embodiment, the compound of formula (2-1), a base, potassium iodide, 2-mercaptobenzothiazole are reacted at 25 to 80° C. for 0.5 to 8 h (preferably 3 h) in the presence of a solvent and a protective gas, preferably argon, to give the compound of formula (III-5). Preferably, the molar ratio of the compound represented by the formula (2-1) to the base is 1:1 to 1: 2; preferably, the molar ratio of the compound represented by the formula (2-1) to potassium iodide is 1:0.001 to 1:1; preferably, the molar ratio of the compound represented by the formula (2-1) to 2-mercaptobenzothiazole is 1:1 to 1:2; preferably, the reaction concentration of the compound represented by the formula (2-1) is 0.01 mol/L to 0.1 mol/L; preferably, the base is at least one of potassium carbonate, potassium hydroxide, sodium hydroxide, and the solvent of the reaction is at least one of acetonitrile, DMF, acetone, and ethanol.

According to another preferred embodiment, the compound represented by the formula (3-1), o-trifluoromethyl-benzaldehyde oxime and a base are reacted at room temperature under stirring in the presence of a solvent and a protective gas (preferably argon) to obtain a compound represented by the formula (III-4). Preferably, the molar ratio of the compound shown in the formula (3-1) to o-trifluoromethylbenzaldehyde oxime is 1:1 to 1:2; preferably, the molar ratio of the compound represented by the formula (3-1) to the base is 1:1 to 1:5; preferably, the reaction concentration of the compound represented by the formula (3-1) is 0.2 mol/L to 2 mol/L; preferably, the alkali is at least one of sodium hydride, sodium carbonate and sodium hydroxide; preferably, the solvent is at least one of tetrahydrofuran, methanol, toluene, acetone, ethanol, acetonitrile, 1,4-dioxane;

formula (3-1)

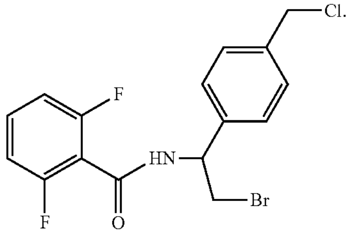

According to another preferred embodiment, the compound represented by the formula (3-1), 2-mercaptobenzothiazole and a base are reacted with stirring at room temperature in the presence of a solvent and a protective gas (preferably argon) to obtain the compound represented by the formula (III-5). Preferably, the molar ratio of the compound represented by the formula (3-1) to 2-mercaptobenzothiazole is 1:1 to 1:2; preferably, the molar ratio of the compound represented by the formula (3-1) to the base is 1:1 to 1:5; preferably, the reaction concentration of the compound represented by the formula (3-1) is 0.2 mol/L to 2 mol/L; preferably, the base is at least one of sodium hydride, sodium carbonate and sodium hydroxide, and the solvent is at least one of tetrahydrofuran, methanol, toluene, acetone, ethanol, acetonitrile and 1, 4-dioxane.

The fourth aspect of the present invention provides an application of a class of oxazoline compounds in controlling phytophagous mites.

The present invention will be described in detail below by way of examples. In the following examples, various raw materials used are commercially available without specific description.

In the examples of the present invention, only a few specific methods for preparing the compounds are exemplified, and those skilled in the art can obtain the compounds of the present invention R1-1~R1-25, R2-1~R2-24, R3-1~R3-24 and the compounds III-4 and III-5 by substituting the starting materials according to the methods for synthesizing the exemplified compounds.

formula (2-1)

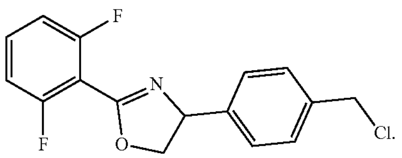

-continued formula (2-2)

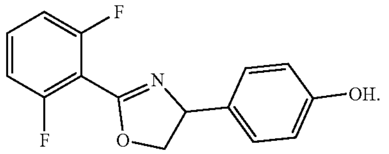

formula (3-1)

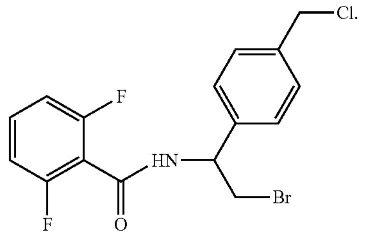

intermediate B

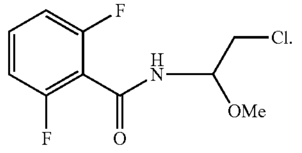

intermediate C

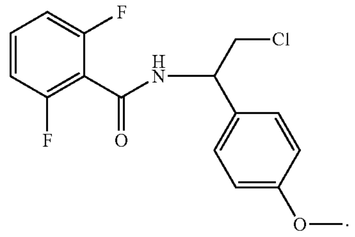

intermediate D

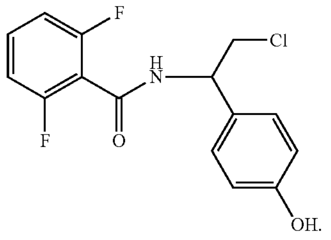

PREPARATION EXAMPLE

Preparation of Compound R2-1

Step 1: 15.3 g of 2,6-difluorobenzonitrile, 15.2 g of 4-vinylbenzyl chloride, 19.6 g of NBS, and 125 mL of $CH_2Cl_2$ were added into a 500 mL single-necked flask, and then 6.5 mL of concentrated sulfuric acid was dropwise added into the system under ice-bath stirring. The mixture was stirred under ice-bath for a while, and then stirred at room temperature (25° C., the following is the same) for 8 hours. After reaction was finished as monitored by TLC, dichloromethane and saturated sodium thiosulfate solution were added for separation, the aqueous phase was extracted with dichloromethane three times. The combined organic phases were washed with saturated sodium bicarbonate solution and saturated sodium chloride solution successively, dried with anhydrous sodium sulfate and then filtered, concentrated under reduced pressure to remove dichloromethane. The residue was carried out column chromatography by using polyethylene and ethyl acetate with the volume ratio of 6:1 (PE/EA=6/1) as eluent to obtain a light yellow solid, namely the compound shown as the formula (3-1), with the yield of 86%, the melting point 128-129° C. $^1$H NMR (400 MHz, DMSO-$d_6$) δ 9.43 (d, J=8.4 Hz, 1H), 7.57-7.50 (m, 1H), 7.40 (d, J=8.0 Hz, 2H), 7.31 (d, J=8.0 Hz, 2H), 7.18 (t, J=8.0 Hz, 2H), 5.29 (dd, J=8.8, 4.4 Hz, 1H), 3.80 (dd, J=10.4, 4.8 Hz, 1H), 3.63 (t, J=10.0 Hz, 1H). $^{13}$C NMR (100 MHz, DMSO-$d_6$) δ 159.9, 159.3 (dd, J=248.9, 8.0 Hz), 140.4, 138.1, 132.2 (t, J=9.9 Hz), 129.9, 127.7, 115.6 (t, J=23.0 Hz), 112.4 (dd, J=19.3, 5.2 Hz), 55.0, 36.1, 34.5. HRMS (ESI): calcd for $C_{16}H_{14}BrClF_2N_2O$ $[M+H]^+$ 389.9889, found: 389.9889.

step 2: 19.4 g of the compound represented by the formula (3-1) was put into a 100 mL single-necked flask and dissolved in 30 mL of methanol. 2.97 g of sodium methoxide was added with stirring in an ice-water bath, stirring was carried out at room temperature. The reaction was monitored by TLC (PE/EA=4/1), and after 5 min, the reaction was completed. Methanol was removed by rotary evaporation, water and dichloromethane were added for separation, and the aqueous phase was extracted three times with dichloromethane. The organic phases were combined and washed by water for 1 time, and washed by saturated sodium chloride for one time, and then the organic phases were dried by anhydrous sodium sulfate, filtered, and then the dichloromethane was removed by concentration under reduced pressure, and the light yellow solid 12.8 g was obtained after drying, namely the compound shown in the formula (2-1), and the yield is 83%. The melting point is 64-65° C. $^1$H NMR (400 MHz, DMSO-$d_6$) δ 7.73-7.62 (m, 1H), 7.47 (d, J=7.8 Hz, 2H), 7.34 (d, J=8.0 Hz, 2H), 7.30 (t, J=8.4 Hz, 2H), 5.51 (dd, J=10.0, 8.0 Hz, 1H), 4.91-4.82 (m, 1H), 4.78 (s, 2H), 4.22 (t, J=8.4 Hz, 1H). $^{13}$C NMR (101 MHz, DMSO-$d_6$) δ 160.7 (dd, J=253.4, 6.4 Hz), 156.5, 142.7, 137.4, 134.1 (t, J=10.4 Hz), 129.7, 127.3, 112.9 (dd, J=19.6, 4.8 Hz), 107.1 (t, J=18.8 Hz), 74.9, 69.5, 46.4. HRMS (ESI): calcd for $C_{16}H_{13}ClF_2NO$ $[M+H]^+$ 308.0648, found: 308.0645.

Or step 2: a 500 mL single-necked flask was charged with the compound represented by the formula (3-1) (0.05 mol, 1.0 equiv), sodium hydroxide (0.06 mol, 1.2 equiv), and 100 mL of acetonitrile. After stirring at room temperature for 12 hours, water and ethyl acetate were added for separation, and the aqueous phase was extracted three times with ethyl acetate. The organic phases were combined, washed by water and salt, dried by anhydrous sodium sulfate and desolventized to obtain 12.4 g of yellow solid with the yield of 81%.

step 3: a compound represented by the formula (2-1) (1 mmol), sodium methoxide (1.0 mmol) and 10 mL of dry THF were dissolved in a 100 mL single-necked flask and the reaction mixture was refluxed under an argon atmosphere. TLC (PE/EA=4/1) monitored the reaction and after 2 hours the reaction was complete. Adding water and dichloromethane for separation, extracting the water phase with dichloromethane for 3 times, combining the organic phases, washing with water for 2 times, washing with saturated sodium chloride for 1 time, drying with anhydrous sodium sulfate, desolventizing, and performing column chromatography (PE/EA=6/1) to obtain a compound R2-1. Colorless transparent oily liquid, yield 67%. $^1$H NMR (400 MHz, DMSO-$d_6$) δ 7.76-7.61 (m, 1H), 7.44-7.21 (m, 6H), 5.50 (dd, J=10.0, 8.0 Hz, 1H), 4.86 (dd, J=10.0, 8.8 Hz, 1H), 4.42 (s, 2H), 4.20 (t, J=8.4 Hz, 1H), 3.30 (s, 3H). $^{13}$C NMR (100 MHz, DMSO-$d_6$) δ 160.2 (dd, J=253.2, 6.1 Hz), 155.8, 141.2, 137.6, 133.5, 127.8, 126.4, 112.3 (dd, J=20.0, 4.5 Hz), 106.6

(t, J=18.6 Hz), 74.4, 73.3, 69.1, 57.4. HRMS (ESI): calcd for $C_{17}H_{15}F_2NO_2$ $[M+H]^+$ 304.1144, found 304.1138.

The synthesis of Compound R2-2 to Compound R2-24 refers to the synthesis of Compound R2-1.

Compound R2-2: colorless transparent oily liquid, yield 57%. $^1$H NMR (400 MHz, $CDCl_3$) δ 7.48-7.29 (m, 5H), 7.00 (t, J=8.0 Hz, 2H), 5.46 (dd, J=10.0, 8.4 Hz, 1H), 4.81 (t, J=8.0 Hz, 1H), 4.51 (s, 2H), 4.28 (t, J=8.0 Hz, 1H), 3.53 (q, J=7.2 Hz, 2H), 1.24 (t, J=7.2 Hz, 3H). $^{13}$C NMR (100 MHz, $CDCl_3$) δ 161.2 (dd, J=256.0, 6.2 Hz), 157.5, 141.1, 138.2, 132.4 (t, J=10.4 Hz), 128.2, 126.7, 112.0 (dd, J=22.9, 2.4 Hz), 107.3 (t, J=18.4 Hz), 74.9, 72.4, 70.1, 65.7, 15.2. HRMS (ESI): calcd for $C_{18}H_{17}F_2NO_2$ $[M+H]^+$ 318.1300, found 318.1295.

Compound R2-3: light yellow oily liquid, yield 50%. $^1$H NMR (400 MHz, $CDCl_3$) δ 7.48-7.28 (m, 5H), 6.99 (t, J=8.4 Hz, 2H), 5.46 (dd, J=10.0, 8.0 Hz, 1H), 4.81 (dd, J=10.0, 8.4 Hz, 1H), 4.51 (s, 2H), 4.28 (t, J=8.0 Hz, 1H), 3.42 (t, J=6.8 Hz, 2H), 1.71-1.56 (m, 2H), 0.93 (t, J=7.6 Hz, 3H). $^{13}$C NMR (100 MHz, $CDCl_3$) δ 161.3 (dd, J=256.0, 6.0 Hz), 157.5, 141.0, 138.3, 132.4 (t, J=10.4 Hz), 128.1, 126.7, 111.9 (dd, J=22.9, 2.4 Hz), 107.3 (t, J=18.4 Hz), 74.9, 72.5, 72.1, 70.1, 23.0, 10.6. HRMS (ESI): calcd for $C_{18}H_{19}F_2NO_2$ $[M+H]^+$ 332.1457, found 332.1453.

Compound R2-4: light yellow oily liquid, yield 53%. $^1$H NMR (400 MHz, $CDCl_3$) δ 7.45-7.29 (m, 5H), 6.97 (t, J=8.2 Hz, 2H), 5.45 (t, J=9.2 Hz, 1H), 4.79 (t, J=9.2 Hz, 1H), 4.61 (dd, J=4.4, 3.6 Hz, 1H), 4.57 (s, 2H), 4.49 (dd, J=4.4, 3.6 Hz, 1H), 4.25 (t, J=8.2 Hz, 1H), 3.69 (dt, J=29.6, 3.6 Hz, 2H). $^{13}$C NMR (100 MHz, $CDCl_3$) δ 161.2 (dd, J=256.0, 6.0 Hz), 157.5, 141.4, 137.4, 132.5 (t, J=10.4 Hz), 128.2, 126.8, 112.0 (dd, J=22.8, 2.4 Hz), 107.2 (t, J=17.8 Hz), 83.1 (d, J=169.0 Hz), 74.8, 73.0, 70.0, 69.2 (d, J=19.7 Hz). HRMS (ESI): calcd for $C_{18}H_{16}F_3NO_2$ $[M+H]^+$ 336.1206, found 336.1200.

Compound R2-5: light yellow oily liquid, yield 63%. $^1$H NMR (400 MHz, $CDCl_3$) δ 7.57-7.23 (m, 5H), 7.03 (t, J=8.4 Hz, 2H), 5.50 (t, J=8.4 Hz, 1H), 4.85 (t, J=9.4 Hz, 1H), 4.70 (s, 2H), 4.31 (t, J=8.0 Hz, 1H), 3.84 (q, J=8.7 Hz, 2H). $^{13}$C NMR (100 MHz, $CDCl_3$) δ 161.2 (dd, J=256.0, 6.0 Hz), 157.7, 142.0, 136.0, 132.5 (t, J=10.4 Hz), 128.4, 127.0, 124.1 (q, J=278.0 Hz), 112.0 (dd, J=22.8, 2.5 Hz), 107.2 (t, J=18.4 Hz), 74.8, 73.7, 70.0, 67.0 (q, J=34.0 Hz). HRMS (ESI): calcd for $C_{18}H_{14}F_5NO_2$ $[M+H]^+$ 372.1017, found 372.1019.

Compound R2-6: colorless transparent oily liquid, yield 67%. $^1$H NMR (400 MHz, $CDCl_3$) δ 7.43 (ddd, J=8.5, 6.3, 2.2 Hz, 1H), 7.40-7.31 (m, 4H), 7.00 (t, J=8.2 Hz, 2H), 5.47 (dd, J=10.2, 8.2 Hz, 1H), 5.00 (s, 1H), 4.92 (s, 1H), 4.82 (dd, J=10.3, 8.4 Hz, 1H), 4.50 (s, 2H), 4.29 (t, J=8.3 Hz, 1H), 3.92 (s, 2H), 1.77 (s, 3H). $^{13}$C NMR (100 MHz, $CDCl_3$) δ 161.5 (dd, J=253.2, 6.1 Hz), 157.5, 142.2, 141.1, 138.0, 132.4 (t, J=10.4 Hz), 128.2, 126.7, 112.0 (dd, J=20.0, 4.5 Hz), 111.8, 107.3, 74.8, 74.1, 71.5, 70.1, 19.5. HRMS (ESI): calcd for $C_{20}H_{19}F_2NO_2$ $[M+H]^+$ 344.1457, found 344.1456.

Compound R2-7: colorless transparent oily liquid, yield 67%. $^1$H NMR (400 MHz, DMSO-$d_6$) δ 7.71-7.65 (m, 1H), 7.38-7.28 (m, 6H), 5.50 (dd, J=10.0, 8.0 Hz, 1H), 4.86 (dd, J=10.0, 8.8 Hz, 1H), 4.52 (s, 2H), 4.21 (t, J=8.0 Hz, 1H), 3.54 (t, J=6.8 Hz, 2H), 2.83 (t, J=2.4 Hz, 1H), 2.46 (td, J=6.8, 2.8 Hz, 2H). $^{13}$C NMR (100 MHz, DMSO-$d_6$) δ 160.2 (dd, J=253.2, 6.1 Hz), 155.8, 141.3, 137.6, 133.5 (t, J=10.4 Hz), 127.8, 126.4, 112.3 (dd, J=21.4, 3.8 Hz), 106.6 (t, J=18.8 Hz), 81.9, 74.5, 71.9, 71.4, 69.1, 67.7, 19.1. HRMS (ESI): calcd for $C_{20}H_{17}F_2NO_2$ $[M+H]^+$ 342.1300, found 342.1296.

Compound R2-8: yellow transparent oily liquid, yield 67%. $^1$H NMR (400 MHz, $CDCl_3$) δ 7.53-7.32 (m, 10H), 7.03 (t, J=8.2 Hz, 2H), 5.51 (dd, J=10.0, 8.4 Hz, 1H), 4.85 (dd, J=10.2, 8.4 Hz, 1H), 4.71 (s, 2H), 4.43 (s, 2H), 4.31 (t, J=8.4 Hz, 1H). $^{13}$C NMR (100 MHz, $CDCl_3$) δ 161.3 (dd, J=256.0, 6.0 Hz), 157.6, 141.5, 137.0, 132.4 (t, J=10.4 Hz), 131.8, 128.7, 128.5, 128.3, 126.8, 122.7, 112.0 (dd, J=22.9, 2.3 Hz), 107.3 (t, J=18.4 Hz), 86.5, 85.0, 74.8, 71.3, 70.1, 57.9. HRMS (ESI): calcd for $C_{25}H_{19}F_2NO_2$ $[M+H]^+$ 404.1457, found 404.1462.

Compound R2-9: yellow transparent oily liquid, yield 67%. $^1$H NMR (400 MHz, $CDCl_3$) δ 7.45 (ddd, J=14.8, 8.4, 6.4 Hz, 1H), 7.42-7.33 (m, 4H), 7.02 (t, J=8.4 Hz, 2H), 5.49 (dd, J=10.0, 8.4 Hz, 1H), 4.84 (dd, J=10.0, 8.4 Hz, 1H), 4.63 (d, J=12.4 Hz, 1H), 4.58 (d, J=12.4 Hz, 1H), 4.31 (t, J=8.4 Hz, 1H), 4.16-4.06 (m, 1H), 3.95-3.86 (m, 1H), 3.80 (dd, J=14.4, 7.2 Hz, 1H), 3.50-3.47 (m, 2H), 2.02-1.85 (m, 3H), 1.64 (dt, J=18.4, 7.6 Hz, 1H). $^{13}$C NMR (100 MHz, $CDCl_3$) δ 161.5 (dd, J=253.2, 6.1 Hz), 160.0, 157.5, 141.1, 137.9, 132.4 (t, J=10.4 Hz), 128.2, 126.7, 111.9 (dd, J=22.8, 2.4 Hz), 77.9, 74.9, 73.0, 72.7, 70.1, 68.4, 28.1, 25.6. HRMS (ESI): calcd for $C_{21}H_{21}F_2NO_3$ $[M+H]^+$ 374.1562, found 374.1566.

Compound R2-10: light yellow oily liquid, yield 66%. $^1$H NMR (400 MHz, $CDCl_3$) δ 7.53-7.33 (m, 6H), 7.02 (t, J=8.0 Hz, 2H), 6.40-6.30 (m, 2H), 5.49 (dd, J=10.0, 8.0 Hz, 1H), 4.84 (dd, J=10.4, 8.4 Hz, 1H), 4.57 (s, 2H), 4.49 (s, 2H), 4.30 (t, J=8.4 Hz, 1H). $^{13}$C NMR (100 MHz, $CDCl_3$) δ 161.3 (dd, J=256.0, 6.0 Hz), 157.6, 151.7, 142.9, 141.3, 137.5, 132.4 (t, J=10.5 Hz), 128.4, 126.8, 112.0 (dd, J=23.0, 2.3 Hz), 110.3, 109.5, 107.3 (t, J=17.7 Hz), 74.9, 71.6, 70.1, 63.8. HRMS (ESI): calcd for $C_{21}H_{17}F_2NO_3$ $[M+H]^+$ 370.1249, found 370.1252.

Compound R2-11: yellow transparent oily liquid, yield 64%. $^1$H NMR (400 MHz, $CDCl_3$) δ 7.52-7.26 (m, 6H), 7.08-6.97 (m, 4H), 5.50 (dd, J=10.0, 8.4 Hz, 1H), 4.85 (dd, J=10.2, 8.4 Hz, 1H), 4.73 (s, 2H), 4.60 (s, 2H), 4.32 (t, J=8.4 Hz, 1H). $^{13}$C NMR (100 MHz, $CDCl_3$) δ 161.3 (dd, J=256.0, 6.0 Hz), 157.6, 141.3, 141.0, 137.5, 132.4 (t, J=10.4 Hz), 128.4, 126.8, 126.7, 126.6, 125.9, 112.0 (dd, J=23.0, 2.2 Hz), 107.3 (t, J=18.4 Hz), 74.8, 71.3, 70.1, 66.4. HRMS (ESI): calcd for $C_{21}H_{17}F_2NO_2S$ $[M+H]^+$ 386.1021, found 386.1024.

Compound R2-12: light yellow oily liquid, yield 87%. $^1$H NMR (400 MHz, $CDCl_3$) δ 7.54-7.21 (m, 7H), 7.00 (t, J=8.4 Hz, 2H), 6.62 (d, J=9.0 Hz, 1H), 6.14 (t, J=6.8 Hz, 1H), 5.46 (dd, J=10.0, 8.4 Hz, 1H), 5.15 (s, 2H), 4.81 (t, J=8.4 Hz, 1H), 4.28 (t, J=8.4 Hz, 1H). $^{13}$C NMR (100 MHz, $CDCl_3$) δ 161.2 (dd, J=256.0, 6.1 Hz), 157.6, 146.8, 141.7, 139.5, 137.2, 135.9, 132.5 (t, J=10.3 Hz), 128.7, 127.2, 121.2, 112.0 (dd, J=21.7, 3.6 Hz), 107.2 (t, J=18.0 Hz), 106.3, 74.7, 69.9, 51.6. HRMS (ESI): calcd for $C_{21}H_{16}F_2N_2O_2$ $[M+H]^+$ 367.1253, found 370.1256.

Compound R2-13: yellow solid, yield 67%, melting point: 81-82° C. $^1$H NMR (400 MHz, $CDCl_3$) δ 8.39 (d, J=2.4 Hz, 1H), 8.23 (dd, J=4.4, 1.2 Hz, 1H), 7.52-7.32 (m, 5H), 7.24-7.17 (m, 2H), 7.00 (t, J=8.0 Hz, 2H), 5.49 (dd, J=10.0, 8.0 Hz, 1H), 5.12 (s, 2H), 4.83 (dd, J=10.4, 8.4 Hz, 1H), 4.29 (t, J=8.4 Hz, 1H). $^{13}$C NMR (100 MHz, $CDCl_3$) δ 161.2 (dd, J=256.2, 6.1 Hz), 157.7, 154.8, 142.4, 142.0, 138.4, 135.7, 132.5 (t, J=10.5 Hz), 128.0, 127.1, 123.8, 121.5, 112.0 (dd, J=22.8, 2.6 Hz), 107.2 (t, J=17.8 Hz), 74.8, 70.0, 70.0. HRMS (ESI): calcd for $C_{21}H_{16}F_2N_2O_2$ $[M+H]^+$ 367.1253, found 367.1247.

Compound R2-14: yellow solid, yield 63%, melting point: 133-134° C. $^1$H NMR (400 MHz, $CDCl_3$) δ 7.50-7.31 (m, 5H), 7.20 (d, J=8.0 Hz, 2H), 7.00 (t, J=8.4 Hz, 2H), 6.36

(d, J=7.6 Hz, 2H), 5.47 (dd, J=10.0, 8.0 Hz, 1H), 4.95 (s, 2H), 4.83 (dd, J=10.4, 8.4 Hz, 1H), 4.27 (t, J=8.4 Hz, 1H). $^{13}$C NMR (100 MHz, $CDCl_3$) δ 178.8, 161.1 (dd, J=256.0, 6.0 Hz), 157.8, 142.6, 140.1, 134.4, 132.6 (t, J=10.4 Hz), 127.9, 127.6, 118.8, 112.0 (dd, J=23.0, 2.0 Hz), 106.9 (t, J=17.7 Hz), 74.6, 69.8, 59.6. HRMS (ESI): calcd for $C_{21}H_{16}F_2N_2O_2$ [M+H]$^+$ 367.1253, found 367.1247.

Compound R2-15: light yellow oily liquid, yield 73%. $^1$H NMR (400 MHz, $CDCl_3$) δ 7.39 (m, 5H), 7.07 (m, 2H), 7.00 (t, J=8.4 Hz, 2H), 6.07 (td, J=7.2, 4.4 Hz, 1H), 5.45 (dd, J=10.4, 8.0 Hz, 1H), 5.19 (s, 2H), 4.81 (dd, J=10.4, 8.4 Hz, 1H), 4.27 (t, J=8.4 Hz, 1H). $^{13}$C NMR (100 MHz, $CDCl_3$) δ 161.2 (dd, J=256.0, 6.0 Hz), 157.7, 156.4 (d, J=25.5 Hz), 152.6 (d, J=250.0 Hz), 142.0, 135.3, 132.6, 132.5 (t, J=10.4 Hz), 128.8, 127.3, 120.0 (d, J=17.2 Hz), 112.0 (dd, J=22.9, 2.3 Hz), 107.1 (t, J=17.7 Hz), 104.0 (d, J=5.7 Hz), 74.7, 69.9, 51.7. HRMS (ESI): calcd for $C_{21}H_{15}F_2N_2O_2$ [M+H]$^+$ 385.1158, found 385.1154.

Compound R2-16: light yellow solid, yield 75%, melting point: 91-92° C. $^1$H NMR (400 MHz, $CDCl_3$) δ 8.15 (s, 1H), 7.86 (d, J=6.4 Hz, 1H), 7.47-7.30 (m, 5H), 6.99 (t, J=8.4 Hz, 2H), 6.46 (d, J=6.4 Hz, 1H), 5.45 (t, J=9.2 Hz, 1H), 5.10 (s, 2H), 4.80 (t, J=9.4 Hz, 1H), 4.26 (t, J=8.4 Hz, 1H). $^{13}$C NMR (100 MHz, $CDCl_3$) δ 161.2 (dd, J=256.0, 6.0 Hz), 160.8, 157.7, 153.3, 151.1, 142.2, 134.6, 132.5 (t, J=10.4 Hz), 128.7, 127.4, 116.2, 112.0 (dd, J=22.6, 2.5 Hz), 107.1 (t, J=17.7 Hz), 74.6, 69.8, 49.4. HRMS (ESI): calcd for $C_{20}H_{15}F_2N_3O_2$ [M+H]$^+$ 368.1205, found 368.1198.

Compound R2-17: light yellow solid, yield 68%, melting point: 52-53° C. $^1$H NMR (400 MHz, $CDCl_3$) δ 8.57 (t, J=4.0 Hz, 1H), 7.61 (dd, J=6.4, 2.8 Hz, 1H), 7.49-7.33 (m, 5H), 7.00 (t, J=8.4 Hz, 2H), 6.26 (dd, J=6.4, 4.0 Hz, 1H), 5.46 (dd, J=10.4, 8.0 Hz, 1H), 5.10 (s, 2H), 4.82 (dd, J=10.4, 8.4 Hz, 1H), 4.27 (t, J=8.4 Hz, 1H). $^{13}$C NMR (100 MHz, $CDCl_3$) δ 165.9, 161.1 (dd, J=256.0, 6.0 Hz), 157.7, 156.4, 147.7, 142.2, 134.4, 132.6 (t, J=10.4 Hz), 129.1, 127.4, 112.0 (dd, J=22.8, 2.4 Hz), 107.0 (t, J=17.8 Hz), 104.3, 74.6, 69.8, 53.6. HRMS (ESI): calcd for $C_{20}H_{15}F_2N_3O_2$ [M+H]$^+$ 368.1205, found 368.1201.

Compound R2-18: White solid powder, yield 76%, melting point: 85-86° C. $^1$H NMR (400 MHz, $CDCl_3$) δ 7.43-7.38 (m, 5H), 7.01-6.84 (m, 6H), 5.46 (dd, J=10.4, 8.4 Hz, 1H), 5.00 (s, 2H), 4.79 (dd, J=10.4, 8.4 Hz, 1H), 4.27 (t, J=8.4 Hz, 1H). $^{13}$C NMR (100 MHz, $CDCl_3$) δ 161.2 (dd, J=256.0, 5.8 Hz), 157.6, 157.4 (d, J=237.0 Hz), 154.8 (d, J=1.6 Hz), 141.7, 136.4, 132.5 (t, J=10.4 Hz), 128.0, 127.0, 116.0, 115.8 (d, J=16.0 Hz), 112.0 (dd, J=21.5, 3.6 Hz), 107.2 (t, J=18.0 Hz), 74.8, 70.3, 70.0. HRMS (ESI): calcd for $C_{22}H_{16}F_3NO_2$ [M+H]$^+$ 384.1206, found 384.1212.

Compound R2-19: white solid powder, yield 80%, melting point: 100-102° C. $^1$H NMR (400 MHz, $CDCl_3$) δ 7.49-7.31 (m, 5H), 7.25-7.20 (m, 2H), 7.01 (t, J=8.0 Hz, 2H), 6.92-6.86 (m, 2H), 5.48 (dd, J=10.4, 8.0 Hz, 1H), 5.04 (s, 2H), 4.83 (dd, J=10.4, 8.4 Hz, 1H), 4.30 (t, J=8.4 Hz, 1H). $^{13}$C NMR (100 MHz, $CDCl_3$) δ 161.2 (dd, J=256.0, 6.0 Hz), 157.7, 157.3, 141.7, 136.2, 132.5 (t, J=10.4 Hz), 129.4, 127.9, 127.0, 125.8, 116.2, 112.0 (dd, J=23.0, 2.4 Hz), 107.2 (t, J=17.8 Hz), 74.8, 70.1, 70.0. HRMS (ESI): calcd for $C_{22}H_{16}ClF_2NO_2$ [M+H]$^+$ 400.0910, found 400.0912.

Compound R2-20: white solid, yield 75%, melting point: 99-100° C. $^1$H NMR (400 MHz, $CDCl_3$) δ 7.41-7.34 (m, 7H), 6.97 (t, J=9.0 Hz, 2H), 6.82 (d, J=7.0 Hz, 2H), 5.46 (t, J=8.8 Hz, 1H), 5.00 (s, 2H), 4.80 (t, J=8.8 Hz, 1H), 4.27 (t, J=7.6 Hz, 1H). $^{13}$C NMR (100 MHz, $CDCl_3$) δ 161.2 (dd, J=256.0, 6.0 Hz), 157.8, 141.8, 136.1, 132.5 (t, J=10.4 Hz), 132.3, 127.9, 127.0, 120.4, 116.7, 113.2, 112.0 (dd, J=22.8, 2.5 Hz), 107.2 (t, J=17.7 Hz), 74.8, 70.0, 69.9. HRMS (ESI): calcd for $C_{22}H_{16}BrF_2NO_2$ [M+H]$^+$ 444.0405, found 444.0408.

Compound R2-21: white solid powder, yield 83%, melting point: 82-83° C. $^1$H NMR (400 MHz, $CDCl_3$) δ 7.62-7.37 (m, 6H), 7.30-7.21 (m, 1H), 7.05-6.86 (m, 4H), 5.51 (dd, J=10.0, 8.4 Hz, 1H), 5.19 (s, 2H), 4.85 (dd, J=10.0, 8.4 Hz, 1H), 4.33 (t, J=8.4 Hz, 1H). $^{13}$C NMR (100 MHz, $CDCl_3$) δ 161.3 (dd, J=256.1, 5.8 Hz), 157.6, 155.0, 141.5, 136.1, 133.5, 132.5 (t, J=10.5 Hz), 128.4, 127.5, 127.0, 122.2, 113.9, 112.5, 112.0 (dd, J=22.9, 2.3 Hz), 107.2 (t, J=17.6 Hz), 74.8, 70.5, 70.1. HRMS (ESI): calcd for $C_{22}H_{16}BrF_2NO_2$ [M+H]$^+$ 444.0405, found 444.0408.

Compound R2-22: white solid powder, yield 83%, melting point: 85-86° C. $^1$H NMR (400 MHz, $CDCl_3$) δ 7.54-7.35 (m, 5H), 7.18-6.86 (m, 6H), 5.53 (dd, J=10.0, 8.4 Hz, 1H), 5.09 (s, 2H), 4.86 (dd, J=10.0, 8.4 Hz, 1H), 4.34 (t, J=8.0 Hz, 1H), 2.34 (s, 3H). $^{13}$C NMR (100 MHz, $CDCl_3$) δ 161.3 (dd, J=256.0, 6.0 Hz), 157.6, 156.7, 141.5, 136.9, 132.5 (t, J=10.4 Hz), 130.2, 130.0, 128.0, 126.9, 114.8, 112.0 (dd, J=22.9, 2.4 Hz), 107.3 (t, J=17.4 Hz), 74.8, 70.1, 69.8, 20.5. HRMS (ESI): calcd for $C_{23}H_{19}F_2NO_2$ [M+H]$^+$ 380.1457, found 380.1459.

Compound R2-23: White solid powder, yield 78%, melting point: 115-117° C. $^1$H NMR (400 MHz, $CDCl_3$) δ 7.58-7.35 (m, 7H), 7.08-6.96 (m, 4H), 5.50 (dd, J=10.4, 8.0 Hz, 1H), 5.12 (s, 2H), 4.84 (dd, J=10.4, 8.4 Hz, 1H), 4.31 (t, J=8.4 Hz, 1H). $^{13}$C NMR (100 MHz, $CDCl_3$) δ 161.25 (dd, J=256.0, 6.0 Hz), 161.1, 157.7, 141.9, 135.8, 132.5 (t, J=10.5 Hz), 127.9, 127.0, 126.9 (dd, J=7.1, 3.5 Hz), 123.3, 124.4 (q, J=279.8 Hz), 114.9, 112.0 (dd, J=21.5, 3.7 Hz), 107.1 (t, J=10.5 Hz), 74.8, 70.0, 69.9. HRMS (ESI): calcd for $C_{23}H_{16}F_5NO_2$ [M+H]$^+$ 434.1174, found 434.1173.

Compound R2-24: white solid powder, yield 75%, melting point: 118-120° C. $^1$H NMR (400 MHz, $CDCl_3$) δ 7.79-7.68 (m, 3H), 7.53-7.30 (m, 7H), 7.25-7.19 (m, 2H), 7.00 (t, J =8.0 Hz, 2H), 5.49 (dd, J=10.0, 8.4 Hz, 1H), 5.19 (s, 2H), 4.83 (dd, J=10.4, 8.4 Hz, 1H), 4.31 (t, J=8.4 Hz, 1H). $^{13}$C NMR (100 MHz, $CDCl_3$) δ 161.3 (dd, J=256.0, 6.0 Hz), 157.7, 156.7, 141.6, 136.5, 134.5, 132.5 (t, J=10.5 Hz), 129.5, 129.1, 128.1, 127.7, 127.2, 127.0, 126.8, 126.4, 123.8, 119.1, 112.0 (dd, J=22.8, 2.5 Hz), 107.2 (t, J=18.4 Hz), 74.8, 70.1, 69.7. HRMS (ESI): calcd for $C_{26}H_{19}F_2NO_2$ [M+H]$^+$ 416.1457, found 416.1461.

Preparation of Compound R1-1

2mmol of the compound shown as a formula (2-1) was added into a 100 mL single-necked bottle, 2.4 mmol of a nitrogen-containing heterocyclic ring, 2.4 mmol of potassium iodide, 2.4 mmol of sodium hydroxide and 15 mL of acetonitrile were then added, and the reaction mixture was stirred at room temperature and monitored by TLC. After 12 hours, the reaction solution was poured into a separating funnel, water and dichloromethane were added for separation, the aqueous phase was extracted with dichloromethane for three times. The organic phases were combined, washed for one time with water and then saturated sodium chloride, dried by anhydrous sodium sulfate, filtered, and then concentrated under reduced pressure to remove dichloromethane, performed column chromatography eluting with an eluent which is 2: 1 ethyl acetate and polyethylene.

Compound R1-1: light yellow transparent oily liquid, yield 83%. $^1$H NMR (400 MHz, DMSO-$d_6$) δ 7.69-7.60 (m, 1H), 7.34-7.23 (m, 6H), 5.46 (dd, J=10.0, 8.0 Hz, 1H), 4.83 (dd, J=10.0, 8.8 Hz, 1H), 4.19 (t, J=8.0 Hz, 1H), 3.55 (s, 2H), 1.66 (s, 4H). $^{13}$C NMR (100 MHz, DMSO-$d_6$) δ 160.7 (dd, J=253.4, 6.3 Hz), 156.3, 141.0, 139.1, 134.0 (t, J=10.5 Hz), 129.2, 126.8, 112.8 (dd, J=19.8, 4.8 Hz), 107.2 (t, J=18.5 Hz), 74.9, 69.7, 59.7, 53.9, 23.5. HRMS (ESI): calcd for $C_{20}H_{21}F_2NO_2$ $[M+H]^+$ 343.1616, found:343.1622.

Compound R1-2 to compound R1-25 were synthesized in a similar manner to compound R1-1.

Compound R1-2: light yellow oily liquid, yield 72%. $^1H$ NMR (400 MHz, DMSO-$d_6$) δ 7.71-7.62 (m, 1H), 7.36-7.24 (m, 6H), 5.46 (dd, J=10.0, 8.4 Hz, 1H), 4.89-4.80 (m, 1H), 4.20 (t, J=8.0 Hz, 1H), 3.58 (s, 2H), 3.45-3.33 (m, 4H), 1.56 (s, 8H). $^{13}C$ NMR (100 MHz, DMSO-$d_6$) δ 160.7 (dd, J=253.4, 6.2 Hz), 156.2, 140.9, 139.7, 134.0 (t, J=10.4 Hz), 129.1, 126.8, 112.8 (dd, J=19.9, 4.6 Hz), 107.2 (t, J=18.5 Hz), 74.9, 69.7, 62.1, 55.5, 28.4, 26.9. HRMS (ESI): calcd for $C_{22}H_{25}F_2NO_2$ $[M+H]^+$ 371.1929, found:371.1936.

Compound R1-3: colorless transparent oily liquid, yield 82%. $^1H$ NMR (400 MHz, DMSO-$d_6$) δ 7.69-7.59 (m, 1H), 7.32 (d, J=7.8 Hz, 2H), 7.28-7.23 (m, 4H), 5.48-5.41 (m, 1H), 4.84-4.79 (m, 1H), 4.17 (t, J=8.0 Hz, 1H), 3.53 (s, 2H), 2.46 (t, J=5.6 Hz, 4H), 1.65-1.40 (m, 10H). $^{13}C$ NMR (100 MHz, DMSO-$d_6$) δ 160.2 (dd, J=253.5, 6.1 Hz), 155.7, 140.4, 139.5, 133.5 (t, J=10.4 Hz), 128.8, 126.2, 112.3 (dd, J=19.9, 4.2 Hz), 106.7 (t, J=18.5 Hz), 74.4, 69.2, 62.6, 53.6, 27.4, 25.5. HRMS (ESI): calcd for $C_{23}H_{27}F_2NO_2$ $[M+H]^+$ 385.2086, found:385.2090.

Compound R1-4: light yellow oily liquid, 95%. $^1H$ NMR (400 MHz, DMSO-$d_6$) δ 7.79-7.58 (m, 1H), 7.34-7.26 (m, 6H), 5.46 (dd, J=10.0, 8.0 Hz, 1H), 4.83 (dd, J=10.0, 8.8 Hz, 1H), 4.20 (t, J=8.0 Hz, 1H), 3.61-3.50 (m, 4H), 3.45 (s, 2H), 2.34 (s, 4H). $^{13}C$ NMR (100 MHz, DMSO-$d_6$) δ 160.7 (dd, J=253.2, 6.2 Hz), 156.3, 141.3, 137.6, 134.1 (t, J=10.4 Hz), 129.7, 126.9, 112.9 (dd, J=19.8, 4.8 Hz), 107.2 (t, J=18.7 Hz), 74.9, 69.6, 66.7, 62.6, 53.6. HRMS (ESI): calcd for $C_{20}H_{21}F_2N_2O_2$ $[M+H]^+$ 359.1566, found:359.1568.

Compound R1-5: light yellow oily liquid, yield 60%. $^1H$ NMR (400 MHz, DMSO) δ 7.70-7.62 (m, 1H), 7.30-7.25 (m, 4H), 7.21 (d, J=8.0 Hz, 2H), 6.82 (t, J=2.0 Hz, 2H), 6.02 (t, J=2.0 Hz, 2H), 5.46 (dd, J=10.0, 8.0 Hz, 1H), 5.09 (s, 2H), 4.82 (dd, J=10.0, 8.8 Hz, 1H), 4.19 (t, J=8.0 Hz, 1H). $^{13}C$ NMR (100 MHz, DMSO) δ 160.2 (dd, J=253.1, 6.1 Hz), 155.8, 141.2, 138.3, 133.5 (t, J=10.5 Hz), 127.5, 126.7, 120.9, 112.3 (dd, J=19.9, 4.8 Hz), 108.0, 106.6 (t, J=18.6 Hz), 74.4, 69.0, 51.9. HRMS (ESI): calcd for $C_{20}H_{17}F_2N_2O$ [M+H]+ 339.1303, found:339.1304.

Compound R1-6: yellow oily liquid, yield 79%. $^1H$ NMR (400 MHz, $CDCl_3$) δ 7.48-7.37 (m, 3H), 7.32 (d, J=8.0 Hz, 2H), 7.01 (t, J=8.4 Hz, 2H), 5.80 (s, 2H), 5.47 (dd, J=10.0, 8.4 Hz, 1H), 4.83 (dd, J=10.0, 8.8 Hz, 1H), 4.32 (t, J=8.4 Hz, 1H), 3.84 (s, 2H), 3.50 (s, 4H). $^{13}C$ NMR (100 MHz, DMSO-$d_6$) δ 160.7 (dd, J=253.3, 6.1 Hz), 156.2, 141.0, 139.6, 134.0 (t, J=10.4 Hz), 129.0, 128.2, 126.9, 112.8 (dd, J=19.8, 4.8 Hz), 107.2 (t, J=18.5 Hz), 75.0, 69.6, 59.8, 59.6. HRMS (ESI): calcd for $C_{20}H_{19}F_2N_2O$ $[M+H]^+$ 341.1460, found:341.1467.

Compound R1-7: colorless and transparent oily liquid, with a yield of 45%. $^1H$ NMR (400 MHz, DMSO-$d_6$) δ 7.72-7.63 (m, 1H), 7.34-7.23 (m, 6H), 5.48 (dd, J=10.0, 8.0 Hz, 1H), 4.89-4.81 (m, 1H), 4.38 (s, 2H), 4.21 (t, J=8.0 Hz, 1H), 3.24 (t, J=7.2 Hz, 2H), 2.30 (t, J=8.0 Hz, 2H), 1.98-1.88 (m, 2H). $^{13}C$ NMR (100 MHz, DMSO-$d_6$) δ 174.0, 160.2 (dd, J=253.2, 6.2 Hz), 155.8, 141.0, 136.3, 133.6 (t, J=10.4 Hz), 127.9, 126.8, 112.4 (dd, J=20.0, 4.6 Hz), 106.6 (t, J=18.4 Hz), 74.4, 69.0, 46.1, 45.2, 30.2, 17.3. HRMS (ESI): calcd for $C_{20}H_{19}F_2N_2O_2$ $[M+H]^+$ 357.1409, found: 357.1415.

Compound R1-8: colorless transparent oily liquid, yield 67%. $^1H$ NMR (400 MHz, DMSO-$d_6$) δ 7.69-7.60 (m, 1H), 7.35-7.23 (m, 6H), 5.49 (dd, J=10.0, 8.0 Hz, 1H), 4.84 (dd, J=10.0, 8.8 Hz, 1H), 4.39 (s, 2H), 4.20 (t, J=8.0 Hz, 1H), 3.69 (t, J=8.0 Hz, 2H), 3.28(t, J =8.0 Hz, 2H), 2.39 (s, 3H). $^{13}C$ NMR (100 MHz, DMSO-$d_6$) δ 169.5, 160.2 (dd, J=253.4, 6.2 Hz), 155.9, 154.4, 141.3, 135.7, 133.5 (t, J=10.4 Hz), 128.1, 126.8, 112.3 (dd, J=20.0, 4.4 Hz), 106.6 (t, J=18.4 Hz), 74.4, 69.0, 46.4, 40.0, 39.2, 22.9. HRMS (ESI): calcd for $C_{21}H_{20}F_2N_3O_3$ $[M+H]^+$ 400.1467, found: 400.1471.

Compound R1-9: white solid, yield 84%. Melting point 132-133° C. $^1H$ NMR (400 MHz, DMSO-$d_6$) δ 7.72-7.64 (m, 1H), 7.35-7.26 (m, 6H), 5.47 (dd, J=10.0, 8.0 Hz, 1H), 4.83 (dd, J=10.0, 8.8 Hz, 1H), 4.56 (s, 2H), 4.20 (t, J=8.0 Hz, 1H), 2.70 (s, 4H). $^{13}C$ NMR (100 MHz, DMSO-$d_6$) δ 177.6, 160.2 (dd, J=253.2, 6.2 Hz), 155.8, 141.2, 135.6, 133.6 (t, J=10.4 Hz), 127.8, 126.6, 112.4 (dd, J=19.8, 4.6 Hz), 106.6 (t, J=18.9 Hz), 74.4, 69.0, 41.0, 28.1 HRMS (ESI): calcd for $C_{20}H_{17}F_2N_2O_3$ $[M+H]^+$ 371.1202, found:371.1205.

Compound R1-10: white solid, yield 81%, melting point 106-107° C. $^1H$ NMR (400 MHz, DMSO-$d_6$) δ 7.94-7.85 (m, 4H), 7.71-7.63 (m, 1H), 7.35 (d, J=8.0 Hz, 2H), 7.33-7.25 (m, 4H), 5.47 (dd, J=10.0, 8.0 Hz, 1H), 4.82 (dd, J=10.0, 8.8 Hz, 1H), 4.79 (s, 2H), 4.19 (t, J=8.0 Hz, 1H). $^{13}C$ NMR (100 MHz, DMSO-$d_6$) δ 168.2, 160.6 (dd, J=253.3, 6.2 Hz), 156.4, 141.8, 136.4, 135.1, 134.1 (t, J=10.5 Hz), 132.0, 128.2, 127.3, 123.7, 112.9 (dd, J=19.8, 4.8 Hz), 107.1 (t, J=18.6 Hz), 74.9, 69.4, 41.0. HRMS (ESI): calcd for $C_{24}H_{17}F_2N_2O_3$ $[M+H]^+$ 419.1202, found:419.1206.

Compound R1-11: light yellow oily liquid, 79%. $^1H$ NMR (400 MHz, DMSO-$d_6$) δ 7.79 (s, 1H), 7.73-7.59 (m, 1H), 7.33-7.26 (m, J=8.4 Hz, 6H), 7.21 (s, 1H), 6.92 (s, 1H), 5.47 (dd, J=10.0, 8.0 Hz, 1H), 5.20 (s, 2H), 4.83 (dd, J=10.0, 8.8 Hz, 1H), 4.19 (t, J=8.0 Hz, 1H). $^{13}C$ NMR (100 MHz, DMSO-$d_6$) δ 160.7 (dd, J=253.3, 6.1 Hz), 156.4, 142.1, 137.5, 134.1 (t, J=10.4 Hz), 129.1, 128.3, 127.3, 120.0, 112.9 (dd, J=20.0, 4.5 Hz), 107.1 (t, J=18.6 Hz), 74.9, 69.5, 49.7. HRMS (ESI): calcd for $C_{19}H_{16}F_2N_3O$ $[M+H]^+$ 340.1256, found:340.1263.

Compound R1-12: yellow oily liquid, 78%. $^1H$ NMR (400 MHz, DMSO-$d_6$) δ 7.83 (d, J=2.0 Hz, 1H), 7.71-7.62 (tt, J=8.4, 6.4 Hz, 1H), 7.46 (d, J=1.3 Hz, 1H), 7.35-7.20 (m, 6H), 6.27 (t, J=2.0 Hz, 1H), 5.46 (dd, J=10.0, 8.0 Hz, 1H), 5.34 (s, 2H), 4.82 (dd, J=10.0, 8.8 Hz, 1H), 4.19 (t, J=8.0 Hz, 1H). $^{13}C$ NMR (100 MHz, DMSO-$d_6$) δ 160.6 (dd, J=253.3, 6.2 Hz), 156.4, 141.9, 139.5, 137.5, 134.1 (t, J=10.5 Hz), 130.6, 128.3, 127.1, 112.9 (dd, J=19.9, 4.8 Hz), 107.1 (t, J=18.6 Hz), 106.0, 74.9, 69.5, 54.8. HRMS (ESI): calcd for $C_{19}H_{16}F_2N_3O$ $[M+H]^+$ 340.1256, found: 340.1263.

Compound R1-13: yellow oily liquid, 78%. $^1H$ NMR (400 MHz, $CDCl_3$) δ 7.46-7.34 (m, 3H), 7.31 (d, J=8.0 Hz, 2H), 7.13-7.05 (m, 3H), 6.97 (t, J=8.0 Hz, 1H), 5.44 (dd, J=10.0, 8.0 Hz, 1H), 4.80 (dd, J=10.4, 8.4 Hz, 1H), 4.30 (t, J=8.4 Hz, 1H), 3.66 (s, 2H), 3.61 (s, 2H), 2.88 (t, J=5.6 Hz, 2H), 2.72 (t, J=6.0 Hz, 2H). $^{13}C$ NMR (100 MHz, $CDCl_3$) δ 161.3 (dd, J=256.0, 6.1 Hz), 157.5, 140.6, 138.0, 134.9, 134.4, 132.5 (t, J=10.3 Hz), 129.6, 128.7, 126.7, 126.7, 126.1, 125.6, 112.0 (dd, J=20.3, 4.9 Hz), 107.3 (t, J=17.7 Hz), 74.9, 70.2, 62.5, 56.2, 50.7, 29.2. HRMS (ESI): calcd for $C_{25}H_{23}F_2N_2O$ $[M+H]^+$ 405.1773. found:405.1781.

Compound R1-14: yellow-brown oily liquid, yield 88%. $^1H$ NMR (400 MHz, $CDCl_3$) δ 7.51-7.40 (m, 3H), 7.36 (d, J=8.0 Hz, 2H), 7.15-7.01 (m, 4H), 6.71 (t, J=7.2 Hz, 1H), 6.55 (d, J=7.6 Hz, 1H), 5.50 (dd, J=10.0, 8.4 Hz, 1H), 4.86 (dd, J=10.0, 8.4 Hz, 1H), 4.35 (t, J=8.0 Hz, 1H), 4.29 (s, 2H), 3.34 (t, J=8.4 Hz, 2H), 3.01 (t, J=8.4 Hz, 2H). $^{13}C$ NMR (100 MHz, $CDCl_3$) δ 161.3 (dd, J=256.2, 5.9 Hz), 157.5, 152.5, 140.7, 138.1, 132.4 (t, J=10.4 Hz), 130.1, 128.4, 127.3, 126.9, 124.5, 117.8, 112.0 (dd, J=20.3, 4.8 Hz), 107.3 (t, J=17.8 Hz), 107.1, 74.9, 70.1, 53.6, 53.4, 28.6. HRMS (ESI): calcd for $C_{24}H_{21}F_2N_2O$ [M+H]+ 391.1616, found: 391.1624.

Compound R1-15: light green solid, yield 63%, mp melting point 111-112° C. $^1$H NMR (400 MHz, DMSO-$d_6$) δ 7.71-7.60 (m, 1H), 7.56 (d, J=7.6 Hz, 1H), 7.51 (d, J=3.2 Hz, 1H), 7.45 (d, J=8.4 Hz, 1H), 7.30-7.20 (m, 6H), 7.09 (t, J=7.6 Hz, 1H), 7.01 (dd, J=7.6, 7.2 Hz, 1H), 6.49 (d, J=3.0 Hz, 1H), 5.47-5.38 (m, 3H), 4.79 (dd, J=10.0, 8.8 Hz, 1H), 4.16 (t, J=8.0 Hz, 1H). $^{13}$C NMR (100 MHz, DMSO-$d_6$) δ 160.2 (dd, J=253.3, 6.2 Hz), 155.8, 141.2, 137.6, 135.7, 133.5, 129.0, 128.3, 127.3, 126.7, 121.1, 120.4, 119.1, 112.3 (dd, J=20.2, 4.3 Hz), 110.1, 106.6 (t, J=19.8 Hz), 101.0, 74.33, 69.0, 48.8. HRMS (ESI): calcd for $C_{24}H_{19}F_2N_2O$ $[M+H]^+$ 389.1460, found:389.1471.

Compound R1-16: Lilac solid, yield 53%, mp melting point 67-68° C. $^1$H NMR (400 MHz, DMSO-$d_6$) δ 7.72-7.62 (m, 1H), 7.45 (d, J=3.2 Hz, 1H), 7.36-7.23 (m, 6H), 7.20 (d, J=8.0 Hz, 2H), 6.92 (d, J=9.2 Hz, 1H), 6.39 (d, J=3.2 Hz, 1H), 5.43 (dd, J=10.0, 8.0 Hz, 1H), 5.39 (s, 2H), 4.80 (dd, J=10.2, 8.6 Hz, 1H), 4.17 (t, J=8.2 Hz, 1H), 2.36 (s, 3H). $^{13}$C NMR (100 MHz, DMSO-$d_6$) δ 160.1 (dd, J=253.3, 6.1 Hz), 155.8, 141.1, 137.7, 134.1, 133.6 (t, J=10.4 Hz), 129.0, 128.5, 127.6, 127.3, 126.6, 122.7, 120.0, 112.4 (dd, J=19.9, 4.8 Hz), 109.8, 106.6 (t, J=17.2 Hz), 100.4, 74.3, 69.0, 48.8, 21.0. HRMS (ESI): calcd for $C_{25}H_{21}F_2N_2O$ $[M+H]^+$ 403.1616, found:403.1617.

Compound R1-17: lavender solid, yield 35%, mp 56-57° C. $^1$H NMR (400 MHz, DMSO-$d_6$) δ 7.72-7.60 (m, 1H), 7.44 (d, J=8.0 Hz, 1H), 7.40 (d, J=3.2 Hz, 1H), 7.32-7.23 (m, 5H), 7.21 (d, J=8.0 Hz, 2H), 6.85 (d, J=7.6 Hz, 1H), 6.43 (d, J=2.8 Hz, 1H), 5.44 (dd, J=10.0, 8.0 Hz, 1H), 5.38 (s, 2H), 4.80 (dd, J=10.4, 8.8 Hz, 1H), 4.17 (t, J=8.0 Hz, 1H), 2.37 (s, 3H). $^{13}$C NMR (100 MHz, DMSO-$d_6$) δ 160.2 (dd, J=253.3, 6.2 Hz), 155.8, 141.1, 137.7, 136.1, 133.5 (t, J=10.4 Hz), 130.3, 128.3, 127.2, 126.7, 126.1, 120.9, 120.2, 112.3 (dd, J=20.0, 4.3 Hz), 109.8, 106.6 (t, J=18.7 Hz), 100.8, 74.3, 69.0, 48.6, 21.5. HRMS (ESI): calcd for $C_{25}H_{21}F_2N_2O$ $[M+H]^+$ 403.1616, found: 403.1616.

Compound R1-18: yellow oil, yield 53%. $^1$H NMR (400 MHz, DMSO-$d_6$) δ 7.72-7.58 (m, 1H), 7.41 (d, J=8.0 Hz, 2H), 7.30-7.22 (m, 4H), 6.90 (t, J=7.8 Hz, 3H), 6.79 (d, J=7.2 Hz, 1H), 6.51 (d, J=2.0 Hz, 1H), 5.65 (s, 2H), 5.42 (t, J=9.2 Hz, 1H), 4.79 (t, J=9.2 Hz, 1H), 4.16 (t, J=8.4 Hz, 1H), 2.45 (s, 3H). $^{13}$C NMR (100 MHz, DMSO-$d_6$) δ 160.6 (dd, J=253.4, 6.2 Hz), 156.3, 141.3, 140.3, 134.9, 134.0 (t, J=10.4 Hz), 131.6, 130.0, 127.4, 126.0, 124.4, 121.2, 119.9, 119.2, 112.8 (dd, J=19.8, 5.0 Hz), 107.1 (t, J=18.5 Hz), 101.8, 74.8, 69.5, 51.6, 19.5. HRMS (ESI): calcd for $C_{25}H_{21}F_2N_2O$ $[M+H]^+$ 403.1616, found: 403.1616.

Compound R1-19: yellow-brown solid, yield 64%, mp melting point 106-107° C. $^1$H NMR (400 MHz, DMSO-$d_6$) δ 7.71-7.60 (m, 1H), 7.49 (d, J=7.6 Hz, 1H), 7.41 (d, J=8.0 Hz, 1H), 7.31-7.18 (m, 7H), 7.09 (t, J=7.6 Hz, 1H), 7.00 (t, J=7.4 Hz, 1H), 5.42 (dd, J=10.0, 8.0 Hz, 1H), 5.33 (s, 2H), 4.79 (dd, J=10.0, 8.4 Hz, 1H), 4.16 (t, J=8.0 Hz, 1H), 2.26 (s, 3H). $^{13}$C NMR (100 MHz, DMSO-$d_6$) δ 160.1 (dd, J=253.0, 6.3 Hz), 155.8, 141.1, 137.8, 136.0, 133.6 (t, J=10.3 Hz), 128.4, 127.4, 126.7, 126.4, 121.1, 118.6, 118.4, 112.3 (dd, J=20.0, 4.6 Hz), 109.8, 109.3, 106.6 (t, J=19.9 Hz), 74.3, 69.0, 48.5, 9.4. HRMS (ESI): calcd for $C_{25}H_{21}F_2N_2O$ $[M+H]^+$ 403.1616, found:403.1622.

Compound R1-20: light yellow solid, yield 64%, mp melting point 120-121° C. $^1$H NMR (400 MHz, DMSO-$d_6$) δ 7.71-7.61 (m, 1H), 7.57 (d, J=3.2 Hz, 1H), 7.37-7.19 (m, 7H), 7.11-7.05 (m, 1H), 6.80 (dd, J=10.8, 8.0 Hz, 1H), 6.56 (d, J=3.2 Hz, 1H), 5.51-5.36 (m, 3H), 4.80 (t, J=9.2 Hz, 1H), 4.17 (t, J=8.4 Hz, 1H). $^{13}$C NMR (100 MHz, DMSO-$d_6$) δ 160.6 (dd, J=252.7, 5.6 Hz), 156.3, 156.0 (d, J=244.3 Hz), 141.8, 138.9 (d, J=11.6 Hz), 137.7, 134.1 (t, J=10.4 Hz), 130.1, 127.9, 127.3, 122.3 (d, J=7.6 Hz), 117.3 (d, J=22.3 Hz), 112.9 (dd, J=18.8, 3.7 Hz), 107.4 (d, J=3.1 Hz), 107.1 (t, J=19.0 Hz), 104.3 (d, J=18.5 Hz), 97.1, 74.8, 69.4, 49.6. HRMS (ESI): calcd for $C_{24}H_{18}F_3N_2O$ $[M+H]^+$ 407.1366, found:407.1373.

Compound R1-21: red solid, yield 57%, mp melting point 70-71° C. $^1$H NMR (400 MHz, DMSO-$d_6$) δ 7.72-7.61 (m, 1H), 7.55 (dd, J=8.4, 5.6 Hz, 1H), 7.51 (d, J=3.2 Hz, 1H), 7.35 (dd, J=10.4, 2.0 Hz, 1H), 7.32-7.24 (m, 6H), 6.93-6.83 (m, 1H), 6.53-6.47 (m, 1H), 5.55-5.25 (m, 3H), 4.80 (dd, J=10.4, 8.8 Hz, 1H), 4.18 (t, J=8.0 Hz, 1H). $^{13}$C NMR (100 MHz, DMSO-$d_6$) δ 160.6 (dd, J=253.3, 6.2 Hz), 159.3 (d, J=234.4 Hz), 156.3, 141.8, 137.7, 136.2 (d, J=12.5 Hz), 134.1 (t, J=10.5 Hz), 130.2 (d, J=3.6 Hz), 128.0, 127.2, 125.4, 122.0 (d, J=10.1 Hz), 112.9 (dd, J=19.9, 4.8 Hz), 108.1 (d, J=24.4 Hz), 107.1 (t, J=18.6 Hz), 101.8, 97.0 (d, J=26.3 Hz), 74.8, 69.5, 49.3. HRMS (ESI): calcd for $C_{24}H_{18}F_3N_2O$ $[M+H]^+$ 407.1366, found: 407.1365.

Compound R1-22: light yellow solid, yield 49%. mp melting point 91-92° C. $^1$H NMR (400 MHz, DMSO-$d_6$) δ 7.71-7.65 (m, 1H), 7.61 (d, J=3.2 Hz, 1H), 7.49-7.43 (m, 1H), 7.35-7.20 (m, 7H), 6.95 (td, J=9.2, 2.4 Hz, 1H), 6.49 (d, J=2.8 Hz, 1H), 5.49-5.36 (m, 3H), 4.80 (dd, J=10.4, 8.8 Hz, 1H), 4.17 (t, J=8.4 Hz, 1H). $^{13}$C NMR (100 MHz, DMSO-$d_6$) δ 160.2 (dd, J=254.2, 5.3 Hz), 158.3, 155.9 (d, J=7.2 Hz), 141.3, 137.3, 133.5 (t, J=10.4 Hz), 132.4, 130.9, 128.5 (d, J=10.3 Hz), 127.3, 126.7, 112.3 (d, J=22.9 Hz), 111.1 (d, J=9.5 Hz), 109.3 (dd, J=26.2, 1.3 Hz), 106.6 (t, J=18.3 Hz), 105.0 (d, J=22.8 Hz), 101.0, 74.3, 69.0, 49.0. HRMS (ESI): calcd for $C_{24}H_{18}F_3N_2O$ $[M+H]^+$ 407.1366, found:407.1373.

Compound R1-23: red oil, yield 53%. $^1$H NMR (400 MHz, DMSO-$d_6$) δ 7.70-7.56 (m, 3H), 7.49 (d, J=8.8 Hz, 1H), 7.33-7.18 (m, 6H), 7.10 (d, J=8.8 Hz, 1H), 6.49 (s, 1H), 5.50-5.39 (m, 3H), 4.80 (t, J=9.2 Hz, 1H), 4.16 (t, J=8.4 Hz, 1H). $^{13}$C NMR (100 MHz, DMSO-$d_6$) δ 160.2 (dd, J=253.3, 6.2 Hz), 155.8, 141.3, 137.2, 134.2, 133.5 (t, J=10.4 Hz), 130.8, 129.4, 127.3, 126.7, 123.8, 121.1, 119.6, 112.3 (dd, J=24.4, 4.7 Hz), 111.7, 106.6 (t, J=18.4 Hz), 100.8, 74.3, 69.0, 49.0. HRMS (ESI): calcd for $C_{24}H_{18}ClF_2N_2O$ $[M+H]^+$ 423.1070, found:423.1075.

Compound R1-24: yellow oil, yield 64%. $^1$H NMR (400 MHz, DMSO-$d_6$) δ 7.75 (d, J=2.0 Hz, 1H), 7.70-7.60 (m, 1H), 7.58 (d, J=3.2 Hz, 1H), 7.45 (d, J=8.8 Hz, 1H), 7.34-7.13 (m, 7H), 6.49 (d, J=3.2 Hz, 1H), 5.48-5.35 (m, 3H), 4.79 (dd, J=10.2, 8.8 Hz, 1H), 4.16 (t, J=8.0 Hz, 1H). $^{13}$C NMR (100 MHz, DMSO-$d_6$) δ 160.2 (dd, J=253.3, 6.3 Hz), 155.9, 141.3, 137.2, 134.4, 133.5 (t, J=10.4 Hz), 130.6, 130.1, 127.3, 126.8, 123.6, 122.7, 112.3 (dd, J=19.9, 5.0 Hz), 112.2, 111.8, 106.6 (t, J=18.2 Hz), 100.7, 74.3, 69.0, 48.9. HRMS (ESI): calcd for $C_{24}H_{18}BrF_2N_2O$ $[M+H]^+$ 467.0565, found:467.0570.

Compound R1-25: yellow oil, yield 47%. $^1$H NMR (400 MHz, DMSO-$d_6$) δ 7.70-7.59 (m, 1H), 7.42 (d, J=8.8 Hz, 1H), 7.33 (d, J=3.2 Hz, 1H), 7.29-7.22 (m, 6H), 7.01 (d, J=2.0 Hz, 1H), 6.67 (dd, J=8.8, 2.0 Hz, 1H), 6.39 (d, J=3.2 Hz, 1H), 5.43 (dd, J=10.0, 8.0 Hz, 1H), 5.37 (s, 2H), 4.79 (dd, J=10.4, 8.8 Hz, 1H), 4.17 (t, J=8.4 Hz, 1H), 3.74 (s, 3H). $^{13}$C NMR (100 MHz, DMSO-$d_6$) δ 160.1 (dd, J=253.1, 6.2 Hz), 155.8, 155.6, 141.1, 137.6, 136.5, 133.6 (t, J=10.4 Hz), 127.7, 127.4, 126.7, 122.4, 121.0, 112.3 (dd, J=19.9, 4.6 Hz), 109.0, 106.6 (t, J=18.5 Hz), 101.0, 93.6, 74.4, 69.0, 55.3, 48.6. HRMS (ESI): calcd for $C_{25}H_{21}F_2N_2O_2$ $[M+H]^+$ 419.1566, found:419.1571.

Preparation of Compound R3-1

Step 1: 15.7 g of 2,6-difluorobenzamide and 44 mL of chloroacetaldehyde dimethyl acetal were added into a 200 mL single-necked flask, 6 mL of concentrated sulfuric acid was added dropwise with vigorous stirring in an ice water bath. The reaction mixture was stirring at room temperature, TLC was used for monitoring the reaction, and the reaction was finished after 10 hours. Water and dichloromethane were added, the mixture was poured into a separating funnel for separation, and the aqueous phase was extracted with dichloromethane for three times. The organic phases were combined, washed twice with water, once with saturated NaCl aqueous solution, dried by anhydrous sodium sulfate, filtered, concentrated under reduced pressure to remove dichloromethane and excessive chloroacetaldehyde dimethyl acetal (pumping on a diaphragm pump to generate solid), and recrystallized from normal hexane to obtain an intermediate B as a white solid with the yield of 87% and the melting point of 91-92° C.

Step 2: 2.5 g of intermediate B and 1.3 mL of anisole were added to a 100 mL single-necked flask and dissolved with stirring by adding 15 mL of methylene chloride. Under the ice-water bath 2.67 g of aluminum trichloride was slowly added with stirring, then the ice-water bath was removed, the reaction was stirred at room temperature and monitored by TLC (Petroleum ether/ethyl acetate=4/1), and the reaction was complete after 5 hours. The reaction mixture was slowly poured into an ice-water mixture to quench aluminum trichloride with stirring, then poured into a separatory funnel for separation, and the aqueous phase was extracted three times with dichloromethane. The combined organic phases were washed once with water and once with saturated aqueous NaCl solution, dried over anhydrous sodium sulfate and filtered, and the dichloromethane was removed by concentration under reduced pressure (suction on a diaphragm pump, solids appeared). Recrystallizing by using normal hexane obtained an intermediate C (containing an ortho-position Friedel-Crafts side product) as a white solid with the yield of 90%.

Step 3: a mixture of 1.63 g of intermediate C and the ortho-position Friedel-Crafts by-product was added into a 100 mL three-necked bottle, and 10 mL of redistilled dichloromethane was added to dissolve intermediate C. Cooling the reaction solution to −78° C., under the protection of argon, 1.2 mL of boron tribromide was slowly injected while stirring. Removing the low-temperature bath, stirring at room temperature, monitoring the reaction by TLC (petroleum ether/ethyl acetate=3/1), and the reaction was complete after 4 hours. Slowly pour the reaction liquid into an ice-water mixture to quench boron tribromide under stirring to obtain a yellow pasty solid mixed liquid. 30 mL of ethyl acetate was added and stirred at room temperature until the yellow solid disappeared. The mixture was poured into a separatory funnel for separation, and the aqueous phase was extracted three times with ethyl acetate. The combined organic phases were washed once with water and once with saturated sodium chloride, dried over anhydrous sodium sulfate and filtered, and concentrated under reduced pressure to remove ethyl acetate (suction on a diaphragm pump, appearance of solid). Recrystallizing by n-hexane obtained an intermediate D (which contains impurities after demethylation of the ortho-Friedel-crafts product) as a light yellow solid with the yield of 91%.

Step 4: 12.44 g of the mixture containing intermediate D and the demethylated by-products of the ortho-Friedel-crafts reaction was added to a 200 mL single-necked flask and 3.2 g of NaOH was added, and 50 mL of methanol was added under water bath to dissolve by stirring, and the mixture was reacted at room temperature. The reaction was monitored by TLC (petroleum ether/ethyl acetate=3/1) and after 1 hour the reaction was complete. The reaction solution was rotary evaporated, water and ethyl acetate were added for liquid separation, and the aqueous phase was extracted three times with ethyl acetate. The organic phases were combined and washed once by water, washed once by saturated sodium chloride, dried by anhydrous sodium sulfate and filtered, and then concentrated under reduced pressure to remove ethyl acetate (solid appears by pumping on a diaphragm pump), and the mixture was subjected to column chromatography, wherein eluent is petroleum ether and ethyl acetate with the volume ratio of 3:1, so that the compound shown as the formula (2-2) was obtained as a pale yellow solid, the yield is 51%, and the melting point is 157-158° C.

Step 5: 2 mmol of the compound represented by the formula (2-2) and 4 mmol of triethylamine were added to a 100 mL single-necked flask, and 10 mL of tetrahydrofuran was added to dissolve, 2.4 mmol of methanesulfonyl chloride dissolved in 5 mL of tetrahydrofuran was added dropwise with stirring, TLC (petroleum ether/ethyl acetate=3/1) was used to monitor the reaction, and after completion of the reaction, ethyl acetate and water were added for separation, and the aqueous phase was extracted three times with ethyl acetate. The organic phases were combined, washed once with saturated NaCl aqueous solution, dried by anhydrous sodium sulfate, filtered, concentrated under reduced pressure to remove ethyl acetate, and carried out column chromatography with an eluent (petroleum ether and ethyl acetate in a volume ratio of 5:1), and then recrystallized by normal hexane.

Compound R3-1: colorless transparent oily liquid, yield 71%. $^1$H NMR (400 MHz, DMSO-$d_6$) δ 7.75-7.62 (m, 1H), 7.44 (d, J=8.8 Hz, 2H), 7.39 (d, J=8.8 Hz, 2H), 7.30 (t, J=8.4 Hz, 2H), 5.55 (dd, J=10.4, 7.9 Hz, 1H), 4.86 (dd, J=10.3, 8.7 Hz, 1H), 4.24 (t, J=8.0 Hz, 1H), 3.39 (s, 3H). $^{13}$C NMR (100 MHz, DMSO-$d_6$) δ 160.1 (dd, J=253.6, 6.4 Hz), 156.2, 148.3, 141.2, 133.7 (t, J=10.4 Hz), 128.2, 122.5, 112.4 (dd, J=20.0, 4.8 Hz), 106.4 (t, J=18.0 Hz), 74.3, 68.6, 37.3. HRMS (ESI): calcd for $C_{16}H_{14}F_2NO_4S$ $[M+H]^+$354.0606, found 354.0605.

The synthesis of the compounds R3-2~R3-24 refers to the compound R3-1.

Compound R3-2: light yellow oily liquid, yield 70%. $^1$H NMR (400 MHz, DMSO-$d_6$) δ 7.71-7.63 (m, 1H), 7.43 (d, J=8.4 Hz, 2H), 7.36 (d, J=8.8 Hz, 2H), 7.29 (t, J=8.4 Hz, 2H), 5.54 (dd, J=10.4, 8.0 Hz, 1H), 4.86 (dd, J=10.4, 8.8 Hz, 1H), 4.23 (t, J=8.0 Hz, 1H), 3.52 (q, J=7.2 Hz, 2H), 1.38 (t, J=7.2 Hz, 3H). $^{13}$C NMR (100 MHz, DMSO-$d_6$) δ 160.6 (dd, J=253.5, 6.2 Hz), 156.7, 148.6, 141.6, 134.2 (t, J=10.4 Hz), 128.7, 122.9, 112.9 (dd, J=19.9, 4.8 Hz), 106.9 (t, J=18.5 Hz), 74.8, 69.0, 45.0, 8.5. HRMS (ESI): calcd for $C_{17}H_{16}F_2NO_4S$ $[M+H]^+$ 368.0763, found: 368.0759.

Compound R3-3: light yellow oily liquid, yield 83%. $^1$H NMR (400 MHz, DMSO-$d_6$) δ 7.72-7.63 (m, 1H), 7.44 (d, J=8.4 Hz, 2H), 7.37 (d, J=8.4 Hz, 2H), 7.30 (t, J=8.8 Hz, 2H), 5.56 (dd, J=9.6, 8.4 Hz, 1H), 4.87 (dd, J=10.0, 9.2 Hz, 1H), 4.24 (t, J=8.4 Hz, 1H), 3.51 (t, J=7.2 Hz, 2H), 1.91-1.80 (m, 2H), 1.04 (t, J=7.2 Hz, 3H). $^{13}$C NMR (100 MHz, DMSO-$d_6$) δ 160.2 (dd, J=253.2, 6.4 Hz), 156.2, 148.1, 141.1, 133.6 (t, J=10.4 Hz), 128.2, 122.4, 112.3 (dd, J=20.0, 4.4 Hz), 106.5 (t, J=18.4 Hz), 74.3, 68.6, 51.3, 16.9, 12.3. HRMS (ESI): calcd for $C_{18}H_{18}F_2NO_4S$ $[M+H]^+$ 382.0919, found: 382.0926.

Compound R3-4: colorless transparent oily liquid, yield 78%. $^1$H NMR (400 MHz, DMSO-$d_6$) δ 7.73-7.62 (m, 1H), 7.45 (d, J=8.8 Hz, 2H), 7.37 (d, J=8.8 Hz, 2H), 7.31 (t, J=8.4 Hz, 2H), 5.55 (dd, J=10.0, 8.0 Hz, 1H), 4.87 (dd, J=10.0, 8.8 Hz, 1H), 4.25 (t, J=8.4 Hz, 1H), 3.57-3.50 (m, 2H), 1.88-1.74 (m, 2H), 1.51-1.40 (m, 2H), 0.92 (t, J=7.2 Hz, 3H). $^{13}$C NMR (100 MHz, DMSO-$d_6$) δ 160.2 (dd, J=253.4, 6.1 Hz), 156.2, 148.2, 141.1, 133.6 (t, J=10.5 Hz), 128.2, 122.4, 112.4 (dd, J=20.2, 4.3 Hz), 106.5 (t, J=18.4 Hz), 74.3, 68.6, 49.4, 25.1, 20.6, 13.3. HRMS (ESI): calcd for $C_{19}H_{20}F_2NO_4S$ [M+H]$^+$ 396.1076, found: 396.1082.

Compound R3-5: colorless oily liquid, yield 60%. $^1$H NMR (400 MHz, DMSO-$d_6$) δ 7.74-7.61 (m, 1H), 7.43 (d, J=8.8 Hz, 2H), 7.34 (d, J=8.8 Hz, 2H), 7.30 (t, J=8.4 Hz, 2H), 5.54 (dd, J=10.0, 8.0 Hz, 1H), 4.86 (dd, J=10.0, 8.8 Hz, 1H), 4.24 (t, J=8.4 Hz, 1H), 3.59-3.49 (m, 1H), 2.20 (d, J=11.2 Hz, 2H), 1.83 (d, J=13.2 Hz, 2H), 1.67-1.52 (m, 3H), 1.42-1.32 (m, 2H), 1.26-1.16 (m, 1H). $^{13}$C NMR (100 MHz, DMSO-$d_6$) δ 160.7 (dd, J=253.6, 6.0 Hz), 156.7, 148.5, 141.4, 134.2 (t, J=10.4 Hz), 128.7, 122.8, 112.9 (dd, J=20.0, 4.8 Hz), 106.9 (d, J=8.0 Hz), 74.8, 69.1, 59.4, 26.6, 24.9, 24.6. HRMS (ESI): calcd for $C_{21}H_{22}F_2NO_4S$ [M+H]$^+$ 422.1232, found: 422.1240.

Compound R3-6: light yellow oily liquid, yield 79%. $^1$H NMR (400 MHz, DMSO-$d_6$) δ 7.80-7.60 (m, 1H), 7.42 (d, J=8.8 Hz, 2H), 7.37-7.26 (m, 4H), 7.22 (dd, J=10.0, 6.4 Hz, 1H), 6.39 (d, J=10.0 Hz, 1H), 6.30 (d, J=16.4 Hz, 1H), 5.53 (dd, J=10.0, 8.0 Hz, 1H), 4.85 (dd, J=10.0, 8.8 Hz, 1H), 4.23 (t, J=8.4 Hz, 1H). $^{13}$C NMR (100 MHz, DMSO-$d_6$) δ 160.1 (dd, J=253.6, 6.1 Hz), 156.3 148.2, 141.3, 133.7 (t, J=10.5 Hz), 133.4, 132.1, 128.2, 122.5, 112.4 (dd, J=20.0, 4.5 Hz), 106.5 (t, J=18.3 Hz), 74.3, 68.5. HRMS (ESI): calcd for $C_{17}H_{14}F_2NO_4S$ [M+H]$^+$ 366.0606, found: 366.0607.

Compound R3-7: white solid, yield 90%, melting point is 74-75° C. $^1$H NMR (400 MHz, DMSO-$d_6$) δ 7.98-7.94 (m, 2H), 7.72-7.63 (m, 1H), 7.57-7.50 (m, 2H), 7.35 (d, J=8.4 Hz, 2H), 7.29 (t, J=8.4 Hz, 2H), 7.08 (d, J=8.8 Hz, 2H), 5.50 (dd, J=10.0, 8.0 Hz, 1H), 4.83 (dd, J=10.4, 8.8 Hz, 1H), 4.18 (t, J=8.4 Hz, 1H). $^{13}$C NMR (100 MHz, DMSO-$d_6$) δ 167.3, 164.8, 160.6 (dd, J=253.6, 6.0 Hz), 156.8, 145.2 (d, J=672.4 Hz), 134.2 (t, J=10.4 Hz), 132.1 (d, J=10.0 Hz), 130.9 (d, J=3.2 Hz), 128.7, 122.8, 117.7 (d, J=23.2 Hz), 112.9 (dd, J=20. 0, 4.8 Hz), 106.8 (t, J=18.0 Hz), 74.7, 68.9. HRMS (ESI): calcd for $C_{21}H_{15}F_3NO_4S$ [M+H]$^+$ 434.0668. found: 434.0673.

Compound R3-8: light yellow solid, yield 88%, melting point 66-67° C. $^1$H NMR (400 MHz, DMSO-$d_6$) δ 7.89 (d, J=8.8 Hz, 2H), 7.76 (d, J=8.8 Hz, 2H), 7.77-7.63 (m, 1H), 7.35 (d, J=8.8 Hz, 2H), 7.29 (t, J=8.4 Hz, 2H), 7.09 (d, J=8.8 Hz, 2H), 5.50 (dd, J=10.0, 8.0 Hz, 1H), 4.83 (dd, J=10.4, 8.8 Hz, 1H), 4.18 (t, J=8.4 Hz, 1H). $^{13}$C NMR (100 MHz, DMSO-$d_6$) δ 161.4 (dd, J=253.5, 6.1 Hz), 157.4, 149.3, 142.7, 141.3, 134.9 (t, J=10.4 Hz), 134.3, 131.3, 131.2, 129.5, 123.5, 113.6 (dd, J=20.2, 4.4 Hz), 107.6 (t, J=18.3 Hz), 75.4, 69.7. HRMS (ESI): calcd for $C_{21}H_{15}ClF_2NO_4S$ [M+H]$^+$ 450.0373. found: 450.0365.

Compound R3-9: colorless oily liquid, yield 80%. $^1$H NMR (400 MHz, DMSO-$d_6$) δ 7.90 (d, J=8.4 Hz, 2H), 7.80 (d, J=8.8 Hz, 2H), 7.72-7.63 (m, 1H), 7.35 (d, J=8.8 Hz, 2H), 7.29 (t, J=8.4 Hz, 2H), 7.10 (d, J=8.4 Hz, 2H), 5.50 (dd, J=10.4, 8.0 Hz, 1H), 4.83 (dd, J=10.0, 8.8 Hz, 1H), 4.18 (t, J=8.4 Hz, 1H). $^{13}$C NMR (100 MHz, DMSO-$d_6$) δ 160.7 (dd, J=253.6, 6.0 Hz), 156.7, 148.6, 142.0, 134.2 (t, J=10.4 Hz), 134.0, 133.5, 130.6, 129.8, 128.8, 122.8, 112.9 (dd, J=20.0, 4.8 Hz), 106.9 (t, J=18.4 Hz), 74.7, 69.0. HRMS (ESI): calcd for $C_{21}H_{15}BrF_2NO_4S$ [M+H]$^+$ 493.9868. found: 493.9862.

Compound R3-10: yellow oily liquid, yield 85%. $^1$H NMR (400 MHz, DMSO-$d_6$) δ 8.06 (d, J=7.2 Hz, 2H), 7.71-7.65 (m, 1H), 7.61 (d, J=8.0 Hz, 2H), 7.35 (d, J=7.2 Hz, 2H), 7.29 (t, J=8.8 Hz, 2H), 7.09 (d, J=7.6 Hz, 2H), 5.52-5.46 (m, 1H), 4.85-4.80 (m, 1H), 4.18 (t, J=8.4 Hz, 1H). $^{13}$C NMR (100 MHz, DMSO-$d_6$) δ 160.1 (dd, J=253.6, 6.4 Hz), 156.3, 148.0, 141.4, 138.8, 133.7 (t, J=10.4 Hz), 129.6, 128.2, 122.3, 115.3, 112.4 (dd, J=20.0, 4.4 Hz), 106.3 (t, J=18.4 Hz), 104.0, 74.2, 68.4. HRMS (ESI): calcd for $C_{21}H_{15}F_2INO_4S$ [M+H]$^+$ 541.9729. found: 541.9728.

Compound R3-11: light white solid, yield 83%, melting point 50-51° C. $^1$H NMR (400 MHz, DMSO) δ 7.94-7.88 (m, 1H), 7.82-7.77 (m, 1H), 7.71-7.61 (m, 2H), 7.46-7.41 (m, 1H), 7.36 (d, J=8.8 Hz, 2H), 7.28 (t, J=8.4 Hz, 2H), 7.14 (d, J=8.4 Hz, 2H), 5.49 (dd, J=10.0, 8.0 Hz, 1H), 4.82 (dd, J=10.4, 8.8 Hz, 1H), 4.27-4.04 (m, 1H). $^{13}$C NMR (100 MHz, DMSO-$d_6$) δ 160.1 (dd, J=253.6, 6.4 Hz), 158.5 (d, J=257.6 Hz), 156.3, 148.0, 141.6, 138.2 (d, J=8.8 Hz), 133.7 (t, J=10.4 Hz), 131.1, 128.3, 125.5 (d, J=3.6 Hz), 122.2 (d, J=13.6 Hz), 121.9, 117.9 (d, J=20.4 Hz), 112.4 (dd, J=20.0, 4.8 Hz), 106.4 (t, J=18.4 Hz), 74.2, 68.5. HRMS (ESI): calcd for $C_{21}H_{15}F_3NO_4S$ [M+H]$^+$ 434.0668. found: 434.0674.

Compound R3-12: colorless oily liquid, yield 96%. $^1$H NMR (400 MHz, DMSO-$d_6$) δ 7.78 (d, J=8.0 Hz, 1H), 7.76-7.70 (m, 3H), 7.70-7.61 (m, 1H), 7.35 (d, J=8.8 Hz, 2H), 7.28 (t, J=8.4 Hz, 2H), 7.12 (d, J=8.8 Hz, 2H), 5.50 (dd, J=10.0, 8.0 Hz, 1H), 4.83 (dd, J=10.0, 8.8 Hz, 1H), 4.17 (t, J=8.4 Hz, 1H). $^{13}$C NMR (100 MHz, DMSO-$d_6$) δ 162.2 (d, J=250.0 Hz), 160.7 (dd, J=253.6, 6.2 Hz), 156.7, 148.6, 142.0, 136.6 (d, J=7.5 Hz), 134.2 (t, J=10.4 Hz), 132.7 (d, J=8.2 Hz), 128.7, 125.1 (d, J=2.8 Hz), 122.9 (d, J=21.5 Hz), 122.7, 115.8 (d, J=25.2 Hz), 112.9 (dd, J=19.9, 4.8 Hz), 106.9 (t, J=18.4 Hz), 74.7, 69.0. HRMS (ESI): calcd for $C_{21}H_{15}F_3NO_4S$ [M+H]$^+$ 434.0668. found: 434.0669.

Compound R3-13: colorless oily liquid, yield 90%. $^1$H NMR (400 MHz, DMSO-$d_6$) δ 8.12 (d, J=8.4 Hz, 2H), 8.07 (d, J=8.4 Hz, 2H), 7.72-7.63 (m,1H), 7.36 (d, J=8.8 Hz, 2H), 7.29 (t, J=8.4 Hz, 2H), 7.12 (d, J=8.8 Hz, 2H), 5.50 (dd, J=10.0, 8.4 Hz, 1H), 4.83 (dd, J=10.0, 8.8 Hz, 1H), 4.18 (t, J=8.4 Hz, 1H). $^{13}$C NMR (100 MHz, DMSO-$d_6$) δ 160.2 (dd, J=253.7, 6.1 Hz), 156.2, 148.0, 141.7, 138.2, 134.3(q, J=32.3 Hz), 133.7 (t, J=10.4 Hz), 129.3, 128.3, 127.0 (q, J=3.6 Hz), 125.9 (q, J=278 Hz), 122.3, 112.4 (dd, J=20.0, 4.5 Hz), 106.4 (t, J=18.4 Hz), 74.2, 68.5. HRMS (ESI): calcd for $C_{22}H_{15}F_5NO_4S$ [M+H]$^+$ 484.0636. found: 484.0641.

Compound R3-14: light yellow solid, yield 87%, melting point 80-81° C. $^1$H NMR (400 MHz, DMSO-$d_6$) δ 7.91-7.84 (m, 1H), 7.82-7.75 (m, 1H), 7.72-7.63 (m, 1H), 7.39-7.26 (m, 5H), 7.16 (d, J=8.0 Hz, 2H), 5.50 (dd, J=10.0, 8.0 Hz, 1H), 4.83 (dd, J=10.4, 8.8 Hz, 1H), 4.18 (t, J=8.4 Hz, 1H). $^{13}$C NMR (100 MHz, DMSO-$d_6$) δ 166.6 (dd, J=257.4, 12.0 Hz), 160.2 (dd, J=253.5, 6.2 Hz), 159.6 (dd, J=259.7, 14.1 Hz), 156.2, 147.9, 141.7, 133.7 (t, J=10.5 Hz), 133.4 (d, J=11.5 Hz), 128.4, 122.0, 119.0 (dd, J=13.9, 3.7 Hz), 113.2 (dd, J=22.7, 3.6 Hz), 112.4 (dd, J=20.0, 4.5 Hz), 107.0 (dd, J=27.2, 24.9 Hz), 106.4 (t, J=18.2 Hz), 74.2, 68.5. HRMS (ESI): calcd for $C_{21}H_{14}F_4NO_4S$ [M+H]$^+$ 452.0574, found: 452.0579.

Compound R3-15: light yellow solid, yield 83%, melting point 72-73° C. $^1$H NMR (400 MHz, DMSO-$d_6$) δ 7.72-7.62 (m, 2H), 7.59-7.51 (m, 1H), 7.36 (d, J=8.8 Hz, 2H), 7.29 (t, J=8.8 Hz, 2H), 7.22 (d, J=8.4 Hz, 2H), 5.51 (dd, J=10.0, 8.0 Hz, 1H), 4.83 (dd, J=10.0, 9.2 Hz, 1H), 4.18 (t, J=8.4 Hz, 1H). $^{13}$C NMR (100 MHz, DMSO-$d_6$) δ 160.6 (dd, J=253.5, 6.2 Hz), 156.7, 155.3 (ddd, J=258.8, 10.0, 3.3 Hz), 148.9 (ddd, J=260.8, 11.7, 4.3 Hz), 148.4, 142.4, 140.7 (dt, J=252.3Hz, 14.9Hz), 134.2 (t, J=10.5 Hz), 128.9, 126.6 (dd, J=9.8, 4.1 Hz), 122.8, 120.5 (dd, J=11.1, 3.5 Hz), 114.4 (dd, J=18.6, 3.5 Hz), 112.9 (dd, J=19.8, 4.8 Hz), 106.9 (t, J=18.3 Hz), 74.7, 69.0. HRMS (ESI): calcd for $C_{21}H_{13}F_5NO_4S$ $[M+H]^+$ 470.0480, found: 470.0479.

Compound R3-16: light yellow solid, yield 80%, melting point 69-70° C. $^1$H NMR (400 MHz, DMSO-$d_6$) δ 7.76 (d, J=8.0 Hz, 2H), 7.72-7.62 (m, 1H), 7.48 (d, J=8.0 Hz, 2H), 7.35-7.26 (m, 4H), 7.06 (d, J=8.4 Hz, 2H), 5.52-5.46 (m, 1H), 4.86-4.79 (m, 1H), 4.20-4.15 (m, 1H), 2.42 (s, 3H). $^{13}$C NMR (100 MHz, DMSO-$d_6$) δ 160.6 (dd, J=253.6, 6.0 Hz), 156.7, 148.7, 146.3, 141.7, 134.2 (t, J=10.4 Hz), 131.9, 130.7, 128.7, 128.6, 122.7, 112.9 (dd, J=20.0, 4.4 Hz), 106.9 (t, J=18.4 Hz), 74.7, 69.0, 21.62. HRMS (ESI): calcd for $C_{22}H_{18}F_2NO_4S$ $[M+H]^+$ 430.0919, found: 430.0925.

Compound R3-17: colorless oily liquid, yield 94%. $^1$H NMR (400 MHz, DMSO-$d_6$) δ 7.82 (d, J=8.4 Hz, 2H), 7.71 (d, J=8.4 Hz, 2H), 7.72-7.63 (m, 1H), 7.34 (d, J=8.4 Hz, 2H), 7.29 (t, J=8.4 Hz, 2H), 7.08 (d, J=8.4 Hz, 2H), 5.50 (dd, J=10.0, 8.0 Hz, 1H), 4.83 (dd, J=10.0, 8.8 Hz, 1H), 4.19 (t, J=8.4 Hz, 1H), 1.32 (s, 9H). $^{13}$C NMR (100 MHz, DMSO-$d_6$) δ 160.6 (dd, J=253.6, 6.4 Hz), 158.8, 156.7, 148.7, 141.7, 134.2(t, J=10.4 Hz), 132.0, 128.6, 128.5, 127.2 122.7, 112.9 (dd, J=20.0, 4.4 Hz), 106.9 (t, J=17.6 Hz), 74.7, 69.0, 35.6, 31.1. HRMS (ESI): calcd for $C_{25}H_{24}F_2NO_4S$ $[M+H]^+$ 472.1389, found: 472.1394.

Compound R3-18: white solid, yield 22%, melting point 52-53° C. $^1$H NMR (400 MHz, DMSO-$d_6$) δ 7.72-7.63 (m, 1H), 7.39-7.25 (m, 6H), 7.13-7.08 (m, 3H), 5.51 (dd, J=10.0, 8.0 Hz, 1H), 4.84 (dd, J=10.0, 8.8 Hz, 1H), 4.40-4.36 (m, 2H), 4.35-4.30 (m, 2H), 4.19 (t, J=8.4 Hz, 1H). $^{13}$C NMR (100 MHz, DMSO) δ 160.6 (dd, J=253.6, 6.1 Hz), 156.7, 149.4, 148.8, 144.1, 141.7, 134.2 (t, J=10.5 Hz), 128.6, 126.6, 122.8, 122.5, 118.6, 117.5, 112.9 (dd, J=19.8, 4.8 Hz), 106.9 (t, J=18.4 Hz), 74.7, 69.0, 65.0, 64.5. HRMS (ESI): calcd for $C_{23}H_{18}F_2NO_6S$ $[M+H]^+$ 474.0817, found: 474.0821.

Compound R3-19: light white solid, yield 44%, melting point 52-53° C. $^1$H NMR (400 MHz, DMSO-$d_6$) δ 10.54 (s, 1H), 7.89 (d, J=9.2 Hz, 2H), 7.83 (d, J=9.2 Hz, 2H), 7.71-7.63 (m, 1H), 7.36 (d, J=8.4 Hz, 2H), 7.31-7.25 (m, 2H), 7.09 (d, J=8.4 Hz, 2H), 5.52 (dd, J=10.0, 8.0 Hz, 1H), 4.85 (dd, J=10.4, 8.8 Hz, 1H), 4.23-4.17 (m, 1H), 2.14 (s, 3H). $^{13}$C NMR (100 MHz, DMSO-$d_6$) δ 170.0, 160.6 (dd, J=253.6, 6.0 Hz), 156.8, 148.8, 145.3, 141.6, 134.1 (t, J=10.4 Hz), 130.1, 128.5, 127.8, 122.8, 119.3, 112.8 (dd, J=20.0, 4.4 Hz), 106.8 (t, J=18.4 Hz), 74.7, 69.0, 24.6. HRMS (ESI): calcd for $C_{23}H_{19}F_2N_2O_5S$ $[M+H]^+$ 473.0977, found: 473.0978.

Compound R3-20: colorless oily liquid, yield 75%. $^1$H NMR (400 MHz, DMSO-$d_6$) δ 8.66 (d, J=8.4 Hz, 1H), 8.42 (d, J=8.4 Hz, 1H), 8.22 (d, J=8.4 Hz, 1H), 8.12 (d, J=7.2 Hz, 1H), 7.95-7.89 (m, 1H), 7.83-7.77 (m, 1H), 7.68-7.63 (m, 2H), 7.32-7.21 (m, 4H), 6.91 (d, J=6.8 Hz, 2H), 5.45-5.39 (m, 1H), 4.81-4.75 (m, 1H), 4.14-4.10 (m, 1H). $^{13}$C NMR (100 MHz, DMSO-$d_6$) δ 160.6 (dd, J=253.7, 6.1 Hz), 156.7, 148.7, 141.8, 136.9, 134.2, 134.1 (t, J=10.4 Hz), 131.8, 130.1, 130.0, 129.9, 128.7, 128.11, 128.05, 125.1, 124.5, 122.3, 112.8 (dd, J=20.3, 4.3 Hz), 106.9 (t, J=18.4 Hz), 74.6, 69.0. HRMS (ESI): calcd for $C_{25}H_{18}F_2NO_4S$ $[M+H]^+$ 466.0919, found: 466.0925.

Compound R3-21: colorless oily liquid, yield 76%. $^1$H NMR (400 MHz, DMSO-$d_6$) δ 8.58 (d, J=1.2 Hz, 1H), 8.23 (t, J=7.2 Hz, 2H), 8.12 (d, J=8.4 Hz, 1H), 7.90 (dd, J=8.8, 2.0 Hz, 1H), 7.84-7.77 (m, 1H), 7.71 (t, J=7.2 Hz, 1H), 7.70-7.61 (m, 1H), 7.35-7.22 (m, 4H), 7.08 (d, J=8.8 Hz, 2H), 5.45 (dd, J=10.0, 8.0 Hz, 1H), 4.80 (dd, J=10.0, 8.8 Hz, 1H), 4.14 (t, J=8.4 Hz, 1H). $^{13}$C NMR (100 MHz, DMSO-$d_6$) δ 160.1 (dd, J=253.6, 6.2 Hz), 156.2, 148.3, 141.3, 135.0, 133.7 (t, J=10.6 Hz), 131.4, 131.3, 130.2, 130.0, 130.0, 129.6, 128.2, 128.1, 128.0, 122.4, 122.3, 112.4 (dd, J=20.3, 4.3 Hz), 106.4 (t, J=18.6 Hz), 74.2, 68.5. HRMS (ESI): calcd for $C_{25}H_{18}F_2NO_4S$ $[M+H]^+$ 466.0919, found: 466.0924.

Compound R3-22: yellow solid, yield 85%, melting point 107-108° C. $^1$H NMR (400 MHz, $CDCl_3$) δ 7.95 (d, J=8.4 Hz, 2H), 7.83 (d, J=8.4 Hz, 2H), 7.53-7.38 (m, 1H), 7.30 (d, J=8.8 Hz, 2H), 7.06-6.94 (m, 4H), 5.45 (dd, J=10.0, 8.4 Hz, 1H), 4.82 (dd, J=10.0, 8.8 Hz, 1H), 4.23 (t, J=8.4 Hz, 1H). $^{13}$C NMR (100 MHz, $CDCl_3$) δ 156.4 (dd, J=256.4, 5.9 Hz), 153.4, 143.9, 136.7, 134.6, 128.2, 128.0 (t, J=10.4 Hz), 124.4, 123.6, 117.8, 113.3, 112.1, 107.3 (dd, J=20.3, 5.2 Hz), 102.1 (t, J=17.5 Hz), 69.8, 64.7. HRMS (ESI): calcd for $C_{22}H_{15}F_2N_2O_4S$ $[M+H]^+$ 441.0715, found: 441.0717.

Compound R3-23: light yellow solid, yield 77%, melting point 131-132° C. $^1$H NMR (400 MHz, DMSO-$d_6$) δ 8.47 (d, J=8.8 Hz, 2H), 8.18 (d, J=8.8 Hz, 2H), 7.73-7.62 (m, 1H), 7.36 (d, J=8.4 Hz, 2H), 7.29 (t, J=8.8 Hz, 2H), 7.13 (d, J=8.8 Hz, 2H), 5.51 (dd, J=10.0, 8.0 Hz, 1H), 4.84 (dd, J=10.4, 8.8 Hz, 1H), 4.19 (t, J=8.4 Hz, 1H). $^{13}$C NMR (100 MHz, DMSO-$d_6$) δ 160.2 (dd, J=253.6, 6.1 Hz), 156.3, 151.1, 148.0, 141.7, 139.5, 133.7 (t, J=10.2 Hz), 130.0, 128.4, 125.0, 122.3, 112.4 (dd, J=20.2, 4.1 Hz), 106.3 (d, J=18.3 Hz), 74.2, 68.5. HRMS (ESI): calcd for $C_{21}H_{15}F_2N_2O_6S$ $[M+H]^+$ 461.0613, found: 461.0618.

Compound R3-24: white solid, yield 71%, melting point 167-168° C. $^1$H NMR (400 MHz, DMSO-$d_6$) δ 7.73-7.64 (m, 1H), 7.58-7.50 (m, 4H), 7.30 (t, J=8.4 Hz, 2H), 5.59 (dd, J=10.0, 8.0 Hz, 1H), 4.88 (dd, J=10.4, 8.8 Hz, 1H), 4.29-4.22 (m, 1H). $^{13}$C NMR (100 MHz, DMSO-$d_6$) δ 160.7 (dd, J=253.6, 6.1 Hz), 157.0, 148.9, 143.5, 134.2 (t, J=10.5 Hz), 129.3, 122.2, 118.7 (q, J=319 Hz), 112.9 (dd, J=20.3, 4.3 Hz), 106.9 (t, J=18.3 Hz), 74.7, 68.9. HRMS (ESI): calcd for $C_{16}H_{11}F_5NO_4S$ [M+H]+ 408.0323, found: 408.0328.

Preparation of Compound III-4

33.4 g of the compound represented by the formula (3-1) was charged into a 200 mL single-necked flask, and 17.8 g of the compound represented by the formula (III-2) and 8.0 g of sodium hydroxide and 64 mL of methanol were added, and the mixture was stirred at room temperature for 43 hours under an argon atmosphere. After rotary evaporation, the mixture was separated by addition of dichloromethane and water, and the aqueous phase was extracted three times with dichloromethane. The organic phases were combined, washed once with a saturated ammonium chloride solution and once with a saturated sodium chloride solution, dried over anhydrous sodium sulfate, filtered and concentrated under reduced pressure to remove the dichloromethane. Column chromatography gave 34.9 g of pale yellow solid (compound represented by formula (III-4)), yield 88%, melting point 52-53° C.

$^1$H NMR (400 MHz, $CDCl_3$) δ 8.50 (s, 1H), 8.04 (d, J=7.8 Hz, 1H), 7.66 (d, J=7.7 Hz, 1H), 7.53 (t, J=7.5 Hz, 1H), 7.49-7.41 (m, 4H), 7.37 (d, J=8.1 Hz, 2H), 7.00 (t, J=8.3 Hz, 2H), 5.50 (dd, J=10.2, 8.1 Hz, 1H), 5.24 (s, 2H), 4.84 (dd, J=10.3, 8.5 Hz, 1H), 4.31 (t, J=8.2 Hz, 1H). 13C NMR (100 MHz, $CDCl_3$) δ 161.8 (dd, J=254 Hz, 5 Hz), 158.2 (s), 146.3 (s), 142.3 (s), 137.3 (s), 133.0 (t, J=10.0 Hz), 132.5 (s), 130.9 (s), 130.0 (s), 129.5 (s), 129.0 (s), 128.8 (s), 128.6 (s), 128.3 (q, J=31.1 Hz), 127.9 (s), 127.4 (s), 126.4 (q, J=272 Hz), 112.5 (dt, J=20.0, 2.0 Hz), 108.1 (t, J=18.0 Hz), 77.0 (s), 75.4 (s), 70.6 (s). HRMS (ESI): calcd for $C_{24}H_{18}F_5N_2O_2$ $[M+H]^+$ 461.1283, found: 461.1280.

Alternatively, a 500 mL single-necked flask was charged with the compound represented by the formula (2-1) (0.02 mol, 1.0 equiv), anhydrous potassium carbonate (0.024 mol, 1.2 equiv), potassium iodide (0.004 mol, 0.2 equiv), o-trifluoromethylbenzaldoxime (1.05 equiv), and 100 mL acetonitrile. The reaction was carried out for 3 hours at 50° C. under argon. Water and ethyl acetate were added for separation, and the aqueous phase was extracted three times with ethyl acetate. The organic phases were combined, washed with 10 wt % $NaHCO_3$, water, brine, dried over anhydrous sodium sulfate and desolventized to obtain 8.39 g of yellow solid (compound III-4) with a yield of 91%.

Preparation of Compound III-5

19.4 g of the compound represented by the formula (3-1) was put into a 500 mL single-necked flask, 2.4 g of sodium hydroxide and 100 mL of acetonitrile were added. The reaction was carried out at room temperature for 12 hours, then 8.5 g of 2-mercaptobenzothiazole and 2.4 g of sodium hydroxide were added. The reaction was carried out at room temperature for 6 hours, water and ethyl acetate were added for liquid separation, the aqueous phase was extracted three times with ethyl acetate. The organic phases were combined, successively washed with 10% $NaHCO_3$, water, and salt, then dried over anhydrous sodium sulfate and subjected to column chromatography to obtain 19.0 g of a yellow solid (compound III-5), yield 87%, and melting point 92-94° C.

$^1H$ NMR (400 MHz, $CDCl_3$) δ 7.91 (d, J=8.0 Hz, 1H), 7.76 (d, J=8.0 Hz, 1H), 7.48 (d, J=8.4 Hz, 2H), 7.46-7.41 (m, 3H), 7.32 (d, J=8.4 Hz, 2H), 7.00 (t, J=8.0 Hz, 2H), 5.46 (dd, J=10.4, 8.4 Hz, 1H), 4.81 (dd, J=10.4, 8.4 Hz, 1H), 4.61 (s, 2H), 4.29 (t, J=8.4 Hz, 1H); $^{13}C$ NMR (100 MHz, $CDCl_3$) δ66.3, 161.2 (dd, J=254.8, 6.0 Hz), 157.7, 153.2, 141.4, 135.8, 135.4, 132.5 (t, J=10.4 Hz), 129.6, 127.1, 126.1, 124.3, 121.6, 121.0, 112.0 (dd, J=22.8, 2.6 Hz), 107.2 (t, J=17.4 Hz), 74.7, 70.0, 37.4; HRMS (ESI) calcd for $C_{23}H_{17}F_2N_2OS_2$ $[M+H]^+$ 439.0745, found 439.0739.

Alternatively, a 500 mL single-necked flask was charged with the compound represented by the formula (2-1) (0.02 mol, 1.0 equiv), anhydrous potassium carbonate (0.024 mol, 1.2 equiv), potassium iodide (0.004 mol, 0.2 equiv), 2-mercaptobenzothiazole (0.021 mol, 1.05 equiv), and 100 mL acetonitrile. The reaction was carried out for 3 hours at 50° C. under argon. Water and ethyl acetate were added for separation, and the aqueous phase was extracted three times with ethyl acetate. The organic phases were combined, successively washed by 10 wt % $NaHCO_3$, water, and salt, then dried by anhydrous sodium sulfate and desolventized to obtain 8.06 g of yellow solid (compound III-5) with the yield of 92%.

Assay Example 1

The assay examples are used to illustrate the acaricidal activity against *Tetranychus cinnabarinus* (mortality of mite larvae and mortality of mite eggs) of the compounds having the structure represented by formula (I), and the results are shown in tables 1 to 9, where mortality of mite larvae % =(number of dead mite larvae applied/total number of mite larvae applied)×100, and mortality of mite eggs %= (number of dead mite eggs applied/total number of mite eggs applied)×100.

Testing the Larvicidal Activity

Tetranychus cinnabarinus bred indoors on bean seedlings was used as a test subject by the dipping method. Move adult mites onto the newly grown complete bean seedling leaves with two leaves, cut off the bean seedlings, place the bean seedlings in a greenhouse with illumination at 25° C. for laying eggs for 24 hours, then remove adult mites and keep mite eggs. And continuously culture in the greenhouse for 5 days until mite eggs hatch into mite larvae (ensuring that the number of the mites on each tested leaf is not less than 60).

Completely immerse the bean seedling leaves containing the mite larvae into the sample solution to be detected with Tween at the prepared concentration for 5-6 seconds by using tweezers, slightly throw off residual liquid, put the bean seedling leaves back to the culture cup, continuously culture for 4 days and check the result. One of the plants was immersed in a solution containing no sample to be tested and the remaining additives were identical to the sample solution as a blank control. Each compound was replicated three times.

Testing the Activity of the Acaricidal Eggs

Tetranychus cinnabarinus bred indoors on bean seedlings was used as a test subject by the dipping method. Move female adult mites onto the newly grown complete bean seedling leaves with two leaves, cut off the bean seedlings, place the bean seedlings in a greenhouse with illumination at 25° C. for laying eggs for 24 hours, then remove adult mites and keep mite eggs. After continuously culturing in the greenhouse for one day, completely soak the bean seedling leaves containing the acarid eggs into the prepared sample solution to be tested for 5-6 seconds by using tweezers, slightly throw off residual liquid, put the bean seedling leaves back to the culture cup, continuously culture for 4 days and then check the result. One of the plants was immersed in a solution containing no sample to be tested and the remaining additives were identical to the sample solution as a blank control. Each compound was replicated three times.

TABLE 1 the acaricidal activity test result of the oxazoline compounds with the formula (R1-1~R1-25) is as follows:

| NO. | mortality of mite larvae (%) | | | | | mortality of mite eggs (%) | | | | |
|---|---|---|---|---|---|---|---|---|---|---|
| (mg/L) | 200 | 100 | 10 | 1 | 0.1 | 200 | 100 | 10 | 1 | 0.1 |
| R1-1 | 70 | 50 | — | — | — | 95 | 70 | 60 | 30 | — |
| R1-2 | 90 | 75 | 35 | — | — | 95 | 80 | 55 | — | — |
| R1-3 | 100 | 95 | 70 | 55 | — | 100 | 90 | 70 | 55 | — |
| R1-4 | 90 | 70 | 30 | — | — | 90 | 70 | 50 | — | — |
| R1-5 | 100 | 90 | 40 | — | — | 100 | 100 | 45 | — | — |
| R1-6 | 100 | 100 | 70 | 50 | — | 100 | 100 | 70 | 50 | — |
| R1-7 | 100 | 90 | 60 | 30 | — | 100 | 90 | 70 | 60 | — |
| R1-8 | 100 | 95 | 65 | 35 | — | 100 | 95 | 40 | — | — |

TABLE 1-continued the acaricidal activity test result of the oxazoline compounds with the formula (R1-1~R1-25) is as follows:

| NO. | mortality of mite larvae (%) | | | | | mortality of mite eggs (%) | | | | |
|---|---|---|---|---|---|---|---|---|---|---|
| (mg/L) | 200 | 100 | 10 | 1 | 0.1 | 200 | 100 | 10 | 1 | 0.1 |
| R1-9 | 85 | 80 | 35 | — | — | 95 | 70 | 50 | — | — |
| R1-10 | 100 | 100 | 95 | 80 | 70 | 100 | 100 | 90 | 85 | 75 |
| R1-11 | 100 | 85 | 70 | 30 | — | 100 | 100 | 75 | 55 | — |
| R1-12 | 100 | 70 | 40 | — | — | 90 | 80 | 50 | — | — |
| R1-13 | 100 | 88 | 70 | 40 | — | 100 | 100 | 90 | 60 | — |
| R1-14 | 100 | 95 | 70 | 30 | — | 100 | 95 | 70 | 40 | — |
| R1-15 | 100 | 100 | 90 | 80 | 65 | 100 | 100 | 100 | 90 | 80 |
| R1-16 | 100 | 100 | 65 | 50 | — | 100 | 100 | 70 | 50 | — |
| R1-17 | 100 | 100 | 40 | 20 | — | 100 | 100 | 65 | 40 | — |
| R1-18 | 100 | 100 | 100 | 85 | 75 | 100 | 100 | 100 | 80 | 75 |
| R1-19 | 100 | 100 | 85 | 70 | 65 | 100 | 100 | 90 | 80 | 75 |
| R1-20 | 100 | 100 | 70 | 45 | — | 100 | 100 | 80 | 60 | — |
| R1-21 | 100 | 100 | 60 | — | — | 100 | 100 | 70 | 30 | — |
| R1-22 | 100 | 100 | 85 | 80 | 70 | 100 | 98 | 90 | 85 | 75 |
| R1-23 | 100 | 100 | 80 | 50 | — | 100 | 100 | 75 | 60 | — |
| R1-24 | 100 | 100 | 60 | — | — | 100 | 100 | 80 | 40 | — |
| R1-25 | 80 | 70 | 20 | — | — | 100 | 90 | 65 | 40 | — |
| Etoxazole | 100 | 100 | 90 | 80 | 65 | 100 | 100 | 90 | 70 | 60 |

TABLE 2 the acaricidal activity test results of oxazoline derivatives with formula R2-1~R2-24:

| NO. | mortality of mite larvae (%) | | | | | mortality of mite eggs (%) | | | | |
|---|---|---|---|---|---|---|---|---|---|---|
| mg/L | 200 | 100 | 10 | 1 | 0.1 | 200 | 100 | 10 | 1 | 0.1 |
| R2-1 | 100 | 100 | 100 | 85 | 50 | 100 | 100 | 100 | 97 | 60 |
| R2-2 | 100 | 100 | 90 | 90 | 80 | 100 | 100 | 100 | 95 | 85 |
| R2-3 | 100 | 100 | 97 | 95 | 90 | 100 | 100 | 100 | 100 | 85 |
| R2-4 | 100 | 100 | 92 | 85 | 70 | 100 | 100 | 98 | 90 | 70 |
| R2-5 | 100 | 100 | 100 | 95 | 90 | 100 | 100 | 100 | 97 | 90 |
| R2-6 | 100 | 100 | 100 | 90 | 80 | 100 | 100 | 100 | 100 | 95 |
| R2-7 | 100 | 100 | 90 | 75 | 40 | 100 | 100 | 95 | 90 | 70 |
| R2-8 | 100 | 100 | 92 | 80 | 50 | 100 | 100 | 90 | 80 | 60 |
| R2-9 | 100 | 95 | 75 | 30 | — | 100 | 100 | 85 | 55 | — |
| R2-10 | 95 | 80 | 62 | — | — | 100 | 100 | 75 | — | — |
| R2-11 | 100 | 100 | 80 | 70 | — | 100 | 100 | 90 | 75 | — |
| R2-12 | 100 | 100 | 95 | 50 | — | 100 | 100 | 90 | 65 | — |
| R2-13 | 100 | 100 | 95 | 60 | — | 100 | 100 | 85 | 80 | 70 |
| R2-14 | 90 | 65 | — | — | — | 100 | 100 | 50 | — | — |
| R2-15 | 100 | 80 | 60 | — | — | 100 | 100 | 70 | — | — |
| R2-16 | 88 | 50 | — | — | — | 100 | 100 | 50 | — | — |
| R2-17 | 90 | 60 | — | — | — | 100 | 100 | 70 | — | — |
| R2-18 | 100 | 100 | 88 | 80 | 70 | 100 | 100 | 96 | 90 | 85 |
| R2-19 | 100 | 100 | 90 | 88 | 85 | 100 | 100 | 100 | 90 | 90 |
| R2-20 | 100 | 92 | 80 | 40 | — | 100 | 100 | 90 | 60 | — |
| R2-21 | 100 | 99 | 80 | 50 | — | 100 | 100 | 97 | 80 | 60 |
| R2-22 | 100 | 96 | 88 | 55 | — | 100 | 100 | 100 | 90 | 80 |
| R2-23 | 100 | 100 | 95 | 80 | 75 | 100 | 90 | 90 | 85 | 75 |
| R2-24 | 100 | 100 | 100 | 100 | 85 | 100 | 100 | 95 | 80 | 70 |

TABLE 3 the acaricidal activity test results of oxazoline derivatives with formula R3-1~R3-24:

| NO. | mortality of mite larvae (%) | | | | | mortality of mite eggs (%) | | | | |
|---|---|---|---|---|---|---|---|---|---|---|
| (mg/L) | 200 | 100 | 10 | 1 | 0.1 | 200 | 100 | 10 | 1 | 0.1 |
| R3-1 | 100 | 100 | 100 | 80 | 50 | 100 | 95 | 90 | 70 | — |
| R3-2 | 100 | 100 | 90 | 60 | — | 100 | 95 | 80 | 50 | — |
| R3-3 | 100 | 100 | 100 | 100 | 80 | 100 | 100 | 100 | 90 | 50 |
| R3-4 | 100 | 100 | 100 | 90 | 60 | 100 | 95 | 85 | 60 | — |
| R3-5 | 100 | 100 | 90 | 60 | — | 100 | 100 | 90 | 70 | — |

TABLE 3-continued the acaricidal activity test results of oxazoline derivatives with formula R3-1~R3-24:

| NO. | mortality of mite larvae (%) | | | | | mortality of mite eggs (%) | | | | |
|---|---|---|---|---|---|---|---|---|---|---|
| (mg/L) | 200 | 100 | 10 | 1 | 0.1 | 200 | 100 | 10 | 1 | 0.1 |
| R3-6 | 100 | 80 | 80 | 60 | — | 100 | 80 | 60 | — | — |
| R3-7 | 100 | 100 | 90 | 50 | — | 100 | 100 | 90 | 60 | — |
| R3-8 | 100 | 100 | 98 | 85 | 60 | 100 | 95 | 90 | 70 | — |
| R3-9 | 100 | 100 | 100 | 100 | 70 | 100 | 100 | 90 | 75 | 30 |
| R3-10 | 100 | 100 | 88 | 65 | — | 100 | 100 | 85 | 60 | — |

TABLE 3-continued the acaricidal activity test results of oxazoline derivatives with formula R3-1~R3-24:

| NO. | mortality of mite larvae (%) | | | | | mortality of mite eggs (%) | | | | |
|---|---|---|---|---|---|---|---|---|---|---|
| (mg/L) | 200 | 100 | 10 | 1 | 0.1 | 200 | 100 | 10 | 1 | 0.1 |
| R3-11 | 100 | 100 | 90 | 80 | 50 | 100 | 95 | 80 | 50 | — |
| R3-12 | 100 | 100 | 90 | 50 | — | 100 | 100 | 90 | 55 | — |
| R3-13 | 100 | 100 | 95 | 80 | 60 | 100 | 100 | 90 | 70 | — |
| R3-14 | 100 | 100 | 95 | 80 | 60 | 100 | 90 | 85 | 50 | — |
| R3-15 | 100 | 100 | 100 | 90 | 65 | 100 | 100 | 95 | 65 | — |
| R3-16 | 100 | 100 | 85 | 70 | — | 100 | 92 | 70 | 50 | — |
| R3-17 | 100 | 100 | 100 | 95 | 85 | 100 | 100 | 96 | 90 | 45 |
| R3-18 | 100 | 90 | 70 | 50 | — | 100 | 70 | 50 | — | — |
| R3-19 | 100 | 100 | 95 | 70 | — | 100 | 95 | 90 | 60 | — |
| R3-20 | 100 | 90 | 80 | 55 | — | 100 | 80 | 70 | 30 | — |
| R3-21 | 100 | 100 | 100 | 95 | 65 | 100 | 95 | 90 | 65 | — |
| R3-22 | 100 | 95 | 70 | 40 | — | 100 | 90 | 70 | 45 | — |
| R3-23 | 100 | 70 | 30 | — | — | 90 | 80 | 40 | — | — |
| R3-24 | 100 | 90 | 75 | 60 | — | 100 | 90 | 70 | 55 | — |

TABLE 4 the larvicidal mite $LC_{50}$ of highly active compounds in the formula R1-1~R1-25

| NO. (mg/L) | mortality of mite larvae (%) and $LC_{50}$ | | | | | | | |
|---|---|---|---|---|---|---|---|---|
| | 100 | 10 | 1 | 0.1 | 0.05 | formula (y = ax + b) | $LC_{50}$ | Correlation coefficient |
| R1-10 | 100 | 95 | 80 | 70 | 55/40[a] | y = 0.61x + 5.98 | 0.025 | 0.99 |
| R1-15 | 100 | 90 | 80 | 65 | 50/35[a] | y = 0.56x + 5.79 | 0.038 | 0.99 |
| R1-18 | 100 | 100 | 85 | 75 | 55/45[a] | y = 0.61x + 6.08 | 0.017 | 0.96 |
| R1-19 | 100 | 85 | 70 | 65 | 50/35[a] | y = 0.44x + 5.60 | 0.043 | 0.97 |
| R1-22 | 95 | 85 | 80 | 70 | 45 | y = 0.45x + 5.72 | 0.025 | 0.95 |
| Etoxazole | 100 | 90 | 80 | 65 | 30 | y = 0.68x + 5.71 | 0.088 | 0.92 |

[a]represent 0.01 mg/L

TABLE 5 the larvicidal $LC_{50}$ of highly active compounds in the formula R2-1~R2-24

| NO. (mg/L) | mortality of mite larvae (%) and $LC_{50}$ | | | | | | | | |
|---|---|---|---|---|---|---|---|---|---|
| | 10 | 1 | 0.5 | 0.1 | 0.01 | 0.001 | formula (y = ax + b) | $LC_{50}$ | Correlation coefficient |
| R2-2 | 100 | 92 | 83 | 75 | 50 | 30 | y = 0.61x + 6.28 | 0.0084 | 0.992 |
| R2-3 | 100 | 95 | 91 | 85 | 70 | 45 | y = 0.56x + 6.59 | 0.0015 | 0.996 |
| R2-5 | 100 | 95 | 90 | 80 | 65 | 37 | y = 0.62x + 6.55 | 0.0032 | 0.994 |
| R2-6 | 100 | 90 | 80 | 70 | 45 | 21 | y = 0.66x + 6.17 | 0.0166 | 0.994 |
| R2-19 | 95 | 85 | 72 | 65 | 30 | 8 | y = 0.77x + 5.96 | 0.0568 | 0.995 |
| R2-24 | 100 | 90 | 80 | 75 | 50 | 20 | y = 0.66x + 6.22 | 0.0140 | 0.988 |
| Etoxazole | 100 | 90 | 80 | 65 | 30 | — | y = 1.22x + 6.29 | 0.0880 | 0.950 |

TABLE 6 the larvicidal $LC_{50}$ of the highly active compounds in the formula R3-1~R3-24

| NO. (mg/L) | mortality of mite larvae (%) and $LC_{50}$ | | | | | | | |
|---|---|---|---|---|---|---|---|---|
| | 10 | 1 | 0.5 | 0.1 | 0.05 | formula (y = ax + b) | $LC_{50}$ | Correlation coefficient |
| R3-3 | 100 | 100 | 95 | 80 | 40 | y = 3.39x + 9.01 | 0.066 | 0.90 |
| R3-9 | 100 | 100 | 90 | 70 | 40 | y = 3.38x + 8.83 | 0.073 | 0.87 |
| R3-17 | 100 | 95 | 90 | 85 | 50/35[a] | y = 1.04x + 6.67 | 0.024 | 0.95 |
| Etoxazole | 100 | 90 | 80 | 65 | 30 | y = 1.22x + 6.29 | 0.088 | 0.95 |

[a]represent 0.01 mg/L

TABLE 7 the acaricidal $LC_{50}$ of the highly active compounds against mite eggs in the formula R1-1~R1-25

| NO. (mg/L) | mortality of mite eggs % and $LC_{50}$ 100 mg/L | 10 mg/L | 1 mg/L | 0.1 mg/L | 0.05 mg/L | formula (y = ax + b) | $LC_{50}$ | Correlation coefficient |
|---|---|---|---|---|---|---|---|---|
| R1-10 | 100 | 90 | 85 | 75 | 65/40[a] | y = 0.49x + 5.94 | 0.011 | 0.95 |
| R1-15 | 100 | 100 | 90 | 80 | 65/35[a] | y = 0.83x + 6.42 | 0.019 | 0.96 |
| R1-18 | 100 | 100 | 80 | 75 | 55/30[a] | y = 0.68x + 6.01 | 0.033 | 0.92 |
| R1-19 | 100 | 90 | 80 | 75 | 55/45[a] | y = 0.46x + 5.86 | 0.013 | 0.96 |
| R1-22 | 98 | 90 | 85 | 75 | 45 | y = 0.55x + 5.91 | 0.023 | 0.95 |
| Etoxazole | 100 | 90 | 70 | 60 | 30 | y = 0.68x + 5.60 | 0.128 | 0.95 |

[a]represent 0.01 mg/L

TABLE 8 the acaricidal $LC_{50}$ of the highly active derivatives against mite eggs in the formula R2-1~R2-24

| Compound mg/L | mortality of mite eggs % and $LC_{50}$ 10 | 1 | 0.5 | 0.1 | 0.01 | 0.001 | formula (y = ax + b) | $LC_{50}$ | Correlation coefficient |
|---|---|---|---|---|---|---|---|---|---|
| R2-2 | 100 | 95 | 90 | 88 | 65 | 40 | y = 0.61x + 6.62 | 0.0023 | 0.988 |
| R2-3 | 100 | 97 | 92 | 90 | 77 | 50 | y = 0.57x + 6.78 | 0.0008 | 0.983 |
| R2-5 | 100 | 95 | 90 | 85 | 70 | 47 | y = 0.56x + 6.72 | 0.0009 | 0.925 |
| R2-6 | 100 | 90 | 86 | 78 | 60 | 30 | y = 0.58x + 6.30 | 0.0057 | 0.994 |
| R2-19 | 100 | 90 | 80 | 65 | 32 | 10 | y = 0.83x + 6.20 | 0.0360 | 0.998 |
| R2-24 | 100 | 91 | 85 | 75 | 50 | 28 | y = 0.63x + 6.29 | 0.0090 | 0.998 |
| Etoxazole | 100 | 90 | 80 | 60 | 30 | — | y = 1.48x + 6.52 | 0.0950 | 0.970 |

TABLE 9 the acaricidal $LC_{50}$ of the highly active compounds against mite eggs in the formula R3-1~R3-24

| NO. (mg/L) | mortality of mite eggs % and $LC_{50}$ 10 | 1 | 0.5 | 0.1 | formula (y = ax + b) | $LC_{50}$ | Correlation coefficient |
|---|---|---|---|---|---|---|---|
| R3-3 | 100 | 90 | 75 | 50/20[a] | y = 1.28x + 6.75 | 0.043 | 0.99 |
| R3-9 | 90 | 75 | 60 | 30 | y = 1.21x + 6.21 | 0.101 | 0.96 |
| R3-17 | 96 | 90 | 78 | 45 | y = 1.28x + 6.75 | 0.043 | 0.96 |
| Etoxazole | 95 | 80 | 60 | 30 | y = 1.48x + 6.52 | 0.095 | 0.97 |

[a]represent 0.05 mg/L

By taking etoxazole as a reference, the activity tests of acaricidal activity against Tetranychus cinnabarinus eggs and larvae were carried out, and the oxazoline derivatives showed good acaricidal activity.

The compounds R1-10, R1-15, R1-18, R1-19, R1-22, R2-2, R2-3, R2-5, R2-6, R2-19 and R2-24 show higher acaricidal activity than etoxazole. In particular, the larvicidal activity of R1-18 is 5 times that of etoxazole, the acaricidal egg activity of R1-10 is 10 times that of etoxazole, the activity of the compound R2-3 to larvicidal is 58 times that of etoxazole, and the activity of R2-5 to larvicidal is 27 times that of etoxazole; the activity of the compounds R2-3 and R2-5 on mite eggs is 105 times of that of etoxazole. The compounds R3-3, R3-9 and R3-17 have remarkable acaricidal activity, and show equivalent or better acaricidal activity compared with etoxazole.

The preferred embodiments of the present invention have been described above in detail, but the present invention is not limited thereto. Within the scope of the technical idea of the invention, many simple modifications can be made to the technical solution of the invention, including various technical features being combined in any other suitable way, and these simple modifications and combinations should also be regarded as the disclosure of the invention, and all fall within the scope of the invention.

The invention claimed is:

1. An oxazoline compound which is characterized by having a structure shown in a formula (I), Formula (I)

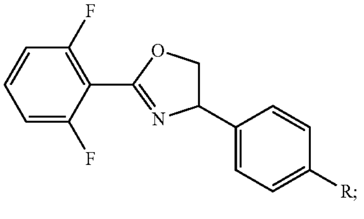

wherein, in the formula (I), R is selected from a group shown in a formula (I-1);

formula (I-1)

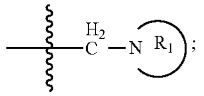

in the formula (I-1), the nitrogen-containing heterocyclic ring represented by $R_1$ is selected from substituted or unsubstituted five-membered to ten-membered single heterocyclic group, substituted or unsubstituted eight-membered to twelve-membered condensed bicyclic group, and the optional substituent groups on $R_1$ are each independently selected from at least one of halogen, $C_{1-10}$ alkyl, $C_{1-10}$ alkoxy and $C_{2-10}$ acyl.

2. A method for controlling phytophagous mites, comprising:

applying a mite-controlling effective amount of the oxazoline compound of claim 1 to a site or plant in need thereof.

3. The oxazoline compound of claim 1, wherein the oxazoline compound is selected from any one of the following compounds:

R1-1

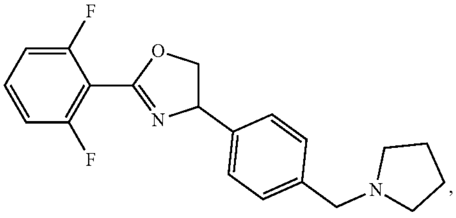

,

R1-2

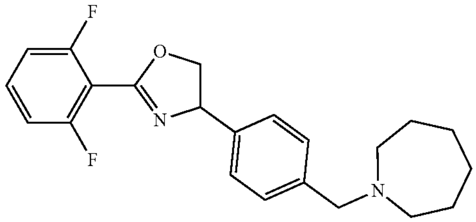

-continued

R1-3

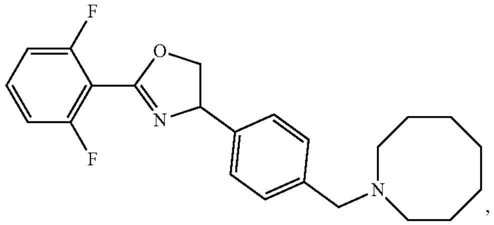

,

R1-4

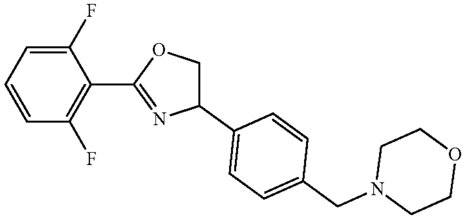

R1-5

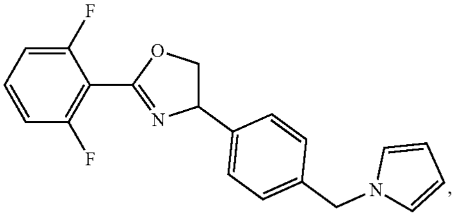

,

R1-6

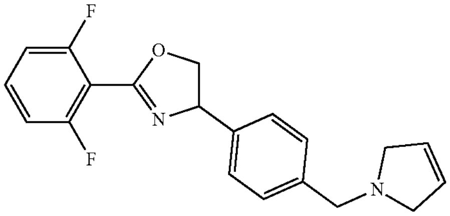

R1-7

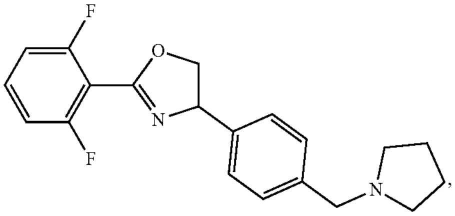

,

R1-8

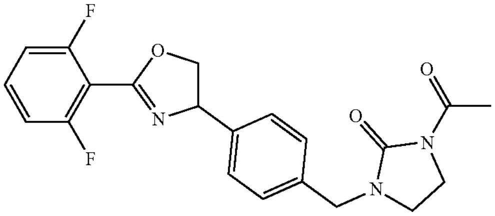

R1-9

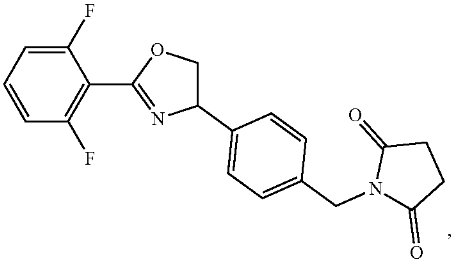

,

-continued
R1-10
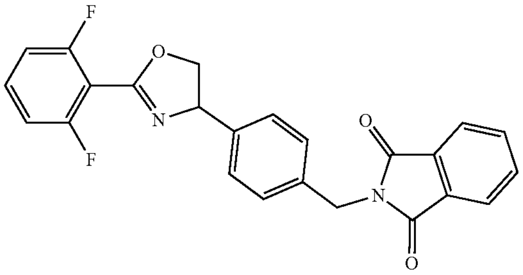
R1-11
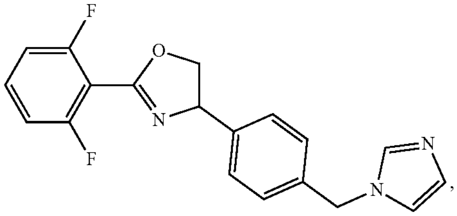
,
R1-12
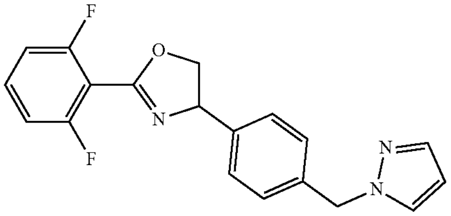
R1-13
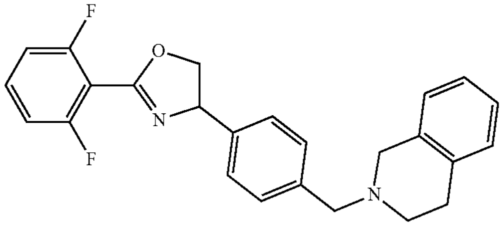
,
R1-14
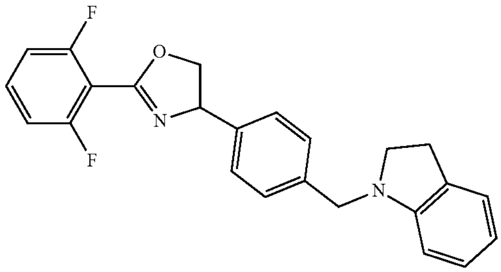
R1-15
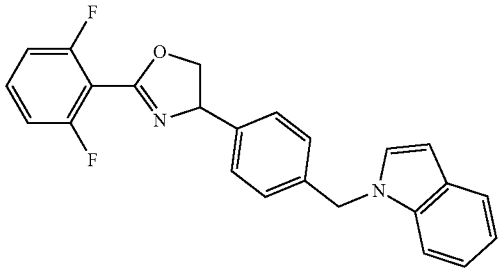
,
-continued
R1-16
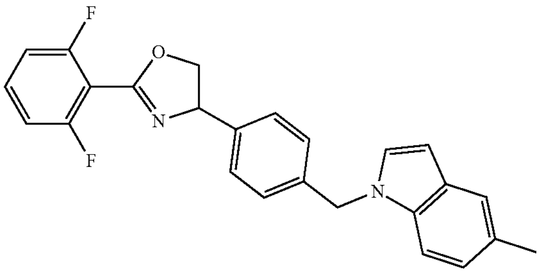
R1-17
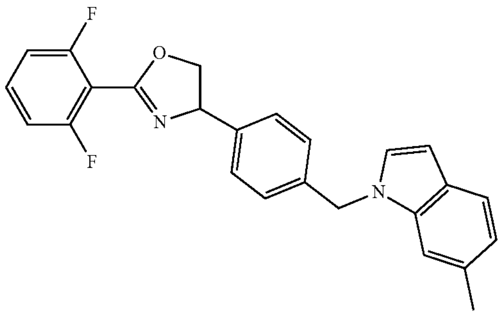
,
R1-18
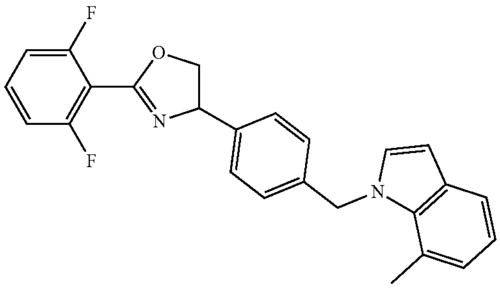
R1-19
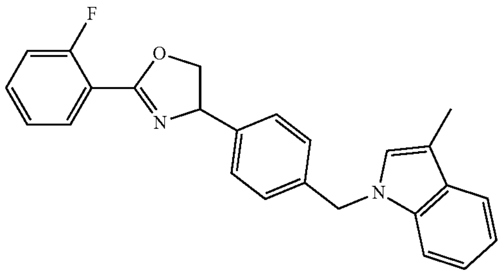
,
R1-20
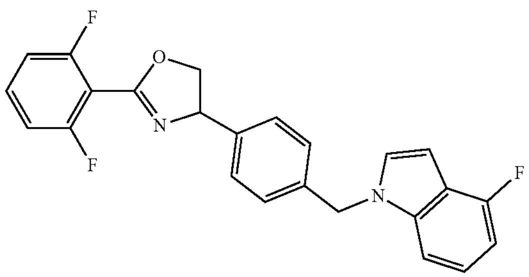

-continued
R1-21
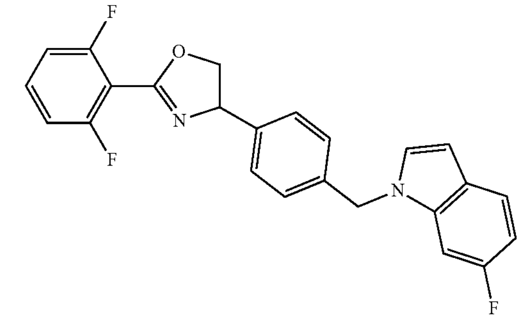
,
R1-22
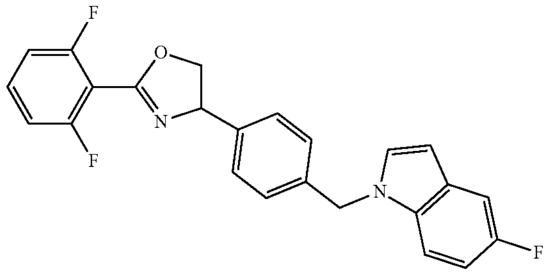
R1-23
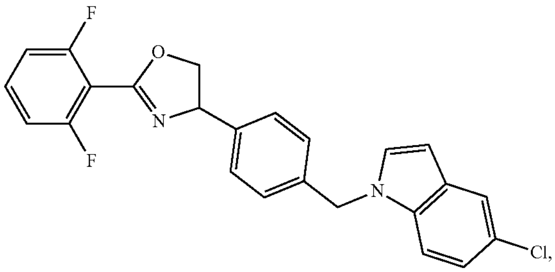
,
-continued
R1-24
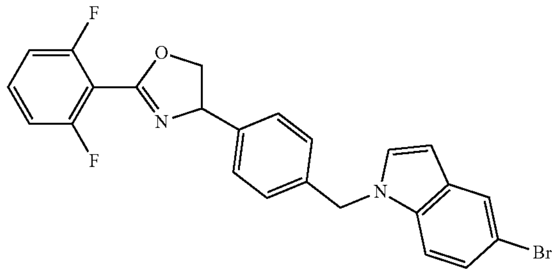
R1-25
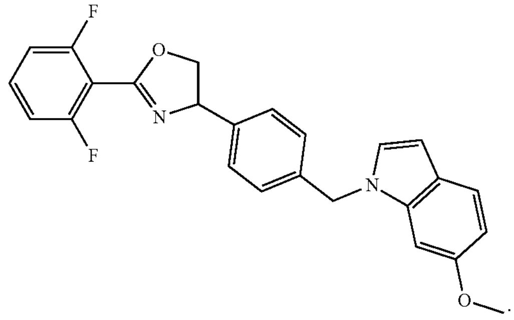
.
4. A method for controlling phytophagous mites, comprising: applying a mite-controlling effective amount of an oxazoline compound of claim 3 to a site or plant in need thereof.
* * * * *